(12) United States Patent
Keller et al.

(10) Patent No.: US 10,428,382 B2
(45) Date of Patent: Oct. 1, 2019

(54) MIRNA BASED TREATMENT MONITORING IN MULTIPLE SCLEROSIS

(71) Applicant: Comprehensive Biomarker Center GmbH, Heidelberg (DE)

(72) Inventors: Andreas Keller, Püttlingen (DE);
Markus Beier, Weinheim (DE);
Matthias Scheffler, Hirschberg (DE);
Anke Wendschlag, Mannheim (DE);
Orhan Aktas, Hilden (DE); Jens Ingwersen, Düsseldorf (DE);
Hans-Peter Hartung, Düsseldorf (DE);
Patrick Küry, Düsseldorf (DE);
Timour Prozorovski, Düsseldorf (DE)

(73) Assignee: Hummingbird Diagnostics GmbH, Heidelberg (DE)

( * ) Notice: Subject to any disclaimer, the term of this patent is extended or adjusted under 35 U.S.C. 154(b) by 0 days.

(21) Appl. No.: 14/383,518

(22) PCT Filed: Mar. 7, 2013

(86) PCT No.: PCT/EP2013/054648
§ 371 (c)(1),
(2) Date: Sep. 5, 2014

(87) PCT Pub. No.: WO2013/132025
PCT Pub. Date: Sep. 12, 2013

(65) Prior Publication Data
US 2015/0037327 A1    Feb. 5, 2015

(30) Foreign Application Priority Data

Mar. 7, 2012 (WO) ................. PCT/EP2012/053944

(51) Int. Cl.
*C12N 15/11* (2006.01)
*C12Q 1/6883* (2018.01)
*C07K 16/28* (2006.01)

(52) U.S. Cl.
CPC ........ *C12Q 1/6883* (2013.01); *C07K 16/2842* (2013.01); *C12Q 2600/106* (2013.01); *C12Q 2600/118* (2013.01); *C12Q 2600/136* (2013.01); *C12Q 2600/158* (2013.01); *C12Q 2600/178* (2013.01)

(58) Field of Classification Search
None
See application file for complete search history.

(56) References Cited

U.S. PATENT DOCUMENTS

| 2010/0167948 A1* | 7/2010 | Krichevsky | .......... C12Q 1/6883 506/9 |
| 2012/0015830 A1 | 1/2012 | Bigwood et al. | |

FOREIGN PATENT DOCUMENTS

| CN | 102002493 A | 4/2011 | |
| WO | WO 2010139811 A1 * | 12/2010 | ........... C12Q 1/6809 |
| WO | 2011/003989 A1 | 1/2011 | |
| WO | 2011/158191 A1 | 12/2011 | |
| WO | WO 2011163214 A2 * | 12/2011 | ........... C12Q 1/6883 |

OTHER PUBLICATIONS

Polman et al, A Randomized, Placebo-Controlled Trial of Natalizumab for Relapsing Multiple Sclerosis, 2006, The New England Journal of Medicine, vol. 354, 9: 899-910.*
Brown, "Natalizumab in the treatment of multiple sclerosis," *Therapeutics and Clinical Risk Management*, pp. 585-594 (2009).
Genechip miRNA Array, Retrieved from the Internet: URL:http://media.affymetrix.com/support/teChnical/datasheets/miRNA_datasheet.pdf, 2 pages (2012).
Junker, et al., "MicroRNA profiling of multiple sclerosis lesions identifies modulators of the regulatory protein CD47," *Brain*, vol. 132(12), pp. 3342-3352 (2009).
Sievers, et al., "Natalizumab treatment alters microRNA expression in B-lymphocytes in multiple sclerosis patients," *Multiple Sclerosis Journal*, vol. 17, pp. S127-S128 (2011).

(Continued)

*Primary Examiner* — Ekaterina Poliakova-Georgantas
(74) *Attorney, Agent, or Firm* — Kilpatrick Townsend & Stockton LLP

(57) ABSTRACT

The present invention relates to methods of determining whether a patient responds to a therapeutic treatment of multiple sclerosis (MS), of monitoring the course of multiple sclerosis (MS) in a patient, of determining the risk for a relapse of multiple sclerosis (MS) in a patient, and of adjusting the dose of a therapeutic drug applied for therapeutic treatment of multiple sclerosis in a patient. Said methods are based on the determination of the level of at least one miRNA in a test sample isolated from the patient. The present invention also relates to a method of identifying a compound suitable for the treatment of multiple sclerosis in a patient. Further, the present invention relates to the use of a polynucleotide or a polynucleotide set for detecting a miRNA to determine whether a patient responds to a therapeutic treatment of multiple sclerosis, to monitor the course of multiple sclerosis in a patient, to determine the risk of a relapse of multiple sclerosis in a patient, to adjust the dose of a therapeutic drug applied for therapeutic treatment of multiple sclerosis in a patient, and to identify a compound suitable for the treatment of multiple sclerosis in a patient. Furthermore, the present invention relates to a kit for determining whether a patient responds to a therapeutic treatment of multiple sclerosis, for monitoring the course of multiple sclerosis in a patient, for determining the risk of a relapse of multiple sclerosis in a patient, for adjusting the dose of a therapeutic drug applied for therapeutic treatment of multiple sclerosis in a patient, or for identifying a compound suitable for the treatment of multiple sclerosis in a patient comprising means for determining the level of at least one miRNA in a test sample isolated from a patient.

14 Claims, 9 Drawing Sheets

Specification includes a Sequence Listing.

(56) References Cited

OTHER PUBLICATIONS

Sievers, et al., "Altered microRNA expression in B lymphocytes in multiple sclerosis," *Clinical Immunology*, vol. 144, pp. 70-79 (2012).
Waschbisch, et al., "Glatiramer Acetate Treatment Normalizes Deregulated microRNA Expression in Relapsing Remitting Multiple Sclerosis," *Plos One*, vol. 6(9), E24604, 6 pages (2011).
International Search Report for International Application No. PCT/EP2013/054648, 9 pages, dated Aug. 20, 2013.

* cited by examiner

Figure 1

| SEQ ID NO: | Name (miRNA, miRNA*) | SEQUENCE (5'-3') |
|---|---|---|
| SEQ ID NO: 1 | hsa-miR-18a | uaaggugcaucuagugcagauag |
| SEQ ID NO: 2 | hsa-miR-29a | uagcaccaucugaaaucgguua |
| SEQ ID NO: 3 | hsa-miR-20b | caaagugcucauagugcagguag |
| SEQ ID NO: 4 | hsa-miR-103 | agcagcauuguacagggcuauga |
| SEQ ID NO: 5 | hsa-miR-532-5p | caugccuugaguguaggaccgu |
| SEQ ID NO: 6 | hsa-miR-24 | uggcucaguucagcaggaacag |
| SEQ ID NO: 7 | hsa-miR-342-3p | ucucacacagaaaucgcacccgu |
| SEQ ID NO: 8 | hsa-miR-7-1* | caacaaaucacagucugccaua |
| SEQ ID NO: 9 | hsa-miR-326 | ccucugggcccuuccuccag |
| SEQ ID NO: 10 | hsa-miR-411* | uauguaacacgguccacuaacc |
| SEQ ID NO: 11 | hsa-let-7d* | cuauacgaccugcugccuuucu |
| SEQ ID NO: 12 | hsa-miR-380* | ugguugaccauagaacaugcgc |
| SEQ ID NO: 13 | hsa-miR-2117 | ugucucuuugccaaggacag |
| SEQ ID NO: 14 | hsa-miR-2116* | ccucccaugccaagaacuccc |
| SEQ ID NO: 15 | hsa-miR-1237 | uccuucugcuccgucccccag |

(A)

| SEQ ID NO | mirna | median g1 (RRMS baseline) | median g2 (RRMS natalizumab) | log2 median g1 (RRMS baseline) | log2 median g2 (RRMS natalizumab) | qmedian | log2 qmedian | ttest, raw pval |
|---|---|---|---|---|---|---|---|---|
| 1 | hsa-miR-18a | 911 | 1643 | 9.83 | 10.68 | 1.80 | 0.85 | 2.48E-02 |
| 2 | hsa-miR-29a | 579 | 978 | 9.18 | 9.93 | 1.69 | 0.76 | 3.35E-02 |
| 3 | hsa-miR-20b | 3083 | 5061 | 11.59 | 12.31 | 1.64 | 0.72 | 2.66E-02 |
| 4 | hsa-miR-103 | 6603 | 10489 | 12.69 | 13.36 | 1.59 | 0.67 | 7.82E-03 |
| 5 | hsa-miR-532-5p | 259 | 406 | 8.02 | 8.66 | 1.57 | 0.65 | 2.05E-02 |
| 6 | hsa-miR-24 | 1306 | 2035 | 10.35 | 10.99 | 1.56 | 0.64 | 1.94E-02 |
| 7 | hsa-miR-342-3p | 4789 | 6722 | 12.23 | 12.71 | 1.40 | 0.49 | 4.81E-02 |
| 8 | hsa-miR-7-1* | 353 | 462 | 8.46 | 8.85 | 1.31 | 0.39 | 4.88E-02 |
| 10 | hsa-miR-411* | 129 | 78 | 7.01 | 6.28 | 0.61 | -0.72 | 5.54E-03 |
| 11 | hsa-let-7d* | 146 | 92 | 7.19 | 6.52 | 0.63 | -0.67 | 7.31E-03 |
| 12 | hsa-miR-380* | 151 | 96 | 7.23 | 6.58 | 0.64 | -0.65 | 1.32E-02 |
| 13 | hsa-miR-2117 | 147 | 94 | 7.20 | 6.56 | 0.64 | -0.64 | 3.96E-02 |
| 14 | hsa-miR-2116* | 281 | 213 | 8.14 | 7.74 | 0.76 | -0.40 | 1.46E-02 |
| 15 | hsa-miR-1237 | 191 | 156 | 7.58 | 7.38 | 0.82 | -0.30 | 4.85E-02 |
| 9 | hsa-miR-326 | 184 | 150 | 7.52 | 7.23 | 0.82 | -0.29 | 2.45E-01 |

(B)

| SEQ ID NO | miRNA | median g1 (healthy control) | median g2 (RRMS) | log2 median g1 (healthy control) | log2 median g2 (RRMS) | qmedian | log2 qmedian | ttest rawp | ttest adjp | limma rawp | limma adjp |
|---|---|---|---|---|---|---|---|---|---|---|---|
| 1 | hsa-miR-18a | 2414 | 588 | 11.24 | 9.20 | 0.24 | -2.04 | 1.28E-03 | 1.85E-02 | 1.88E-09 | 7.99E-07 |
| 2 | hsa-miR-29a | 665 | 325 | 9.38 | 8.34 | 0.49 | -1.03 | 3.28E-02 | 1.12E-01 | 4.59E-03 | 2.37E-02 |
| 3 | hsa-miR-20b | 5627 | 2472 | 12.46 | 11.27 | 0.44 | -1.19 | 2.18E-03 | 2.53E-02 | 8.01E-05 | 1.01E-03 |
| 4 | hsa-miR-103 | 8739 | 5003 | 13.09 | 12.29 | 0.57 | -0.80 | 2.70E-02 | 9.95E-02 | 1.79E-03 | 1.11E-02 |
| 5 | hsa-miR-532-5p | 390 | 149 | 8.61 | 7.22 | 0.38 | -1.39 | 7.01E-03 | 4.64E-02 | 9.39E-05 | 1.15E-03 |
| 6 | hsa-miR-24 | 3124 | 997 | 11.61 | 9.96 | 0.32 | -1.65 | 1.16E-03 | 1.76E-02 | 7.64E-06 | 2.02E-04 |
| 8 | hsa-miR-7-1* | 332 | 249 | 8.38 | 7.96 | 0.75 | -0.42 | 9.15E-01 | 9.53E-01 | 6.77E-01 | 8.10E-01 |
| 10 | hsa-miR-411* | 62 | 70 | 5.95 | 6.12 | 1.13 | 0.18 | 8.65E-02 | 2.09E-01 | 2.50E-01 | 4.13E-01 |
| 11 | hsa-let-7d* | 59 | 67 | 5.89 | 6.07 | 1.13 | 0.18 | 1.62E-01 | 3.13E-01 | 4.00E-01 | 5.64E-01 |
| 15 | hsa-miR-1237 | 106 | 126 | 6.73 | 6.98 | 1.19 | 0.25 | 9.95E-02 | 2.26E-01 | 1.32E-01 | 2.57E-01 |
| 9 | hsa-miR-326 | 85 | 95 | 6.41 | 6.58 | 1.12 | 0.16 | 7.35E-01 | 8.45E-01 | 5.89E-01 | 7.40E-01 |

Figure 6
(A)
| SEQ ID NO | miRNA | median (healthy control) | median (RRMS baseline) | median (RRMS-natalizumab) | log2 FC (RRMS vs healthy control) | log2 FC (natalizumab vs RRMS) |
|---|---|---|---|---|---|---|
| 1 | hsa-miR-18a | 3738 | 911 | 1643 | -2.04 | 0.85 |
| 2 | hsa-miR-29a | 1184 | 579 | 978 | -1.03 | 0.76 |
| 3 | hsa-miR-20b | 7018 | 3083 | 5061 | -1.19 | 0.72 |
| 4 | hsa-miR-103 | 11534 | 6603 | 10489 | -0.80 | 0.67 |
| 9 | hsa-miR-326 | 164 | 184 | 150 | 0.16 | -0.29 |
(B)
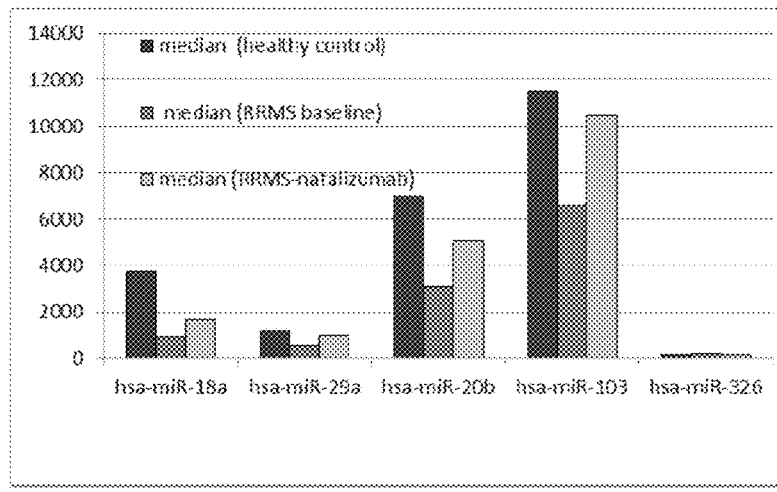
(C)
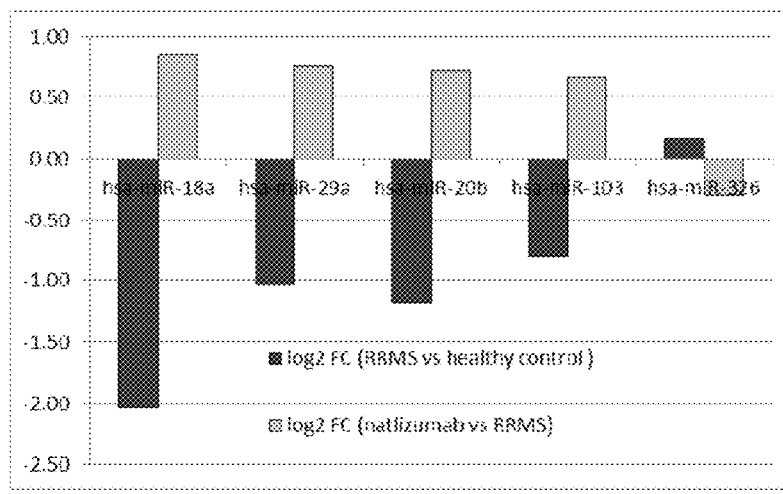

Figure 8

| Signature | SEQ ID NOs | miRNA identifiers |
|---|---|---|
| MST-1 | SEQ ID NO: 1, SEQ ID NO: 2 | hsa-miR-18a, hsa-miR-29a |
| MST-2 | SEQ ID NO: 2, SEQ ID NO: 3 | hsa-miR-29a, hsa-miR-20b |
| MST-3 | SEQ ID NO: 3, SEQ ID NO: 4 | hsa-miR-20b, hsa-miR-103 |
| MST-4 | SEQ ID NO: 4, SEQ ID NO: 9 | hsa-miR-103, hsa-miR-326 |
| MST-5 | SEQ ID NO: 9, SEQ ID NO: 5 | hsa-miR-326, hsa-miR-532-5p |
| MST-6 | SEQ ID NO: 5, SEQ ID NO: 6 | hsa-miR-532-5p, hsa-miR-24 |
| MST-7 | SEQ ID NO: 6, SEQ ID NO: 7 | hsa-miR-24, hsa-miR-342-3p |
| MST-8 | SEQ ID NO: 7, SEQ ID NO: 8 | hsa-miR-342-3p, hsa-miR-7-1* |
| MST-9 | SEQ ID NO: 8, SEQ ID NO: 10 | hsa-miR-7-1*, hsa-miR-411* |
| MST-10 | SEQ ID NO: 10, SEQ ID NO: 11 | hsa-miR-411*, hsa-let-7d* |
| MST-11 | SEQ ID NO: 11, SEQ ID NO: 12 | hsa-let-7d*, hsa-miR-380* |
| MST-12 | SEQ ID NO: 12, SEQ ID NO: 13 | hsa-miR-380*, hsa-miR-2117 |
| MST-13 | SEQ ID NO: 13, SEQ ID NO: 14 | hsa-miR-2117, hsa-miR-2116* |
| MST-14 | SEQ ID NO: 14, SEQ ID NO: 15 | hsa-miR-2116*, hsa-miR-1237 |
| MST-15 | SEQ ID NO: 1, SEQ ID NO: 3 | hsa-miR-18a, hsa-miR-20b |
| MST-16 | SEQ ID NO: 2, SEQ ID NO: 4 | hsa-miR-29a, hsa-miR-103 |
| MST-17 | SEQ ID NO: 3, SEQ ID NO: 9 | hsa-miR-20b, hsa-miR-326 |
| MST-18 | SEQ ID NO: 4, SEQ ID NO: 5 | hsa-miR-103, hsa-miR-532-5p |
| MST-19 | SEQ ID NO: 9, SEQ ID NO: 6 | hsa-miR-326, hsa-miR-24 |
| MST-20 | SEQ ID NO: 5, SEQ ID NO: 7 | hsa-miR-532-5p, hsa-miR-342-3p |
| MST-21 | SEQ ID NO: 6, SEQ ID NO: 8 | hsa-miR-24, hsa-miR-7-1* |
| MST-22 | SEQ ID NO: 7, SEQ ID NO: 10 | hsa-miR-342-3p, hsa-miR-411* |
| MST-23 | SEQ ID NO: 8, SEQ ID NO: 11 | hsa-miR-7-1*, hsa-let-7d* |
| MST-24 | SEQ ID NO: 10, SEQ ID NO: 12 | hsa-miR-411*, hsa-miR-380* |
| MST-25 | SEQ ID NO: 11, SEQ ID NO: 13 | hsa-let-7d*, hsa-miR-2117 |
| MST-26 | SEQ ID NO: 12, SEQ ID NO: 14 | hsa-miR-380*, hsa-miR-2116* |
| MST-27 | SEQ ID NO: 13, SEQ ID NO: 15 | hsa-miR-2117, hsa-miR-1237 |
| MST-28 | SEQ ID NO: 1, SEQ ID NO: 4 | hsa-miR-18a, hsa-miR-103 |
| MST-29 | SEQ ID NO: 2, SEQ ID NO: 9 | hsa-miR-29a, hsa-miR-326 |
| MST-30 | SEQ ID NO: 3, SEQ ID NO: 5 | hsa-miR-20b, hsa-miR-532-5p |
| MST-31 | SEQ ID NO: 4, SEQ ID NO: 6 | hsa-miR-103, hsa-miR-24 |
| MST-32 | SEQ ID NO: 9, SEQ ID NO: 7 | hsa-miR-326, hsa-miR-342-3p |
| MST-33 | SEQ ID NO: 5, SEQ ID NO: 8 | hsa-miR-532-5p, hsa-miR-7-1* |
| MST-34 | SEQ ID NO: 6, SEQ ID NO: 10 | hsa-miR-24, hsa-miR-411* |
| MST-35 | SEQ ID NO: 7, SEQ ID NO: 11 | hsa-miR-342-3p, hsa-let-7d* |
| MST-36 | SEQ ID NO: 8, SEQ ID NO: 12 | hsa-miR-7-1*, hsa-miR-380* |
| MST-37 | SEQ ID NO: 10, SEQ ID NO: 13 | hsa-miR-411*, hsa-miR-2117 |
| MST-38 | SEQ ID NO: 11, SEQ ID NO: 14 | hsa-let-7d*, hsa-miR-2116* |
| MST-39 | SEQ ID NO: 12, SEQ ID NO: 15 | hsa-miR-380*, hsa-miR-1237 |
| MST-40 | SEQ ID NO: 1, SEQ ID NO: 2, SEQ ID NO: 3 | hsa-miR-18a, hsa-miR-29a, hsa-miR-20b |
| MST-41 | SEQ ID NO: 2, SEQ ID NO: 3, SEQ ID NO: 4 | hsa-miR-29a, hsa-miR-20b, hsa-miR-103 |

FIGURE 8 (Cont.)

| MST-42 | SEQ ID NO: 3, SEQ ID NO: 4, SEQ ID NO: 9 | hsa-miR-20b, hsa-miR-103, hsa-miR-326 |
|---|---|---|
| MST-43 | SEQ ID NO: 4, SEQ ID NO: 9, SEQ ID NO: 5 | hsa-miR-103, hsa-miR-326, hsa-miR-532-5p |
| MST-44 | SEQ ID NO: 9, SEQ ID NO: 5, SEQ ID NO: 6 | hsa-miR-326, hsa-miR-532-5p, hsa-miR-24 |
| MST-45 | SEQ ID NO: 5, SEQ ID NO: 6, SEQ ID NO: 7 | hsa-miR-532-5p, hsa-miR-24, hsa-miR-342-3p |
| MST-46 | SEQ ID NO: 6, SEQ ID NO: 7, SEQ ID NO: 8 | hsa-miR-24, hsa-miR-342-3p, hsa-miR-7-1* |
| MST-47 | SEQ ID NO: 7, SEQ ID NO: 8, SEQ ID NO: 10 | hsa-miR-342-3p, hsa-miR-7-1*, hsa-miR-411* |
| MST-48 | SEQ ID NO: 8, SEQ ID NO: 10, SEQ ID NO: 11 | hsa-miR-7-1*, hsa-miR-411*, hsa-let-7d* |
| MST-49 | SEQ ID NO: 10, SEQ ID NO: 11, SEQ ID NO: 12 | hsa-miR-411*, hsa-let-7d*, hsa-miR-380* |
| MST-50 | SEQ ID NO: 11, SEQ ID NO: 12, SEQ ID NO: 13 | hsa-let-7d*, hsa-miR-380*, hsa-miR-2117 |
| MST-51 | SEQ ID NO: 12, SEQ ID NO: 13, SEQ ID NO: 14 | hsa-miR-380*, hsa-miR-2117, hsa-miR-2116* |
| MST-52 | SEQ ID NO: 13, SEQ ID NO: 14, SEQ ID NO: 15 | hsa-miR-2117, hsa-miR-2116*, hsa-miR-1237 |
| MST-53 | SEQ ID NO: 1, SEQ ID NO: 2, SEQ ID NO: 4 | hsa-miR-18a, hsa-miR-29a, hsa-miR-103 |
| MST-54 | SEQ ID NO: 2, SEQ ID NO: 3, SEQ ID NO: 9 | hsa-miR-29a, hsa-miR-20b, hsa-miR-326 |
| MST-55 | SEQ ID NO: 3, SEQ ID NO: 4, SEQ ID NO: 5 | hsa-miR-20b, hsa-miR-103, hsa-miR-532-5p |
| MST-56 | SEQ ID NO: 4, SEQ ID NO: 9, SEQ ID NO: 6 | hsa-miR-103, hsa-miR-326, hsa-miR-24 |
| MST-57 | SEQ ID NO: 9, SEQ ID NO: 5, SEQ ID NO: 7 | hsa-miR-326, hsa-miR-532-5p, hsa-miR-342-3p |
| MST-58 | SEQ ID NO: 5, SEQ ID NO: 6, SEQ ID NO: 8 | hsa-miR-532-5p, hsa-miR-24, hsa-miR-7-1* |
| MST-59 | SEQ ID NO: 6, SEQ ID NO: 7, SEQ ID NO: 10 | hsa-miR-24, hsa-miR-342-3p, hsa-miR-411* |
| MST-60 | SEQ ID NO: 7, SEQ ID NO: 8, SEQ ID NO: 11 | hsa-miR-342-3p, hsa-miR-7-1*, hsa-let-7d* |
| MST-61 | SEQ ID NO: 8, SEQ ID NO: 10, SEQ ID NO: 12 | hsa-miR-7-1*, hsa-miR-411*, hsa-miR-380* |
| MST-62 | SEQ ID NO: 10, SEQ ID NO: 11, SEQ ID NO: 13 | hsa-miR-411*, hsa-let-7d*, hsa-miR-2117 |
| MST-63 | SEQ ID NO: 11, SEQ ID NO: 12, SEQ ID NO: 14 | hsa-let-7d*, hsa-miR-380*, hsa-miR-2116* |
| MST-64 | SEQ ID NO: 12, SEQ ID NO: 13, SEQ ID NO: 15 | hsa-miR-380*, hsa-miR-2117, hsa-miR-1237 |
| MST-65 | SEQ ID NO: 1, SEQ ID NO: 3, SEQ ID NO: 4 | hsa-miR-18a, hsa-miR-20b, hsa-miR-103 |
| MST-66 | SEQ ID NO: 2, SEQ ID NO: 4, SEQ ID NO: 9 | hsa-miR-29a, hsa-miR-103, hsa-miR-326 |
| MST-67 | SEQ ID NO: 3, SEQ ID NO: 9, SEQ ID NO: 5 | hsa-miR-20b, hsa-miR-326, hsa-miR-532-5p |
| MST-68 | SEQ ID NO: 4, SEQ ID NO: 5, SEQ ID NO: 6 | hsa-miR-103, hsa-miR-532-5p, hsa-miR-24 |
| MST-69 | SEQ ID NO: 9, SEQ ID NO: 6, SEQ ID NO: 7 | hsa-miR-326, hsa-miR-24, hsa-miR-342-3p |
| MST-70 | SEQ ID NO: 5, SEQ ID NO: 7, SEQ ID NO: 8 | hsa-miR-532-5p, hsa-miR-342-3p, hsa-miR-7-1* |
| MST-71 | SEQ ID NO: 6, SEQ ID NO: 8, SEQ ID NO: 10 | hsa-miR-24, hsa-miR-7-1*, hsa-miR-411* |
| MST-72 | SEQ ID NO: 7, SEQ ID NO: 10, SEQ ID NO: 11 | hsa-miR-342-3p, hsa-miR-411*, hsa-let-7d* |
| MST-73 | SEQ ID NO: 8, SEQ ID NO: 11, SEQ ID NO: 12 | hsa-miR-7-1*, hsa-let-7d*, hsa-miR-380* |
| MST-74 | SEQ ID NO: 10, SEQ ID NO: 12, SEQ ID NO: 13 | hsa-miR-411*, hsa-miR-380*, hsa-miR-2117 |
| MST-75 | SEQ ID NO: 11, SEQ ID NO: 13, SEQ ID NO: 14 | hsa-let-7d*, hsa-miR-2117, hsa-miR-2116* |
| MST-76 | SEQ ID NO: 12, SEQ ID NO: 14, SEQ ID NO: 15 | hsa-miR-380*, hsa-miR-2116*, hsa-miR-1237 |
| MST-77 | SEQ ID NO: 1, SEQ ID NO: 3, SEQ ID NO: 9 | hsa-miR-18a, hsa-miR-20b, hsa-miR-326 |
| MST-78 | SEQ ID NO: 2, SEQ ID NO: 4, SEQ ID NO: 5 | hsa-miR-29a, hsa-miR-103, hsa-miR-532-5p |
| MST-79 | SEQ ID NO: 3, SEQ ID NO: 9, SEQ ID NO: 6 | hsa-miR-20b, hsa-miR-326, hsa-miR-24 |
| MST-80 | SEQ ID NO: 4, SEQ ID NO: 5, SEQ ID NO: 7 | hsa-miR-103, hsa-miR-532-5p, hsa-miR-342-3p |
| MST-81 | SEQ ID NO: 9, SEQ ID NO: 6, SEQ ID NO: 8 | hsa-miR-326, hsa-miR-24, hsa-miR-7-1* |
| MST-82 | SEQ ID NO: 5, SEQ ID NO: 7, SEQ ID NO: 10 | hsa-miR-532-5p, hsa-miR-342-3p, hsa-miR-411* |
| MST-83 | SEQ ID NO: 6, SEQ ID NO: 8, SEQ ID NO: 11 | hsa-miR-24, hsa-miR-7-1*, hsa-let-7d* |
| MST-84 | SEQ ID NO: 7, SEQ ID NO: 10, SEQ ID NO: 12 | hsa-miR-342-3p, hsa-miR-411*, hsa-miR-380* |
| MST-85 | SEQ ID NO: 8, SEQ ID NO: 11, SEQ ID NO: 13 | hsa-miR-7-1*, hsa-let-7d*, hsa-miR-2117 |
| MST-86 | SEQ ID NO: 10, SEQ ID NO: 12, SEQ ID NO: 14 | hsa-miR-411*, hsa-miR-380*, hsa-miR-2116* |
| MST-87 | SEQ ID NO: 11, SEQ ID NO: 13, SEQ ID NO: 15 | hsa-let-7d*, hsa-miR-2117, hsa-miR-1237 |

FIGURE 8 (Cont.)

| MST-88 | SEQ ID NO: 1, SEQ ID NO: 2, SEQ ID NO: 9 | hsa-miR-18a, hsa-miR-29a, hsa-miR-326 |
|---|---|---|
| MST-89 | SEQ ID NO: 2, SEQ ID NO: 3, SEQ ID NO: 5 | hsa-miR-29a, hsa-miR-20b, hsa-miR-532-5p |
| MST-90 | SEQ ID NO: 3, SEQ ID NO: 4, SEQ ID NO: 6 | hsa-miR-20b, hsa-miR-103, hsa-miR-24 |
| MST-91 | SEQ ID NO: 4, SEQ ID NO: 9, SEQ ID NO: 7 | hsa-miR-103, hsa-miR-326, hsa-miR-342-3p |
| MST-92 | SEQ ID NO: 9, SEQ ID NO: 5, SEQ ID NO: 8 | hsa-miR-326, hsa-miR-532-5p, hsa-miR-7-1* |
| MST-93 | SEQ ID NO: 5, SEQ ID NO: 6, SEQ ID NO: 10 | hsa-miR-532-5p, hsa-miR-24, hsa-miR-411* |
| MST-94 | SEQ ID NO: 6, SEQ ID NO: 7, SEQ ID NO: 11 | hsa-miR-24, hsa-miR-342-3p, hsa-let-7d* |
| MST-95 | SEQ ID NO: 7, SEQ ID NO: 8, SEQ ID NO: 12 | hsa-miR-342-3p, hsa-miR-7-1*, hsa-miR-380* |
| MST-96 | SEQ ID NO: 8, SEQ ID NO: 10, SEQ ID NO: 13 | hsa-miR-7-1*, hsa-miR-411*, hsa-miR-2117 |
| MST-97 | SEQ ID NO: 10, SEQ ID NO: 11, SEQ ID NO: 14 | hsa-miR-411*, hsa-let-7d*, hsa-miR-2116* |
| MST-98 | SEQ ID NO: 11, SEQ ID NO: 12, SEQ ID NO: 15 | hsa-let-7d*, hsa-miR-380*, hsa-miR-1237 |
| MST-99 | SEQ ID NO: 1, SEQ ID NO: 4, SEQ ID NO: 9 | hsa-miR-18a, hsa-miR-103, hsa-miR-326 |
| MST-100 | SEQ ID NO: 2, SEQ ID NO: 9, SEQ ID NO: 5 | hsa-miR-29a, hsa-miR-326, hsa-miR-532-5p |
| MST-101 | SEQ ID NO: 3, SEQ ID NO: 5, SEQ ID NO: 6 | hsa-miR-20b, hsa-miR-532-5p, hsa-miR-24 |
| MST-102 | SEQ ID NO: 4, SEQ ID NO: 6, SEQ ID NO: 7 | hsa-miR-103, hsa-miR-24, hsa-miR-342-3p |
| MST-103 | SEQ ID NO: 9, SEQ ID NO: 7, SEQ ID NO: 8 | hsa-miR-326, hsa-miR-342-3p, hsa-miR-7-1* |
| MST-104 | SEQ ID NO: 5, SEQ ID NO: 8, SEQ ID NO: 10 | hsa-miR-532-5p, hsa-miR-7-1*, hsa-miR-411* |
| MST-105 | SEQ ID NO: 6, SEQ ID NO: 10, SEQ ID NO: 11 | hsa-miR-24, hsa-miR-411*, hsa-let-7d* |
| MST-106 | SEQ ID NO: 7, SEQ ID NO: 11, SEQ ID NO: 12 | hsa-miR-342-3p, hsa-let-7d*, hsa-miR-380* |
| MST-107 | SEQ ID NO: 8, SEQ ID NO: 12, SEQ ID NO: 13 | hsa-miR-7-1*, hsa-miR-380*, hsa-miR-2117 |
| MST-108 | SEQ ID NO: 10, SEQ ID NO: 13, SEQ ID NO: 14 | hsa-miR-411*, hsa-miR-2117, hsa-miR-2116* |
| MST-109 | SEQ ID NO: 11, SEQ ID NO: 14, SEQ ID NO: 15 | hsa-let-7d*, hsa-miR-2116*, hsa-miR-1237 |

SEQUENCE LISTING

```
<160> NUMBER OF SEQ ID NOS: 15

<210> SEQ ID NO 1
<211> LENGTH: 23
<212> TYPE: RNA
<213> ORGANISM: Homo sapiens

<400> SEQUENCE: 1
uaaggugcau cuagugcaga uag                                              23

<210> SEQ ID NO 2
<211> LENGTH: 22
<212> TYPE: RNA
<213> ORGANISM: Homo sapiens

<400> SEQUENCE: 2
uagcaccauc ugaaaucggu ua                                               22

<210> SEQ ID NO 3
<211> LENGTH: 23
<212> TYPE: RNA
<213> ORGANISM: Homo sapiens

<400> SEQUENCE: 3
caaagugcuc auagugcagg uag                                              23

<210> SEQ ID NO 4
<211> LENGTH: 23
<212> TYPE: RNA
<213> ORGANISM: Homo sapiens

<400> SEQUENCE: 4
agcagcauug uacagggcua uga                                              23
```

```
<210> SEQ ID NO 5
<211> LENGTH: 22
<212> TYPE: RNA
<213> ORGANISM: Homo sapiens

<400> SEQUENCE: 5
caugccuuga guguaggacc gu                                             22

<210> SEQ ID NO 6
<211> LENGTH: 22
<212> TYPE: RNA
<213> ORGANISM: Homo sapiens

<400> SEQUENCE: 6
uggcucaguu cagcaggaac ag                                             22

<210> SEQ ID NO 7
<211> LENGTH: 23
<212> TYPE: RNA
<213> ORGANISM: Homo sapiens

<400> SEQUENCE: 7
ucucacacag aaaucgcacc cgu                                            23

<210> SEQ ID NO 8
<211> LENGTH: 22
<212> TYPE: RNA
<213> ORGANISM: Homo sapiens

<400> SEQUENCE: 8
caacaaauca cagucugcca ua                                             22

<210> SEQ ID NO 9
<211> LENGTH: 20
<212> TYPE: RNA
<213> ORGANISM: Homo sapiens

<400> SEQUENCE: 9
ccucugggcc cuuccuccag                                                20

<210> SEQ ID NO 10
<211> LENGTH: 22
<212> TYPE: RNA
<213> ORGANISM: Homo sapiens

<400> SEQUENCE: 10
uauguaacac gguccacuaa cc                                             22

<210> SEQ ID NO 11
<211> LENGTH: 22
<212> TYPE: RNA
<213> ORGANISM: Homo sapiens

<400> SEQUENCE: 11
cuauacgacc ugcugccuuu cu                                             22

<210> SEQ ID NO 12
<211> LENGTH: 22
<212> TYPE: RNA
<213> ORGANISM: Homo sapiens

<400> SEQUENCE: 12
ugguugacca uagaacaugc gc                                             22
```

```
<210> SEQ ID NO 13
<211> LENGTH: 21
<212> TYPE: RNA
<213> ORGANISM: Homo sapiens

<400> SEQUENCE: 13
uguucucuuu gccaaggaca g                                              21

<210> SEQ ID NO 14
<211> LENGTH: 21
<212> TYPE: RNA
<213> ORGANISM: Homo sapiens

<400> SEQUENCE: 14
ccucccaugc caagaacucc c                                              21

<210> SEQ ID NO 15
<211> LENGTH: 21
<212> TYPE: RNA
<213> ORGANISM: Homo sapiens

<400> SEQUENCE: 15
uccuucugcu ccgucccca g                                               21
```

MIRNA BASED TREATMENT MONITORING IN MULTIPLE SCLEROSIS

CROSS-REFERENCE TO RELATED APPLICATIONS

This application is the U.S. National Stage entry of PCT/EP2013/054648, filed Mar. 7, 2013, which claims priority to International Application No. PCT/EP2012/053944, filed Mar. 7, 2012.

REFERENCE TO A SEQUENCE LISTING

This application includes a Sequence Listing named "95697-918187.txt" created on Oct. 17, 2014 and containing 2,805 bytes. The material contained in this text file is incorporated by reference in its entirety for all purposes.

TECHNICAL FIELD OF THE INVENTION

The invention relates to methods of determining whether a patient responds to a therapeutic treatment of multiple sclerosis (MS), of monitoring the course of multiple sclerosis (MS) in a patient, of determining the risk for a relapse of multiple sclerosis (MS) in a patient, and of adjusting the dose of a therapeutic drug applied for therapeutic treatment of multiple sclerosis in a patient. Said methods are based on the determination of the level of at least one miRNA in a test sample isolated from the patient. The invention also relates to a method of identifying a compound suitable for the treatment of multiple sclerosis in a patient. Further, the invention relates to the use of a polynucleotide or a polynucleotide set for detecting a miRNA to determine whether a patient responds to a therapeutic treatment of multiple sclerosis, to monitor the course of multiple sclerosis in a patient, to determine the risk of a relapse of multiple sclerosis in a patient, to adjust the dose of a therapeutic drug applied for therapeutic treatment of multiple sclerosis in a patient, and to identify a compound suitable for the treatment of multiple sclerosis in a patient. Furthermore, the invention relates to a kit for determining whether a patient responds to a therapeutic treatment of multiple sclerosis, for monitoring the course of multiple sclerosis in a patient, for determining the risk of a relapse of multiple sclerosis in a patient, for adjusting the dose of a therapeutic drug applied for therapeutic treatment of multiple sclerosis in a patient, or for identifying a compound suitable for the treatment of multiple sclerosis in a patient comprising means for determining the level of at least one miRNA in a test sample isolated from a patient.

BACKGROUND OF THE INVENTION

Multiple Sclerosis (MS) is the most common chronic inflammatory disease of the central nervous system (CNS) in the Western world and a major cause of sustained neurological disability of young adults (Compston A, Coles A. Multiple sclerosis. Lancet 2002; 359:1221-1231). The disease is characterized by destruction of myelin, associated with death of oligodendrocytes and axonal loss. One of the mechanistic hallmarks of the disease is the influx of activated T lymphocytes and other immune cells from the blood stream into brain tissue, thereby passing the blood brain barrier (BBB) (Engelhardt B, Ransohoff R M. The ins and outs of T-lymphocyte trafficking to the CNS: anatomical sites and molecular mechanisms. Trends Immunol 2005; 26:485-495). Regarding the underlying molecular mechanisms, antibodies binding α4-integrin and, thus, blocking the α4β1 dimer on T lymphocytes were shown to prevent the intrusion of immune cells into the brain in an animal model of MS, experimental autoimmune encephalomyelitis (EAE) (Yednock T A, Cannon C, Fritz L C et al. Prevention of Experimental Autoimmune Encephalomyelitis by Antibodies Against Alpha-4-Beta-1 Integrin. Nature 1992; 356:63-66 and Baron J L, Madri J A, Ruddle N H et al. Surface expression of alpha 4 integrin by CD4 T cells is required for their entry into brain parenchyma. J Exp Med 1993; 177: 57-68). The neurological symptoms that characterize MS include complete or partial vision loss, diplopia, sensory symptoms, motor weakness that can worsen to complete paralysis, bladder dysfunction and cognitive deficits, which eventually may lead to a significant disability. The associated multiple inflammatory foci lead to myelin destruction, plaques of demyelination, gliosis and axonal loss within the brain and spinal cord and are the reasons contribute to the clinical manifestations of neurological disability.

There are a number of drugs known which are used in the treatment of MS. Monthly infusions of natalizumab (Tysabri®), for example, were shown to profoundly reduce the risk of relapses in MS (Polman C H, O'Connor P W, Havrdova E et al. A randomized, placebo-controlled trial of natalizumab for relapsing multiple sclerosis. New England Journal of Medicine 2006; 354:899-910) and represent a powerful therapy option in MS.

Natalizumab is a humanized monoclonal antibody against the cellular adhesion molecule α4-integrin. The drug works by reducing the ability of inflammatory immune cells to attach to and pass through the cell layers lining the intestines and blood-brain barrier. Natalizumab has proven effective in treating the symptoms of MS, preventing relapse, vision loss, cognitive decline and significantly improving quality of life in people with multiple sclerosis. It is, however, also associated with the potentially lethal adverse effects, namely the JC virus infection of the CNS, progressive multifocal encephalopathy (PML).

Monitoring of MS is necessary in order to evaluate the course of said disease. Monitoring of MS treatment is also very important in order to evaluate the efficacy or non-efficacy of a drug application. However, MS or the treatment of MS is often difficult to monitor in human patients with less capacity to communicate, e.g. mentally disabled persons. In addition, animals as patients can not speak and only communicate in an acoustical language (if at all). Further, there is often difficulty of objectively monitoring and staging MS as even descriptions of persons able to describe their symptoms are subjective. Furthermore, neurophysiological examinations are very time consuming. In addition, imaging examinations such as magnetic resonance imaging to evaluate the outcome of a MS therapy are very expensive. Moreover, before a successful MS therapy is visible on a physiological level time passes. This is problematic as drugs for MS therapy are very expensive.

Thus, there is a need for new, alternative ways of monitoring MS, particularly MS treatment, which are independent from the patient's reasoning. There is also a need for easy, save and fast methods for determining whether patients respond to a therapeutic treatment of MS or not and methods for adjusting the dose of drugs applied for treating MS in patients. Further, methods which allow the prediction of a single patient's potential risk, for example, to experience a relapse in MS, are highly desirable.

Today, biomarkers such as microRNAs (miRNAs) play a key role in early diagnosis, monitoring, risk stratification, and therapeutic management of various diseases. MiRNAs are small 15 to 27 nucleotide non-coding, highly preserved RNA molecules that recently emerged as key epigenetic regulators in a plethora of cellular pathways (Ambros V. The functions of animal microRNAs. Nature 2004; 431:350-355 and Bartel D P. MicroRNAs: Genomics, biogenesis, mechanism, and function. Cell 2004; 116:281-297). Utilizing a specialized molecular machinery, they bind complementarily to the 3' UTR of a messenger RNA, thus preventing it from translation and leading to its degradation. It is estimated that at least a third of all genes are post-transcriptionally regulated in a miRNA-dependent manner (Lewis B P, Burge C B, Bartel D P. Conserved seed pairing, often flanked by adenosines, indicates that thousands of human genes are microRNA targets. Cell 2005; 120:15-20). Some miRNAs are genomically organized as a cluster, meaning a certain number of miRNAs are transcribed simultaneously. Other miRNAs have very similar sequences and overlapping functions and are often grouped together in miRNAs families. Increasing evidence shows that miRNAs play an indispensable role in immune functions and mechanisms of autoimmunity (Baltimore D, Boldin M P, O'Connell R M et al. MicroRNAs: new regulators of immune cell development and function. Nature Immunology 2008; 9:839-845). Indeed, cross-sectional studies investigating the peripheral blood (Otaegui D, Baranzini S E, Armananzas R et al. Differential Micro RNA Expression in PBMC from Multiple Sclerosis Patients. Plos One 2009; 4; Keller A, Leidinger P, Lange J et al. Multiple sclerosis: microRNA expression profiles accurately differentiate patients with relapsing-remitting disease from healthy controls. PLoS One 2009; 4:e7440; Lindberg R L P, Hoffmann F, Mehling M et al. Altered expression of miR-17-5p in CD4(+) lymphocytes of relapsing-remitting multiple sclerosis patients. European Journal of Immunology 2010; 40:888-898; Cox M B, Cairns M J, Gandhi K S et al. MicroRNAs miR-17 and miR-20a Inhibit T Cell Activation Genes and Are Under-Expressed in MS Whole Blood. Plos One 2010; 5; De S G, Ferracin M, Biondani A et al. Altered miRNA expression in T regulatory cells in course of multiple sclerosis. J Neuroimmunol 2010; 226:165-171; Guerau-de-Arellano M, Smith K M, Godlewski J et al. Micro-RNA dysregulation in multiple sclerosis favours pro-inflammatory T-cell-mediated autoimmunity. Brain 2011) or inflammatory CNS lesions (Junker A, Krumbholz M, Eisele S et al. MicroRNA profiling of multiple sclerosis lesions identifies modulators of the regulatory protein CD47. Brain 2009; 132:3342-3352) showed dysregulated miRNA patterns in MS.

The inventors of the present invention assessed the expression of miRNAs in patients suffering from relapsing-remitting multiple sclerosis (RR-MS). They identified new miRNAs which are deregulated between RR-MS patients and healthy controls. Said miRNAs allow monitoring of MS, particularly RR-MS. Using a combined longitudinal and cross-sectional approach in RR-MS and confirmatory animal experiments, the inventors of the present invention found that the drug natalizumab has an impact on several miRNAs in RR-MS patients. Said miRNAs allow the monitoring of MS treatment, particularly RR-MS treatment. In particular, said miRNAs represent novel targets for drug response monitoring. Moreover, said miRNAs are tools for the identification of new compounds suitable for the treatment of multiple sclerosis, particularly RR-MS.

SUMMARY OF THE INVENTION

In a first aspect, the invention provides a method of determining whether a patient responds to a therapeutic treatment of multiple sclerosis (MS) comprising the step of: determining the level of at least one miRNA in a test sample isolated from the patient, wherein the nucleotide sequence of the at least one miRNA is selected from the group consisting of SEQ ID NO: 1 to SEQ ID NO: 15, a fragment thereof, and a sequence having at least 80% sequence identity thereto.

In a second aspect, the invention provides a method of monitoring the course of multiple sclerosis (MS) in a patient comprising the step of:
determining the level of at least one miRNA in a test sample isolated from the patient, wherein the nucleotide sequence of the at least one miRNA is selected from the group consisting of SEQ ID NO: 1 to SEQ ID NO: 15, a fragment thereof, and a sequence having at least 80% sequence identity thereto.

In a third aspect, the invention provides a method of determining the risk for a relapse of multiple sclerosis (MS) in a patient comprising the step of:
determining the level of at least one miRNA in a test sample isolated from the patient, wherein the nucleotide sequence of the at least one miRNA is selected from the group consisting of SEQ ID NO: 1 to SEQ ID NO: 15, a fragment thereof, and a sequence having at least 80% sequence identity thereto.

In a fourth aspect, the invention provides a method of adjusting the dose of a therapeutic drug applied for therapeutic treatment of multiple sclerosis in a patient comprising the step of:
determining the level of at least one miRNA in a test sample isolated from the patient, wherein the nucleotide sequence of the at least one miRNA is selected from the group consisting of SEQ ID NO: 1 to SEQ ID NO: 15, a fragment thereof, and a sequence having at least 80% sequence identity thereto.

In a fifth aspect, the invention provides a method of identifying a compound suitable for the treatment of multiple sclerosis in a patient comprising the steps of:
(i) providing a test system comprising at least one miRNA, wherein the nucleotide sequence of the at least one miRNA is selected from the group consisting of SEQ ID NO: 1 to SEQ ID NO: 15, a fragment thereof, and a sequence having at least 80% sequence identity thereto,
(ii) contacting the test system with a test compound, and
(iii) determining the effect of the test compound on the test system,
wherein the test compound is identified as a compound suitable for the treatment of multiple sclerosis in the patient, when a significant effect of the test compound on the test system relative to a control is detected.

In a sixth aspect, the invention provides the use of a polynucleotide for detecting a miRNA to determine whether a patient responds to a therapeutic treatment of multiple sclerosis, to monitor the course of multiple sclerosis in a patient, to determine the risk of a relapse of multiple sclerosis in a patient, to adjust the dose of a therapeutic drug applied for therapeutic treatment of multiple sclerosis in a patient, or to identify a compound suitable for the treatment of multiple sclerosis in a patient, wherein the nucleotide sequence of the miRNA is selected from the group consisting of SEQ ID NO: 1 to SEQ ID NO: 15.

In a seventh aspect, the invention provides the use of a polynucleotide set comprising at least two different polynucleotides according to the sixth aspect for detecting at least two different miRNAs to determine whether a patient responds to a therapeutic treatment of multiple sclerosis, to monitor the course of multiple sclerosis in a patient, to determine the risk of a relapse of multiple sclerosis in a patient, to adjust the dose of a therapeutic drug applied for therapeutic treatment of multiple sclerosis in a patient, or to identify a compound suitable for the treatment of multiple sclerosis in a patient.

In an eighth aspect, the invention provides a kit for determining whether a patient responds to a therapeutic treatment of multiple sclerosis, for monitoring the course of multiple sclerosis in a patient, for determining the risk of a relapse of multiple sclerosis in a patient, for adjusting the dose of a therapeutic drug applied for therapeutic treatment of multiple sclerosis in a patient, or for identifying a compound suitable for the treatment of multiple sclerosis in a patient comprising means for determining the level of at least one miRNA in a test sample isolated from a patient, wherein the nucleotide sequence of the at least one miRNA is selected from the group consisting of SEQ ID NO: 1 to SEQ ID NO: 15, a fragment thereof, and a sequence having at least 80% sequence identity thereto.

In a ninth aspect, the invention provides natalizumab for use in the treatment of patients suffering from multiple sclerosis, wherein the patients are characterized by a decreased level of at least one miRNA, wherein the nucleotide sequence of the at least one miRNA is selected from the group consisting of SEQ ID NO: 1 to SEQ ID NO: 4, a fragment thereof, and a sequence having at least 80% sequence identity thereto, and/or an increased level of a miRNA, wherein the nucleotide sequence of the miRNA is SEQ ID NO: 9, a fragment thereof, or a sequence having at least 80% sequence identity thereto compared to healthy controls.

This summary of the invention does not necessarily describe all features of the invention.

DETAILED DESCRIPTION OF THE INVENTION

Before the present invention is described in detail below, it is to be understood that this invention is not limited to the particular methodology, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art.

In the following, the elements of the present invention will be described. These elements are listed with specific embodiments, however, it should be understood that they may be combined in any manner and in any number to create additional embodiments. The variously described examples and preferred embodiments should not be construed to limit the present invention to only the explicitly described embodiments. This description should be understood to support and encompass embodiments which combine the explicitly described embodiments with any number of the disclosed and/or preferred elements. Furthermore, any permutations and combinations of all described elements in this application should be considered disclosed by the description of the present application unless the context indicates otherwise.

Preferably, the terms used herein are defined as described in "A multilingual glossary of biotechnological terms: (IUPAC Recommendations)", H. G. W. Leuenberger, B. Nagel, and H. Kölbl, Eds., Helvetica Chimica Acta, CH-4010 Basel, Switzerland, (1995).

To practice the present invention, unless otherwise indicated, conventional methods of chemistry, biochemistry, and recombinant DNA techniques are employed which are explained in the literature in the field (cf., e.g., *Molecular Cloning: A Laboratory Manual*, 2$^{nd}$ Edition, J. Sambrook et al. eds., Cold Spring Harbor Laboratory Press, Cold Spring Harbor 1989).

Several documents are cited throughout the text of this specification. Each of the documents cited herein (including all patents, patent applications, scientific publications, manufacturer's specifications, instructions, etc.), whether supra or infra, are hereby incorporated by reference in their entirety. Nothing herein is to be construed as an admission that the invention is not entitled to antedate such disclosure by virtue of prior invention.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

As used in this specification and in the appended claims, the singular forms "a", "an", and "the" include plural referents, unless the content clearly dictates otherwise. For example, the term "a test compound" also includes "test compounds".

The terms "microRNA" or "miRNA" refer to single-stranded RNA molecules of at least 10 nucleotides and of not more than 35 nucleotides covalently linked together. Preferably, the polynucleotides of the present invention are molecules of 10 to 33 nucleotides or 15 to 30 nucleotides in length, more preferably of 17 to 27 nucleotides or 18 to 26 nucleotides in length, e.g. 10, 11, 12, 13, 14, 15, 16, 17, 18, 19, 20, 21, 22, 23, 24, 25, 26, 27, 28, 29, 30, 31, 32, 33, 34, or 35 nucleotides in length, not including optionally labels and/or elongated sequences (e.g. biotin stretches). The miRNAs regulate gene expression and are encoded by genes from whose DNA they are transcribed but miRNAs are not translated into protein (i.e. miRNAs are non-coding RNAs). The genes encoding miRNAs are longer than the processed mature miRNA molecules. The miRNAs are first transcribed as primary transcripts or pri-miRNAs with a cap and poly-A tail and processed to short, 70 nucleotide stem-loop structures known as pre-miRNAs in the cell nucleus. This processing is performed in animals by a protein complex known as the Microprocessor complex consisting of the nuclease Drosha and the double-stranded RNA binding protein Pasha. These pre-miRNAs are then processed to mature miRNAs in the cytoplasm by interaction with the endonuclease Dicer, which also initiates the formation of the RNA-induced silencing complex (RISC). When Dicer cleaves the pre-miRNA stem-loop, two complementary short RNA molecules are formed, but only one is integrated into the RISC. This strand is known as the guide strand and is selected by the argonaute protein, the catalytically active RNase in the RISC, on the basis of the stability of the 5' end. The remaining strand, known as the miRNA*, anti-guide (antistrand), or passenger strand, is degraded as a RISC substrate. Therefore, the miRNA*s are derived from the same hairpin structure like the "normal" miRNAs. So if the "normal" miRNA is then later called the "mature miRNA" or "guide strand", the miRNA* is the "anti-guide strand" or "passenger strand".

The terms "microRNA*" or "miRNA*" refer to single-stranded RNA molecules of at least 10 nucleotides and of not more than 35 nucleotides covalently linked together. Preferably, the polynucleotides of the present invention are molecules of 10 to 33 nucleotides or 15 to 30 nucleotides in length, more preferably of 17 to 27 nucleotides or 18 to 26 nucleotides in length, e.g. 10, 11, 12, 13, 14, 15, 16, 17, 18, 19, 20, 21, 22, 23, 24, 25, 26, 27, 28, 29, 30, 31, 32, 33, 34, or 35 nucleotides in length, not including optionally labels and/or elongated sequences (e.g. biotin stretches). The "miRNA*s", also known as the "anti-guide strands" or "passenger strands", are mostly complementary to the "mature miRNAs" or "guide strands", but have usually single-stranded overhangs on each end. There are usually one or more mispairs and there are sometimes extra or missing bases causing single-stranded "bubbles". The miRNA*s are likely to act in a regulatory fashion as the miRNAs (see also above). In the context of the present invention, the terms "miRNA" and "miRNA*" are interchangeable used. The present invention encompasses (target) miRNAs selected from the group consisting of SEQ ID NO: 1 to SEQ ID NO: 15.

The term "miRBase" refers to a well established repository of validated miRNAs. The miRBase (www.mirbase.org) is a searchable database of published miRNA sequences and annotation. Each entry in the miRBase Sequence database represents a predicted hairpin portion of a miRNA transcript (termed mir in the database), with information on the location and sequence of the mature miRNA sequence (termed miR). Both hairpin and mature sequences are available for searching and browsing, and entries can also be retrieved by name, keyword, references and annotation. All sequence and annotation data are also available for download. The miRNAs selected from the group consisting of SEQ ID NO: 1 to SEQ ID NO: 15 are based on miRBase version 12.

As used herein, the term "nucleotides" refers to structural components, or building blocks, of DNA and RNA. Nucleotides consist of a base (one of four chemicals: adenine, thymine, guanine, and cytosine) plus a molecule of sugar and one of phosphoric acid. The term "nucleosides" refers to glycosylamine consisting of a nucleobase (often referred to simply base) bound to a ribose or deoxyribose sugar. Examples of nucleosides include cytidine, uridine, adenosine, guanosine, thymidine and inosine. Nucleosides can be phosphorylated by specific kinases in the cell on the sugar's primary alcohol group (—CH2-OH), producing nucleotides, which are the molecular building blocks of DNA and RNA.

The term "polynucleotide", as used herein, means a molecule of at least 10 nucleotides and of not more than 35 nucleotides covalently linked together. Preferably, the polynucleotides of the present invention are molecules of 10 to 33 nucleotides or 15 to 30 nucleotides in length, more preferably of 17 to 27 nucleotides or 18 to 26 nucleotides in length, e.g. 10, 11, 12, 13, 14, 15, 16, 17, 18, 19, 20, 21, 22, 23, 24, 25, 26, 27, 28, 29, 30, 31, 32, 33, 34, or 35 nucleotides in length, not including optionally spacer elements and/or elongation elements described below. The depiction of a single strand of a polynucleotide also defines the sequence of the complementary strand. Polynucleotides may be single stranded or double stranded, or may contain portions of both double stranded and single stranded sequences. The term "polynucleotide" means a polymer of deoxyribonucleotide or ribonucleotide bases and includes DNA and RNA molecules, both sense and anti-sense strands. In detail, the polynucleotide may be DNA, both cDNA and genomic DNA, RNA, cRNA or a hybrid, where the polynucleotide sequence may contain combinations of deoxyribonucleotide or ribonucleotide bases, and combinations of bases including uracil, adenine, thymine, cytosine, guanine, inosine, xanthine, hypoxanthine, isocytosine and isoguanine. Polynucleotides may be obtained by chemical synthesis methods or by recombinant methods.

In the context of the present invention, a polynucleotide as a single polynucleotide strand provides a probe (e.g. miRNA capture probe) that is capable of binding to, hybridizing with, or detecting a target of complementary sequence, such as a nucleotide sequence of a miRNA or miRNA*, through one or more types of chemical bonds, usually through complementary base pairing, usually through hydrogen bond formation. Polynucleotides in their function as probes may bind target sequences, such as nucleotide sequences of miRNAs or miRNAs*, lacking complete complementarity with the polynucleotide sequences depending upon the stringency of the hybridization condition. There may be any number of base pair mismatches which will interfere with hybridization between the target sequence, such as a nucleotide sequence of a miRNA or miRNA*, and the single stranded polynucleotide described herein. However, if the number of mutations is so great that no hybridization can occur under even the least stringent hybridization conditions, the sequences are no complementary sequences. The present invention encompasses polynucleotides in form of single polynucleotide strands as probes for binding to, hybridizing with or detecting complementary sequences of (target) miRNAs selected from the group consisting of SEQ ID NO: 1 to SEQ ID NO: 15.

The polynucleotide, e.g. the polynucleotide used as a probe for detecting a miRNA or miRNA*, may be unlabeled, directly labeled, or indirectly labeled, such as with biotin to which a streptavidin complex may later bind. The polynucleotide, e.g. the polynucleotide used as a probe for detecting a miRNA or miRNA*, may also be modified, e.g. may comprise an elongation (EL) element. For use in a RAKE or MPEA assay, a polynucleotide with an elongation element may be used as a probe. The elongation element comprises a nucleotide sequence with 1 to 30 nucleotides chosen on the basis of showing low complementarity to potential target sequences, such as nucleotide sequences of miRNAs or miRNAs*, therefore resulting in no or a low degree of cross-hybridization to a target mixture. In one embodiment of the invention, a homomeric sequence stretch $N_n$ with n=1 to 30, e.g. 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30, and N=A or C, or T or G is preferred. Particularly preferred is a homomeric sequence stretch $N_n$ with n=1 to 12, e.g. 1, 2, 3, 4, 5, 6, 7, 8, 9, 10, 11, or 12, and N=A or C, or T or G. The polynucleotide, e.g. the polynucleotide used as a probe for detecting a miRNA or miRNA*, may be present in form of a tandem, i.e. in form of a polynucleotide hybrid of two different or identical polynucleotides, both in the same orientation, e.g. 5' to 3' or 3' to 5', or in different orientation, e.g. 5' to 3' and 3' to 5'. Said polynucleotide hybrid/tandem may comprise a spacer element. For use in a tandem hybridization assay, the polynucleotide hybrid/tandem as a probe may comprise a spacer (SP) element. The spacer element represents a nucleotide sequence with n=0 to 12, e.g. 0, 1, 2, 3, 4, 5, 6, 7, 8, 9, 10, 11, or 12, nucleotides chosen on the basis of showing low complementarity to potential target sequences, such as nucleotide sequences of miRNAs or anti-miRNAs, therefore resulting in no or a low degree of cross-hybridization to a target mixture. It is preferred that n is 0, i.e. that there is no spacer between the two miRNA sequence stretches. In another embodiment of the invention, a non-homomeric sequence stretch $N_n$ with n=1 to 30, e.g. 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30, and N=A or C, or T or G is preferred. Particularly preferred is a non-homomeric sequence stretch that can be used as a priming site for a polymerase for a downstream amplification reaction.

For detection purposes, the miRNA(s) or miRNA*(s) may be employed unlabeled, directly labeled, or indirectly labeled, such as with biotin to which a streptavidin complex may later bind.

The term "label", as used herein, means a composition detectable by spectroscopic, photochemical, biochemical, immunochemical, chemical, or other physical means. For example, useful labels include 32P, fluorescent dyes, electron-dense reagents, enzymes (e.g., as commonly used in an ELISA), biotin, digoxigenin, or haptens and other entities which are or can be made detectable. A label may be incorporated into nucleic acids at any position, e.g. at the 3' or 5' end or internally. The polynucleotide for detecting a miRNA (polynucleotide probe) and/or the miRNA itself may be labeled.

The term "stringent hybridization conditions", as used herein, means conditions under which a first nucleotide sequence (e.g. polynucleotide in its function as a probe for detecting a miRNA or miRNA*) will hybridize to a second nucleotide sequence (e.g. target sequence such as nucleotide sequence of a miRNA or miRNA*), such as in a complex mixture of nucleotide sequences. Stringent conditions are sequence-dependent and will be different in different circumstances. Stringent conditions may be selected to be about 5 to 10° C. lower than the thermal melting point (Tm) for the specific sequence at a defined ionic strength, pH. The Tm may be the temperature (under defined ionic strength, pH, and nucleic acid concentration) at which 50% of the probes complementary to the target hybridize to the target sequence at equilibrium (as the target sequences are present in excess, at Tm, 50% of the probes are occupied at equilibrium). Stringent conditions may be those in which the salt concentration is less than about 1.0 M sodium ion, such as about 0.01 to 1.0 M sodium ion concentration (or other salts) at pH 7.0 to 8.3 and the temperature is at least about 20° C. for short probes (e.g. about 10-35 nucleotides) and up to 60° C. for long probes (e.g. greater than about 50 nucleotides). Stringent conditions may also be achieved with the addition of destabilizing agents such as formamide. For selective or specific hybridization, a positive signal may be at least 2 to 10 times background hybridization. Exemplary stringent hybridization conditions include the following: 50% formamide, 5×SSC, and 1% SDS, incubating at 42° C., or, 5×SSC, 1% SDS, incubating at 65° C., with wash in 0.2×SSC, and 0.1% SDS at 65° C.; or 6×SSPE, 10% formamide, 0.01%, Tween 20, 0.1×TE buffer, 0.5 mg/ml BSA, 0.1 mg/ml herring sperm DNA, incubating at 42° C. with wash in 0.5×SSPE and 6×SSPE at 45° C.

The term "antisense", as used herein, refers to nucleotide sequences which are complementary to a specific DNA or RNA sequence. The term "antisense strand" is used in reference to a nucleic acid strand that is complementary to the "sense" strand.

The term "multiple sclerosis (MS)", as used herein, refers to an inflammatory demyelinating disease of the central nervous system (CNS). MS is characterized by destruction of myelin, associated with death of oligodendrocytes and axonal loss. The main pathologic finding in MS is the presence of infiltrating mononuclear cells, predominantly T lymphocytes and macrophages, which surpass the blood brain barrier (BBB) and induce an active inflammation within the brain and spinal cord. The neurological symptoms that characterize MS include, but are not limited to, complete or partial vision loss, diplopia, sensory symptoms, motor weakness that can worsen to complete paralysis, bladder dysfunction and cognitive deficits, which eventually may lead to a significant disability. The associated multiple inflammatory foci can lead to myelin destruction, plaques of demyelination, gliosis and axonal loss within the brain and spinal cord. These are the reasons which contribute to the clinical manifestations of neurological disability. There are four main varieties of multiple sclerosis, as defined in an international survey of neurologists (Lublin and Reingold, 1996): relapsing-remitting multiple sclerosis (RR-MS), secondary progressive multiple sclerosis (SP-MS), progressive relapsing multiple sclerosis (PR-MS), and primary progressive multiple sclerosis (PP-MS).

The term "relapsing-remitting multiple sclerosis (RR-MS)", as used herein, refers to a MS disease which is characterized by relapses (also known as exacerbations) during which new symptoms can appear and old ones resurface or worsen. The relapses are followed by periods of remission, during which the person fully or partially recovers from the deficits acquired during the relapse. Relapses can last for days, weeks or months and recovery can be slow and gradual or almost instantaneous. This describes the initial course of 80% of patients with MS.

The term "secondary progressive multiple sclerosis (SPMS) (sometimes called "galloping MS")", as used herein, describes around 65% of those with an initial relapsing-remitting multiple sclerosis (RR-MS), who then begin to have progressive neurologic decline between acute attacks without any definite periods of remission. Occasional relapses and minor remissions may appear. The median time between disease onset and conversion from relapsing-remitting to secondary progressive MS is about 19 years.

The term "progressive relapsing multiple sclerosis (PRMS)", as used herein, refers to a form of MS which follows a progressive course from onset, punctuated by relapses. There is significant recovery immediately following a relapse but between relapses there is a gradual worsening of symptoms.

The term "primary progressive multiple sclerosis (PPMS)", as used herein, is characterised by a gradual progression of the disease from its onset with no remissions at all. The primary progressive subtype describes the approximately 10-15% of patients who never have remission after their initial MS symptoms.

The term "multiple sclerosis (MS)", as used herein, also covers atypical variants of MS with non-standard behaviour. These variants of MS include, but are not limited to, Devic's disease, Balo concentric sclerosis, Schilder's diffuse sclerosis and Marburg multiple sclerosis.

The inventors of the present invention assessed the expression of miRNAs in patients suffering from relapsing-remitting multiple sclerosis (RR-MS). They identified new miRNAs which are deregulated between RR-MS patients and healthy controls. Said miRNAs allow monitoring of MS, particularly RR-MS. Using a combined longitudinal and cross-sectional approach in RR-MS and confirmatory animal experiments, the inventors of the present invention found that the drug natalizumab has an impact on several miRNAs in RR-MS patients. Said miRNAs allow the monitoring of MS treatment, particularly RR-MS treatment. In particular, said miRNAs represent novel targets for drug response monitoring. Moreover, said miRNAs are tools for the identification of new compounds suitable for the treatment of multiple sclerosis, particularly RR-MS.

Thus, in a first aspect, the invention relates to a method of determining whether a patient responds to a therapeutic treatment of multiple sclerosis (MS) comprising the step of: determining the level of at least one miRNA, e.g. 1, 2, 3, 4, 5, 6, 7, 8, 9, 10, 11, 12, 13, 14, or 15 miRNA(s), in a test sample isolated from the patient, wherein the nucleotide sequence of the at least one miRNA is selected from the group consisting of SEQ ID NO: 1 to SEQ ID NO: 15, a fragment thereof, and a sequence having at least 80% sequence identity thereto.

It is preferred that the level of the nucleotide sequence of the miRNA having SEQ ID NO: 1, SEQ ID NO: 2, SEQ ID NO: 3, SEQ ID NO: 4, SEQ ID NO: 9, a fragment thereof, or a sequence having at least 80% sequence identity thereto is determined. It is particularly preferred that the level of the nucleotide sequence of the miRNA having SEQ ID NO: 1, SEQ ID NO: 2, a fragment thereof, or a sequence having at least 80% sequence identity thereto is determined.

In an alternative embodiment, the level of the nucleotide sequence of the miRNA having SEQ ID NO: 3, a fragment thereof, or a sequence having at least 80% sequence identity thereto, and/or the level of the nucleotide sequence of the miRNA having SEQ ID NO: 9, a fragment thereof, or a sequence having at least 80% sequence identity thereto is not determined.

It is further preferred that the level of the nucleotide sequences of the miRNAs having SEQ ID NO: 1 to SEQ ID NO: 15, fragments thereof, or sequences having at least 80% sequence identity thereto is determined. It is particularly preferred that the level of the nucleotide sequences of the miRNAs having SEQ ID NO: 1 to SEQ ID NO: 8, fragments thereof, or sequences having at least 80% sequence identity thereto is determined or that the level of the nucleotide sequences of the miRNAs having SEQ ID NO: 9 to SEQ ID NO: 15, fragments thereof, or sequences having at least 80% sequence identity thereto is determined. It is more preferred that the level of the nucleotide sequences of the miRNAs having SEQ ID NO: 1 to SEQ ID NO: 4 and SEQ ID NO: 9, fragments thereof, or sequences having at least 80% sequence identity thereto is determined. It is particularly more preferred that the level of the nucleotide sequences of the miRNAs having SEQ ID NO: 1 to SEQ ID NO: 4, fragments thereof, or sequences having at least 80% sequence identity thereto is determined. It is most preferred that the level of the nucleotide sequences of the miRNAs having (i) SEQ ID NO: 1 and SEQ ID NO: 2, fragments thereof, or sequence having at least 80% sequence identity thereto, (ii) SEQ ID NO: 1 and SEQ ID NO: 3, fragments thereof, or sequences having at least 80% sequence identity thereto, (iii) SEQ ID NO: 1 and SEQ ID NO: 4, fragments thereof, or sequences having at least 80% sequence identity thereto, (iv) SEQ ID NO: 2 and SEQ ID NO: 3, fragments thereof, or sequences having at least 80% sequence identity thereto, (v) SEQ ID NO: 2 and SEQ ID NO: 4, fragments thereof, or sequences having at least 80% sequence identity thereto, or (vi) SEQ ID NO: 3 and SEQ ID NO: 4, fragments thereof, or sequences having at least 80% sequence identity thereto is determined.

In case of the miRNA having a nucleotide sequence according to SEQ ID NO: 3, a fragment thereof, or a sequence having at least 80% sequence identity thereto, it is preferred that the level of this miRNA is only determined together with the level of at least one further miRNA having a nucleotide sequence selected from the group consisting of SEQ ID NO: 1, SEQ ID NO: 2, SEQ ID NO: 4 to SEQ ID NO: 15, a fragment thereof, and a sequence having at least 80% sequence identity thereto, particularly selected from the group consisting of SEQ ID NO: 1, SEQ ID NO: 2, SEQ ID NO: 4 to SEQ ID NO: 8, SEQ ID NO: 10 to SEQ ID NO: 15, a fragment thereof, and a sequence having at least 80% sequence identity thereto, or in case of the miRNA having a nucleotide sequence according to SEQ ID NO: 9, a fragment thereof, or a sequence having at least 80% sequence identity thereto, it is preferred that the level of this miRNA is only determined together with the level of at least one further miRNA having a nucleotide sequence selected from the group consisting of SEQ ID NO: 1 to SEQ ID NO: 8, SEQ ID NO: 10 to SEQ ID NO: 15, a fragment thereof, and a sequence having at least 80% sequence identity thereto, particularly selected from the group consisting of SEQ ID NO: 1, SEQ ID NO: 2, SEQ ID NO: 4 to SEQ ID NO: 8, SEQ ID NO: 10 to SEQ ID NO: 15, a fragment thereof, and a sequence having at least 80% sequence identity thereto. In addition, in case of miRNAs having nucleotide sequences according to SEQ ID NO: 3, SEQ ID NO: 9, a fragment thereof, or a sequence having at least 80% sequence identity thereto, it is preferred that the level of these miRNA is only determined together with the level of at least one further miRNA having a nucleotide sequence selected from the group consisting of SEQ ID NO: 1, SEQ ID NO: 2, SEQ ID NO: 4 to SEQ ID NO: 8, SEQ ID NO: 10 to SEQ ID NO: 15, a fragment thereof, and a sequence having at least 80% sequence identity thereto. Other preferred miRNA combinations are listed in FIG. 8.

The term "test sample", as used herein, refers to any biological sample containing (a) miRNA(s), particularly containing (a) miRNA(s) with (a) nucleotide sequence(s) according to SEQ ID NO: 1 to SEQ ID NO: 15, a fragment thereof, or a sequence having at least 80% sequence identity thereto. Said test sample may be a body fluid sample, a tissue sample, or a cell sample. For example, test samples encompassed by the present invention are tissue (e.g. section or explant) samples, single cell samples, cell colony samples, cell culture samples, blood (e.g. whole blood or blood fraction such as blood cell fraction, serum or plasma) samples, urine samples, or samples from other peripheral sources. Said test samples may be mixed or pooled, e.g. a test sample may be a mixture of a blood sample and an urine sample. A "test sample" may be provided by removing a body fluid, cell(s), cell colonies, an explant, or a section from a patient, but may also be provided by using a previously isolated sample. For example, a tissue sample may be removed from a patient by conventional biopsy techniques or a blood sample may be taken from a patient by conventional blood collection techniques. The test sample, e.g. tissue sample or blood sample, may be obtained from a patient prior to initiation of the therapeutic treatment, during the therapeutic treatment, and/or after the therapeutic treatment. It is also preferred that total RNA or a subfraction thereof, isolated (e.g. extracted) from a test sample of a patient (e.g. human or rodent), is used.

Preferably, the test sample is a body fluid sample, a tissue sample, a cell colony sample, a single cell sample or a cell culture sample. Said test samples may be mixed or pooled, e.g. the test sample may be a mixture of a body fluid sample and a tissue sample or a mixture of a body fluid sample and a cell culture sample. More preferably, the tissue sample is a section or an explant sample.

It is preferred that the tissue sample has a weight of between 0.1 and 500 mg, more preferably of between 0.5 and 250 mg, and most preferably of between 1 and 50 mg, e.g. 0.1, 0.2, 0.3, 0.4, 0.5, 0.6, 0.7, 0.8, 0.9, 1, 2, 2.5, 3, 4, 5, 6, 7, 8, 9, 10, 15, 20, 25, 30, 35, 40, 45, 50, 55, 60, 65, 70, 75, 80, 85, 90, 95, 100, 125, 150, 175, 200, 225, 250, 275, 300, 325, 350, 375, 400, 425, 450, 475, or 500 mg.

It is also preferred that the cell sample (e.g. cell colony sample or cell culture sample) from a patient (e.g. human or rodent) consists of between $10^2$ and $10^{10}$ cells, more preferably of between $10^3$ and $10^7$ cells, and most preferably of between $10^4$ and $10^6$ cells, e.g. $10^2$, $10^3$, $10^4$, $10^5$, $10^6$, $10^7$, $10^8$, $10^9$, or $10^{10}$ cells.

A body fluid sample is a liquid sample derived from the body of a patient, e.g. human or rodent. Said body fluid sample may be a blood sample, urine sample, sputum sample, breast milk sample, cerebrospinal fluid (CSF) sample, cerumen (earwax) sample, endolymph sample, perilymph sample, gastric juice sample, mucus sample, peritoneal fluid sample, pleural fluid sample, saliva sample, sebum (skin oil) sample, semen sample, sweat sample, tears sample, vaginal secretion sample, or vomit sample including components or fractions thereof. Said body fluid samples may be mixed or pooled. Thus, a body fluid sample may be a mixture of a blood and an urine sample or a mixture of a blood and cerebrospinal fluid sample. A body fluid sample may be provided by removing a body liquid from a patient, but may also be provided by using previously isolated body fluid sample material. Said "body fluid sample" allows for a non-invasive analysis of a patient, e.g. human or rodent.

It is further preferred that the body fluid sample has a volume of between 0.01 and 20 ml, more preferably of between 0.1 and 10 ml, more preferably between 0.5 and 8 ml and most preferably between 1 and 5 ml, e.g. 0.01, 0.05, 0.1, 0.2, 0.3, 0.4, 0.5, 0.6, 0.7, 0.8, 0.9, 1, 2, 2.5, 3, 4, 5, 6, 7, 8, 9, 10, 11, 12, 13, 14, 15, 16, 17, 18, 19, or 20 ml.

More preferably, the body fluid sample is a blood sample, an urine sample, or a cerebrospinal fluid (CSF) sample, or mixtures thereof.

Most preferably, the blood sample is whole blood or a blood fraction sample such as a blood cell fraction, serum or plasma sample. It is particularly preferred to use blood cells also known as hemopoietic cells. Hemopoietic cells are mature cell types and their immature precursors are identifiable either by morphology or, mostly, by a distinct pattern of cell surface markers. Said term is used to distinguish these cells from other cell types found in the body and also includes T-cells and distinctive subsets, which are the only hematopoietic cells that are not generated in the bone marrow. Said blood cells may be erythrocytes, leukocytes, and/or thrombocytes, e.g. mixtures thereof. For example, the blood cell sample may be an erythrocyte, a leukocyte and/or a thrombocyte containing sample. Peripheral blood mononuclear cells (PBMCs) such as lymphocytes, monocytes or macrophages may also be used.

It is preferred that the blood sample has a volume of between 0.01 and 20 ml, more preferably of between 0.1 and 10 ml, more preferably between 0.5 and 8 ml and most preferably between 1 and 5 ml, e.g. 0.01, 0.05, 0.1, 0.2, 0.3, 0.4, 0.5, 0.6, 0.7, 0.8, 0.9, 1, 2, 2.5, 3, 4, 5, 6, 7, 8, 9, 10, 11, 12, 13, 14, 15, 16, 17, 18, 19, or 20 ml.

Preferably, the blood sample is collected by a blood collection tube. It is preferred that the blood collection tube includes means for stabilizing the RNA-fraction, especially the small RNA fraction within the blood sample. Not limiting examples for blood collection tubes already including a RNA-stabilization agent are PAXgene tubes (www.Preanalytix.com), or Tempus Blood RNA Tubes (Ambion, Applied Biosystems). Conventionally blood collection tubes, to which optionally a RNA-stabilizing agent like RNAlater (Ambion) can be added, are EDTA-, Heparin-, or Serum-tubes.

It is also preferred that the urine sample has a volume of between 0.01 and 20 ml, more preferably of between 0.1 and 10 ml, more preferably between 0.5 and 8 ml and most preferably between 1 and 5 ml, e.g. 0.01, 0.05, 0.1, 0.2, 0.3, 0.4, 0.5, 0.6, 0.7, 0.8, 0.9, 1, 2, 2.5, 3, 4, 5, 6, 7, 8, 9, 10, 11, 12, 13, 14, 15, 16, 17, 18, 19, or 20 ml.

It is further preferred that the cerebrospinal fluid (CSF) sample has a volume of between 0.01 and 20 ml, more preferably of between 0.1 and 10 ml, more preferably between 0.5 and 8 ml and most preferably between 1 and 5 ml, e.g. 0.01, 0.05, 0.1, 0.2, 0.3, 0.4, 0.5, 0.6, 0.7, 0.8, 0.9, 1, 2, 2.5, 3, 4, 5, 6, 7, 8, 9, 10, 11, 12, 13, 14, 15, 16, 17, 18, 19, or 20 ml.

The test sample may be from any organism such as vertebrate, particularly from any mammal, including both a human and another mammal, e.g. an animal such as a rodent, a rabbit, or a monkey. The rodent may be a mouse, rat, hamster, guinea pig, or chinchilla. Preferably, the test sample is from a human or a rodent.

Preferably, the patient is a patient to whom at least once (e.g. once, twice, or thrice/1, 2, 3, 4, or 5 times) a drug to be used in said therapeutic treatment is administered or has been administered. The drug to be used in said therapeutic treatment may be selected from the group consisting of natalizumab, interferon beta 1a, interferon beta 1b, glatiramer acetate, alemtuzumab, fingolimod, dimethylfumarate, and mitoxantrone. Preferably, the drug is natalizumab. The way of administration may be oral, nasal, rectal, parenteral, vaginal, or topical. Parental administration includes subcutaneous, intracutaneous, intramuscular, intravenous or intraperitoneal administration.

It is further preferred that the test sample is isolated from the patient after at least the first (e.g. first, second, third, fourth, or fifth) administration of said drug. It is particularly preferred that the test sample is isolated from the patient in a time period of between 12 months and 1 day after at least the first (e.g. first, second, third, fourth, or fifth) administration of said drug, it is particularly more preferred that the test sample is isolated from the patient in a time period of between 6 months and 1 day after at least the first (e.g. first, second, third, fourth, or fifth) administration of said drug, it is particularly even more preferred that the test sample is isolated from the patient in a time period of between 1 month and 1 day after at least the first (e.g. first, second, third, fourth, or fifth) administration of said drug, and it is particularly most preferred that the test sample is isolated from the patient in a time period of between 1 week and 1 day after at least the first (e.g. first, second, third, fourth, or fifth) administration of said drug, e.g. 1, 2, 3, 4, 5, 6, day(s), 1, 2, 3 week(s), 1, 2, 3, 4, 5, 6, 7, 8, 9, 10, 11, or 12 month(s) after at least the first (e.g. first, second, third, fourth, or fifth) administration of said drug.

It is also (alternatively or additionally) preferred that the level of the at least one miRNA in the test sample is compared to a reference level of the (said) at least one miRNA. Thus, in a preferred embodiment, the method of determining whether a patient responds to a therapeutic treatment of multiple sclerosis (MS) comprises the steps of:

(i) determining the level of at least one miRNA, e.g. 1, 2, 3, 4, 5, 6, 7, 8, 9, 10, 11, 12, 13, 14, or 15 miRNA(s), in a test sample isolated from the patient, wherein the nucleotide sequence of the at least one miRNA is selected from the group consisting of SEQ ID NO: 1 to SEQ ID NO: 15, a fragment thereof, and a sequence having at least 80% sequence identity thereto, and (ii) comparing the level of the at least one miRNA in the test sample to a reference level of the (said) at least one miRNA, e.g. 1, 2, 3, 4, 5, 6, 7, 8, 9, 10, 11, 12, 13, 14, or 15 miRNA(s).

As mentioned above, it is preferred that the patient is a patient to whom at least once (e.g. once, twice, or thrice, or 1, 2, 3, 4, or 5 times) a drug to be used in said therapeutic treatment is administered or has been administered. The drug to be used in said therapeutic treatment may be selected from the group consisting of natalizumab, interferon beta 1a, interferon beta 1b, glatiramer acetate, alemtuzumab, fingolimod, dimethylfumarate, and mitoxantrone. Preferably, the drug is natalizumab. It is further preferred that the test sample is isolated from the patient after at least the first (e.g. first, second, third, fourth, or fifth) administration of said drug.

In a preferred embodiment, the reference level is the level of the (said) at least one miRNA, e.g. 1, 2, 3, 4, 5, 6, 7, 8, 9, 10, 11, 12, 13, 14, or 15 miRNA(s), determined empirically by measuring a number of reference samples, preferably at least two reference samples, more preferably at least 2 to 40 reference samples, even more preferably at least 10 to 60 reference samples, and most preferably at least 50 to 100 reference samples, e.g. at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 reference samples, from (different) patients. Preferably or alternatively, said reference level is an average level. The average level is particularly determined by measuring a number of reference samples, preferably at least two reference samples, more preferably at least 2 to 40 reference samples, even more preferably at least 10 to 60 reference samples, and most preferably at least 50 to 100 reference samples, e.g. at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 reference samples, from a number of patients and calculating the "middle" value (e.g. median or mean value) of the reference levels determined therein. Said reference samples are preferably samples from multiple sclerosis patients, e.g. relapsing-remitting multiple sclerosis (RR-MS), secondary progressive multiple sclerosis (SPMS), progressive relapsing multiple sclerosis (PRMS), or primary progressive multiple sclerosis (PPMS) patients.

The term "multiple sclerosis (MS), e.g. RR-MS, SP-MS, PR-MS, or PP-MS, patients", as used herein, means patients suffering from the above defined MS, e.g. RR-MS, SP-MS, PR-MS, or PP-MS, symptoms (see definition of the terms "MS", "RR-MS", "SP-MS", "PR-MS", or "PP-MS"). The patients suffering from MS, particularly the patients suffering from RR-MS, may further be characterized by a deregulation of the miRNA(s) which nucleotide sequence(s) is (are) selected from the group consisting of SEQ ID NO: 1 to SEQ ID NO: 6, SEQ ID NO: 8, SEQ ID NO: 9 to SEQ ID NO: 11, SEQ ID NO: 15, a fragment thereof, and a sequence having at least 80% sequence identity thereto compared to healthy subjects/controls. Particularly, the level of the miRNA(s) which nucleotide sequence(s) is (are) selected from the group consisting of SEQ ID NO: 1 to SEQ ID NO: 6, SEQ ID NO: 8, a fragment thereof, and a sequence having at least 80% sequence identity thereto is decreased in MS, particularly RR-MS, compared to the level of the same miRNA(s) in healthy subjects/controls, while the level of the miRNA(s) which nucleotide sequence(s) is (are) selected from the group consisting of SEQ ID NO: 9 to SEQ ID NO: 11, SEQ ID NO: 15, a fragment thereof, and a sequence having at least 80% sequence identity thereto is increased in MS, particularly RR-MS, compared to the level of the same miRNA(s) in healthy subjects/controls.

The term "healthy subjects/controls", as used herein, means patients not suffering from multiple sclerosis. Said healthy subjects/controls do not exhibit the above defined symptoms (see definition of the terms "MS", "RR-MS", "SP-MS", "PR-MS", or "PP-MS"). However, said healthy subjects/controls may possibly suffer from another disease not known or tested. The healthy subject/control may be any organism such as vertebrate, particularly any mammal, including both a human and another mammal, e.g. an animal such as a rodent, a rabbit, or a monkey. The rodent may be a mouse, rat, hamster, guinea pig, or chinchilla. Preferably, the healthy subject/control is a human or a rodent.

It is also (alternatively or additionally) preferred that the reference level is determined in a reference sample isolated from the patient, particularly prior to the administration of said drug. For example, the reference level is the level of the (said) at least one miRNA, e.g. 1, 2, 3, 4, 5, 6, 7, 8, 9, 10, 11, 12, 13, 14, or 15 miRNA(s), determined empirically by measuring a number of reference samples, particularly at least two reference samples, from patients and the reference level is determined in the reference sample isolated from the patient prior to the administration of said drug. Further, for example, the reference level is the level of the (said) at least one miRNA, e.g. 1, 2, 3, 4, 5, 6, 7, 8, 9, 10, 11, 12, 13, 14, or 15 miRNA(s), determined empirically by measuring a number of reference samples, particularly at least two reference samples, from patients, said reference samples are samples from multiple sclerosis patients, e.g. relapsing-remitting multiple sclerosis (RR-MS), secondary progressive multiple sclerosis (SPMS), progressive relapsing multiple sclerosis (PRMS), or primary progressive multiple sclerosis (PPMS) patients, and the reference level is determined in the reference sample isolated from the patient prior to the administration of said drug. It is particularly preferred that the reference sample is isolated from the patient in a time period of between 3 months and immediately prior to the administration of said drug, it is particularly more preferred that the reference sample is isolated from the patient in a time period of between 1 month and immediately prior to the administration of said drug, it is particularly even more preferred that the reference sample is isolated from the patient in a time period of between 3 weeks and immediately prior to the administration of said drug, and it is particularly most preferred that the reference sample is isolated from the patient in a time period of between 1 day and immediately prior to the administration of said drug or between 1 hour and immediately prior to the administration of said drug, e.g. immediately, 10, 20, 30, 40, 50 minutes, 1, 2, 3, 4, 5, 6, 7, 8, 9, 10, 11, 12, 13, 14, 15, 16, 17, 18, 19, 20, 21, 22, 23 hour(s), 1, 2, 3, 4, 5, 6 day(s), 1, 2, 3 week(s), 1, 2, or 3 month(s) prior to the administration of said drug.

In an alternative preferred embodiment, the reference level is the level of the (said) at least one miRNA, e.g. 1, 2, 3, 4, 5, 6, 7, 8, 9, 10, 11, 12, 13, 14, or 15 miRNA(s), determined in a reference sample isolated from the same patient. Particularly, the reference level is determined in a reference sample isolated from the same patient prior to the administration of said drug. Preferably, said (multiple sclerosis) patient is a patient suffering from relapsing-remitting multiple sclerosis (RR-MS), secondary progressive multiple sclerosis (SPMS), progressive relapsing multiple sclerosis (PRMS), or primary progressive multiple sclerosis (PPMS). As to the definition of the term "multiple sclerosis (MS), e.g. RR-MS, SP-MS, PR-MS, or PP-MS, patient", it is referred to the above definition. For example, the reference level is the level of the (said) at least one miRNA, e.g. 1, 2, 3, 4, 5, 6, 7, 8, 9, 10, 11, 12, 13, 14, or 15 miRNA(s), determined in the reference sample isolated from the same patient, particularly prior to the administration of said drug, and said patient is a relapsing-remitting multiple sclerosis (RR-MS) patient, secondary progressive multiple sclerosis (SPMS) patient, progressive relapsing multiple sclerosis (PRMS) patient, or primary progressive multiple sclerosis (PPMS) patient. It is particularly preferred that the reference sample is isolated from the same patient in a time period of between 3 months and immediately prior to the administration of said drug, it is particularly more preferred that the reference sample is isolated from the same patient in a time period of between 1 month and immediately prior to the administration of said drug, it is particularly even more preferred that the reference sample is isolated from the same patient in a time period of between 3 weeks and immediately prior to the administration of said drug, and it is particularly most preferred that the reference sample is isolated from the same patient in a time period of between 1 day and immediately prior to the administration of said drug or between 1 hour and immediately prior to the administration of said drug, e.g. immediately, 10, 20, 30, 40, 50 minutes, 1, 2, 3, 4, 5, 6, 7, 8, 9, 10, 11, 12, 13, 14, 15, 16, 17, 18, 19, 20, 21, 22, 23 hour(s), 1, 2, 3, 4, 5, 6 day(s), 1, 2, 3 week(s), 1, 2, or 3 month(s) prior to the administration of said drug.

The term "reference sample", as used herein, refers to any biological sample containing (a) miRNA(s), particularly containing (a) miRNA(s) with (a) nucleotide sequence(s) according to SEQ ID NO: 1 to SEQ ID NO: 15, a fragment thereof, or a sequence having at least 80% sequence identity thereto. Said reference sample may be a body fluid sample, a tissue sample, or a cell sample. For example, reference samples encompassed by the present invention are tissue (e.g. section or explant) samples, single cell samples, cell colony samples, cell culture samples, blood (e.g. whole blood or blood fraction such as blood cell fraction, serum or plasma) samples, urine samples, cerebrospinal fluid (CSF) samples, or samples from other peripheral sources. Said reference samples may be mixed or pooled, e.g. a reference sample may be a mixture of a blood sample and an urine sample. A "reference sample" may be provided by removing a body fluid, cell(s), cell colonies, an explant, or a section from a patient, but may also be provided by using a previously isolated sample. For example, a tissue sample may be removed from a patient by conventional biopsy techniques or a blood sample may be taken from a patient by conventional blood collection techniques. The reference sample, e.g. tissue sample or blood sample, may be obtained from a patient prior to initiation of the therapeutic treatment, during the therapeutic treatment, and/or after the therapeutic treatment. It is also preferred that total RNA or a subfraction thereof, isolated (e.g. extracted) from a reference sample of a patient (e.g. human or rodent), is used.

Preferably, the reference sample is a body fluid sample, a tissue sample, a cell colony sample, a single cell sample or a cell culture sample. Said reference samples may be mixed or pooled, e.g. the reference sample may be a mixture of a body fluid sample and a tissue sample or a mixture of a body fluid sample and a cell culture sample. More preferably, the tissue sample is a section or an explant sample.

It is preferred that the tissue sample has a weight of between 0.1 and 500 mg, more preferably of between 0.5 and 250 mg, and most preferably of between 1 and 50 mg, e.g. 0.1, 0.2, 0.3, 0.4, 0.5, 0.6, 0.7, 0.8, 0.9, 1, 2, 2.5, 3, 4, 5, 6, 7, 8, 9, 10, 15, 20, 25, 30, 35, 40, 45, 50, 55, 60, 65, 70, 75, 80, 85, 90, 95, 100, 125, 150, 175, 200, 225, 250, 275, 300, 325, 350, 375, 400, 425, 450, 475, or 500 mg.

It is also preferred that the cell sample (e.g. cell colony sample or cell culture sample) consists of between $10^2$ and $10^{10}$ cells, more preferably of between $10^3$ and $10^7$ cells, and most preferably of between $10^4$ and $10^6$ cells, e.g. $10^2$, $10^3$, $10^4$, $10^5$, $10^6$, $10^7$, $10^8$, $10^9$, or $10^{10}$ cells.

A body fluid sample is a liquid sample derived from the body of a patient, e.g. human or rodent. Said body fluid sample may be a blood sample, urine sample, sputum sample, breast milk sample, cerebrospinal fluid (CSF) sample, cerumen (earwax) sample, endolymph sample, perilymph sample, gastric juice sample, mucus sample, peritoneal fluid sample, pleural fluid sample, saliva sample, sebum (skin oil) sample, semen sample, sweat sample, tears sample, vaginal secretion sample, or vomit sample including components or fractions thereof. Said body fluid samples may be mixed or pooled. Thus, a body fluid sample may be a mixture of a blood and an urine sample or a mixture of a blood and cerebrospinal fluid sample. A body fluid sample may be provided by removing a body liquid from a patient, but may also be provided by using previously isolated body fluid sample material. Said "body fluid sample" allows for a non-invasive analysis of a patient, e.g. human or rodent.

It is further preferred that the body fluid sample has a volume of between 0.01 and 20 ml, more preferably of between 0.1 and 10 ml, more preferably between 0.5 and 8 ml and most preferably between 1 and 5 ml, e.g. 0.01, 0.05, 0.1, 0.2, 0.3, 0.4, 0.5, 0.6, 0.7, 0.8, 0.9, 1, 2, 2.5, 3, 4, 5, 6, 7, 8, 9, 10, 11, 12, 13, 14, 15, 16, 17, 18, 19, or 20 ml.

More preferably, the body fluid sample is a blood sample, an urine sample, or a cerebrospinal fluid (CSF) sample, or mixtures thereof.

Most preferably, the blood sample is a whole blood or blood fraction sample such as a blood cell fraction, serum or plasma sample. It is particularly preferred to use blood cells also known as hemopoietic cells. Hemopoietic cells are mature cell types and their immature precursors are identifiable either by morphology or, mostly, by a distinct pattern of cell surface markers. Said term is used to distinguish these cells from other cell types found in the body and also includes T-cells and distinctive subsets, which are the only hematopoietic cells that are not generated in the bone marrow. Said blood cells may be erythrocytes, leukocytes, and/or thrombocytes, e.g. mixtures thereof. For example, the blood cell sample may be an erythrocyte, a leukocyte and/or a thrombocyte containing sample. Peripheral blood mononuclear cells (PBMCs) such as lymphocytes, monocytes or macrophages may also be used.

It is preferred that the blood sample has a volume of between 0.01 and 20 ml, more preferably of between 0.1 and 10 ml, more preferably between 0.5 and 8 ml and most preferably between 1 and 5 ml, e.g. 0.01, 0.05, 0.1, 0.2, 0.3, 0.4, 0.5, 0.6, 0.7, 0.8, 0.9, 1, 2, 2.5, 3, 4, 5, 6, 7, 8, 9, 10, 11, 12, 13, 14, 15, 16, 17, 18, 19, or 20 ml.

Preferably, the blood sample is collected by a blood collection tube. It is preferred that the blood collection tube includes means for stabilizing the RNA-fraction, especially the small RNA fraction within the blood sample. Not limiting examples for blood collection tubes already including a RNA-stabilization agent are PAXgene tubes (www.Preanalytix.com), or Tempus Blood RNA Tubes (Ambion, Applied Biosystems). Conventionally blood collection tubes, to which optionally a RNA-stabilizing agent like RNAlater (Ambion) can be added, are EDTA-, Heparin-, or Serum-tubes.

It is also preferred that the urine sample has a volume of between 0.01 and 20 ml, more preferably of between 0.1 and 10 ml, more preferably between 0.5 and 8 ml and most preferably between 1 and 5 ml, e.g. 0.01, 0.05, 0.1, 0.2, 0.3, 0.4, 0.5, 0.6, 0.7, 0.8, 0.9, 1, 2, 2.5, 3, 4, 5, 6, 7, 8, 9, 10, 11, 12, 13, 14, 15, 16, 17, 18, 19, or 20 ml.

It is further preferred that the cerebrospinal fluid (CSF) sample has a volume of between 0.01 and 20 ml, more preferably of between 0.1 and 10 ml, more preferably between 0.5 and 8 ml and most preferably between 1 and 5 ml, e.g. 0.01, 0.05, 0.1, 0.2, 0.3, 0.4, 0.5, 0.6, 0.7, 0.8, 0.9, 1, 2, 2.5, 3, 4, 5, 6, 7, 8, 9, 10, 11, 12, 13, 14, 15, 16, 17, 18, 19, or 20 ml.

The reference sample may be from any organism such as vertebrate, particularly from any mammal, including both a human and another mammal, e.g. an animal such as a rodent, a rabbit, or a monkey. The rodent may be a mouse, rat, hamster, guinea pig, or chinchilla. Preferably, the reference sample is from a human or a rodent.

Preferably, the reference sample is from the same source than the test sample, e.g. both are blood samples, cerebrospinal fluid (CSF) samples, or urine samples, for example, from a human or a rodent. It is also (alternatively or additionally) preferred that the measurements of the reference sample and test sample are identical, e.g. both have an identical volume. It is particularly preferred that the reference sample and test sample are from patients of the same sex and age. For example, the reference sample and test sample are from the same source and the reference sample and test sample are from patients of the same sex and age. Further, for example, the measurements of the reference sample and test sample are identical and the reference and test sample are from patients of the same sex and age. Furthermore, for example, the reference sample and test sample are from the same source, the measurements of the reference sample and test sample are identical and the reference and test sample are from patients of the same sex and age.

It is further preferred that the patients, from which the test samples and/or the reference samples are, have undergone a wash-out period to remove any pharmaceutical substances from the body. For example, the patients that receive or have received a drug for therapeutic treatment of multiple sclerosis, e.g. natalizumab, have undergone a 3-month was-out period prior to the administration of said drug.

As mentioned above, it is preferred that the level of the at least one miRNA, e.g. 1, 2, 3, 4, 5, 6, 7, 8, 9, 10, 11, 12, 13, 14, or 15 miRNA(s), in the test sample is compared to a reference level of the (said) at least one miRNA. In addition, the preferred embodiments of the reference level and reference sample are described above.

In a preferred embodiment, the nucleotide sequence of the at least one miRNA, e.g. 1, 2, 3, 4, 5, 6, 7, or 8 miRNA(s), is selected from the group consisting of SEQ ID NO: 1 to SEQ ID NO: 8, a fragment thereof, and a sequence having at least 80% sequence identity thereto, preferably SEQ ID NO: 1, SEQ ID NO: 2, SEQ ID NO: 5 to SEQ ID NO: 8, a fragment thereof, and a sequence having at least 80% sequence identity thereto, more preferably SEQ ID NO: 1, SEQ ID NO: 2, a fragment thereof, and a sequence having at least 80% sequence identity thereto, wherein an increase of the level of the at least one miRNA in the test sample when compared to the reference level of the at least one miRNA indicates that the patient responds to said treatment of multiples sclerosis. More preferably, the miRNAs have nucleotide sequences according to SEQ ID NO: 1, a fragment thereof, or a sequence having at least 80% sequence identity thereto and according to SEQ ID NO: 2, a fragment thereof, or a sequence having at least 80% sequence identity thereto. In a particularly preferred embodiment, the nucleotide sequence of the at least one miRNA, e.g. 1 or 2 miRNA(s), is selected from the group consisting of SEQ ID NO: 3, SEQ ID NO: 4, a fragment thereof, and a sequence having at least 80% sequence identity thereto, wherein an increase of the level of the at least one miRNA in the test sample when compared to the reference level of the at least one miRNA only indicates that the patient responds to said treatment of multiples sclerosis when the level of at least one miRNA, e.g. 1 or 2 miRNA(s), selected from the group consisting of SEQ ID NO: 1, SEQ ID NO: 2, a fragment thereof, and a sequence having at least 80% sequence identity thereto in the test sample when compared to the reference level of the at least one miRNA is not decreased.

In another preferred embodiment, the nucleotide sequence of the at least one miRNA, e.g. 1, 2, 3, 4, 5, 6, or 7 miRNA(s), is selected from the group consisting of SEQ ID NO: 9 to SEQ ID NO: 15, a fragment thereof, and a sequence having at least 80% sequence identity thereto, preferably SEQ ID NO: 10 to SEQ ID NO: 15, a fragment thereof, and a sequence having at least 80% sequence identity thereto, wherein a decrease of the level of the at least one miRNA in the test sample when compared to the reference level of the at least one miRNA indicates that the patient responds to said treatment of multiples sclerosis. In a particularly preferred embodiment, the nucleotide sequence of the at least one miRNA is SEQ ID NO: 9, a fragment thereof, or a sequence having at least 80% sequence identity thereto, wherein a decrease of the level of the at least one miRNA in the test sample when compared to the reference level of the at least one miRNA only indicates that the patient responds to said treatment of multiples sclerosis when the level of at least one miRNA, e.g. 1 or 2 miRNA(s), selected from the group consisting of SEQ ID NO: 1, SEQ ID NO: 2, a fragment thereof, and a sequence having at least 80% sequence identity thereto in the test sample when compared to the reference level of the at least one miRNA is not decreased.

If the level of more than one miRNA is determined and if the nucleotide sequences of said miRNAs are selected from SEQ ID NO: 1 to SEQ ID NO: 8, a fragment thereof, and a sequence having at least 80% sequence identity thereto, preferably SEQ ID NO: 1, SEQ ID NO: 2, SEQ ID NO: 5 to SEQ ID NO: 8, a fragment thereof, and a sequence having at least 80% sequence identity thereto and are selected from SEQ ID NO: 9 to SEQ ID NO: 15, a fragment thereof, and a sequence having at least 80% sequence identity thereto, preferably SEQ ID NO: 10 to SEQ ID NO: 15, a fragment thereof, and a sequence having at least 80% sequence identity thereto, the above mentioned embodiments can also be combined. For example, in an embodiment, the nucleotide sequence of the at least one miRNA, e.g. 1, 2, 3, 4, 5, 6, 7, or 8 miRNA(s), is selected from the group consisting of SEQ ID NO: 1 to SEQ ID NO: 8, a fragment thereof, and a sequence having at least 80% sequence identity thereto, preferably SEQ ID NO: 1, SEQ ID NO: 2, SEQ ID NO: 5 to SEQ ID NO: 8, a fragment thereof, and a sequence having at least 80% sequence identity thereto, wherein an increase of the level of the at least one miRNA in the test sample when compared to the reference level of the at least one miRNA indicates that the patient responds to said treatment of multiples sclerosis, and the nucleotide sequence of the at least one miRNA, e.g. 1, 2, 3, 4, 5, 6, or 7 miRNA(s), is selected from the group consisting of SEQ ID NO: 9 to SEQ ID NO: 15, a fragment thereof, and a sequence having at least 80% sequence identity thereto, preferably SEQ ID NO: 10 to SEQ ID NO: 15, a fragment thereof, and a sequence having at least 80% sequence identity thereto, wherein a decrease of the level of the at least one miRNA in the test sample when compared to the reference level of the at least one miRNA indicates that the patient responds to said treatment of multiples sclerosis.

More preferably,
(i) an at least 1.2 fold increase, preferably an at least 1.4 fold increase, of the level of the miRNA having a nucleotide sequence according to SEQ ID NO: 1, an at least 1.2 fold increase, preferably an at least 1.4 fold increase, of the level of the miRNA having a nucleotide sequence according to SEQ ID NO: 2, an at least 1.2 fold increase, preferably an at least 1.4 fold increase, of the level of the miRNA having a nucleotide sequence according to SEQ ID NO: 3, an at least 1.2 fold increase, preferably an at least 1.4 fold increase, of the level of the miRNA having a nucleotide sequence according to SEQ ID NO: 4, an at least 1.2 fold increase, preferably an at least 1.4 fold increase, of the level of the miRNA having a nucleotide sequence according to SEQ ID NO: 5, an at least 1.2 fold increase, preferably an at least 1.4 fold increase, of the level of the miRNA having a nucleotide sequence according to SEQ ID NO: 6, an at least 1.2 fold increase, preferably an at least 1.4 fold increase, of the level of the miRNA having a nucleotide sequence according to SEQ ID NO: 7, and/or an at least 1.2 fold increase, preferably an at least 1.4 fold increase, of the level of the miRNA having a nucleotide sequence according to SEQ ID NO: 8 indicates that the patient responds to said treatment of multiples sclerosis, and/or
(ii) an at least 1.2 fold decrease, preferably an at least 1.4 fold decrease, of the level of the miRNA having a nucleotide sequence according to SEQ ID NO: 9, an at least 1.2 fold decrease, preferably an at least 1.4 fold decrease, of the level of the miRNA having a nucleotide sequence according to SEQ ID NO: 10, an at least 1.2 fold decrease, preferably an at least 1.4 fold decrease, of the level of the miRNA having a nucleotide sequence according to SEQ ID NO: 11, an at least 1.2 fold decrease, preferably an at least 1.4 fold decrease, of the level of the miRNA having a nucleotide sequence according to SEQ ID NO: 12, an at least 1.2 fold decrease, preferably an at least 1.4 fold decrease, of the level of the miRNA having a nucleotide sequence according to SEQ ID NO: 13, an at least 1.2 fold decrease, preferably an at least 1.4 fold decrease, of the level of the miRNA having a nucleotide sequence according to SEQ ID NO: 14, and/or an at least 1.2 fold decrease, preferably an at least 1.4 fold decrease, of the level of the miRNA having a nucleotide sequence according to SEQ ID NO: 15 indicates that the patient responds to said treatment of multiples sclerosis.

The above method is a method of determining whether a patient responds to a therapeutic treatment of multiple sclerosis (MS). Said patient may be a patient to whom at least once a drug to be used in said therapeutic treatment is administered or has been administered. The drug to be used in said therapeutic treatment may be selected from the group consisting of natalizumab, interferon beta 1a, interferon beta 1b, glatiramer acetate, alemtuzumab, fingolimod, dimethyl-fumarate, and mitoxantrone. In a preferred embodiment, the above method further comprises the step of administering at least once a renewed dose of the drug when the patient responds to said treatment of multiple sclerosis, or administering at least once a dose of the drug which is increased compared to the previously administered dose of the drug when the patient does not respond to said treatment of multiple sclerosis. Alternatively, when the patient does not respond to said treatment of multiple sclerosis, the administered drug may be changed, i.e. another drug (e.g. selected from the group consisting of natalizumab, interferon beta 1a, interferon beta 1b, glatiramer acetate, alemtuzumab, fingolimod, dimethylfumarate, and mitoxantrone) may be administered. In another preferred embodiment, the above method further comprises the step of continuing the treatment of multiple sclerosis when the patient responds to said treatment, or discontinuing the treatment of multiple sclerosis when the patient does not respond to said treatment. In the latter case, the administered drug may be changed (i.e. another drug e.g. selected from the group consisting of natalizumab, interferon beta 1a, interferon beta 1b, glatiramer acetate, alemtuzumab, fingolimod, dimethylfumarate, and mitoxantrone may be administered) and particularly, the response of the patient to the therapeutic treatment of multiple sclerosis may be retested.

The above method allows (additionally or alternatively) the determination of the dose at which the patient responds to a therapeutic treatment of multiple sclerosis by determining the level of at least one miRNA in a test sample isolated from the patient, wherein the nucleotide sequence of the at least one miRNA is selected from the group consisting of SEQ ID NO: 1 to SEQ ID NO: 15, a fragment thereof, and a sequence having at least 80% sequence identity thereto. Therefore, preferably, the patient is a patient to whom more than once, e.g. 2, 3, 4, or 5 times, an increasing dose of a drug to be used in said therapeutic treatment is administered or has been administered (e.g. in form of a concentration series). For example, the patient is a patient to whom an increasing dose of 0.5, 1, 1.5, 2, 2.5, 3, 3.5, 4, or 5 mg per kg bodyweight of said drug is administered or has been administered. In addition, the test sample may be isolated from the patient after the administration of said drug, e.g. after the second, third, fourth, fifth, first and second, first to third, first to fourth, or first to fifth administration of said drug. The drug to be used in said therapeutic treatment may be selected from the group consisting of natalizumab, interferon beta 1a, interferon beta 1b, glatiramer acetate, alemtuzumab, fingolimod, dimethylfumarate, and mitoxantrone. The level of the at least one miRNA in the test sample may then be compared to a reference level of the (said) at least one miRNA, preferably determined in a reference sample isolated from the patient prior to administration of said drug. Said reference level may be an average level obtained by measuring a number of reference samples, e.g. at least two reference samples, from (different) patients such as from patients suffering from multiples sclerosis, or may be obtained from the same patient.

The comparison of the level of the at least one miRNA in the test sample to the reference level of the (said) at least one miRNA finally allows determining whether, particularly at which dose, the patient response to the therapeutic treatment of multiple sclerosis. For example, the nucleotide sequence of the at least one miRNA, e.g. 1, 2, 3, 4, 5, 6, 7, or 8 miRNA(s), may be selected from the group consisting of SEQ ID NO: 1 to SEQ ID NO: 8, a fragment thereof, and a sequence having at least 80% sequence identity thereto, preferably SEQ ID NO: 1, SEQ ID NO: 2, SEQ ID NO: 5 to SEQ ID NO: 8, a fragment thereof, and a sequence having at least 80% sequence identity thereto, more preferably SEQ ID NO: 1, SEQ ID NO: 2, a fragment thereof, and a sequence having at least 80% sequence identity thereto, wherein an increase of the level of the at least one miRNA in the test sample when compared to the reference level of the at least one miRNA indicates that the patient responds to said treatment of multiples sclerosis. Further, for example, the nucleotide sequence of the at least one miRNA, e.g. 1, 2, 3, 4, 5, 6, or 7 miRNA(s), may selected from the group consisting of SEQ ID NO: 9 to SEQ ID NO: 15, a fragment thereof, and a sequence having at least 80% sequence identity thereto, preferably SEQ ID NO: 10 to SEQ ID NO: 15, a fragment thereof, and a sequence having at least 80% sequence identity thereto, wherein a decrease of the level of the at least one miRNA in the test sample when compared to the reference level of the at least one miRNA indicates that the patient responds to said treatment of multiples sclerosis.

The above (in the context of the first aspect of the invention) mentioned nucleotide sequence of the miRNA is selected from the group consisting of
(i) a nucleotide sequence according to SEQ ID NO: 1 to SEQ ID NO: 15,
(ii) a nucleotide sequence that is a fragment of the nucleotide sequence according to (i), preferably, a nucleotide sequence that is a fragment which is between 1 and 12, more preferably between 1 and 8, and most preferably between 1 and 5 or 1 and 3, i.e. 1, 2, 3, 4, 5, 6, 7, 8, 9, 10, 11, or 12, nucleotides shorter than the nucleotide sequence according to (i), and
(iii) a nucleotide sequence that has at least 80%, preferably at least 85%, more preferably at least 90%, and most preferably at least 95% or 99%, i.e. 80, 81, 82, 83, 84, 85, 86, 87, 88, 89, 90, 91, 92, 93, 94, 95, 96, 97, 98, or 99%, sequence identity to the nucleotide sequence according to (i) or nucleotide sequence fragment according to (ii).

It is particularly preferred that the nucleotide sequence as defined in (iii) has at least 80%, preferably at least 85%, more preferably at least 90%, and most preferably at least 95% or 99%, i.e. 80, 81, 82, 83, 84, 85, 86, 87, 88, 89, 90, 91, 92, 93, 94, 95, 96, 97, 98, or 99%, sequence identity over a continuous stretch of at least 10, 11, 12, 13, 14, 15, 16, 17, 18, 19, 20 or more nucleotides, preferably over the whole length, to the nucleotide sequence of the nucleotide according to (i) or nucleotide fragment according to (ii).

In addition, the nucleotide sequence as defined in (ii) (i.e. nucleotide sequence fragment) or (iii) (i.e. nucleotide sequence variant or nucleotide sequence fragment variant) is only regarded as a nucleotide sequence as defined in (ii) (i.e. nucleotide sequence fragment) or (iii) (i.e. nucleotide sequence variant or nucleotide sequence fragment variant) within the context of the present invention, if it can still be bound, hybridized, recognized, or detected by a polynucleotide (probe) of complementary sequence, e.g. a polynucleotide (probe) which is complementary to the respective nucleotide sequence as defined in (i), through one or more types of chemical bonds, usually through complementary base pairing, usually through hydrogen bond formation under stringent hybridization conditions. The skilled person can readily assess whether a nucleotide sequence as defined in (ii) (i.e. nucleotide sequence fragment) or (iii) (i.e. nucleotide sequence variant or nucleotide sequence fragment variant) can still be bound, hybridized, recognized, or detected by a polynucleotide (probe) of complementary sequence, e.g. a polynucleotide (probe) which is complementary to the respective nucleotide sequence as defined in (i). Suitable assays to determine whether hybridization under stringent conditions still occurs are well known in the art. However, as an example, a suitable assay to determine whether hybridization still occurs comprises the steps of: (a) incubating a nucleotide sequence as defined in (ii) or (iii) labelled with biotin with a polynucleotide (probe) of complementary sequence, e.g. a polynucleotide (probe) which is complementary to the respective nucleotide sequence as defined in (i), wherein the polynucleotide (probe) is attached onto a biochip, under stringent hybridization conditions, (b) washing the biochip to remove unspecific bindings, (c) subjecting the biochip to a detection system, and (c) analyzing whether the nucleotide sequence can still be hybridized or detected by a polynucleotide (probe) of complementary sequence, e.g. a polynucleotide (probe) which is complementary to the respective nucleotide sequence as defined in (i). As a positive control, the respective miRNA as defined in (i) may be used. Preferably stringent hybridization conditions include the following: 50% formamide, 5×SSC, and 1% SDS, incubating at 42° C., or, 5×SSC, 1% SDS, incubating at 65° C., with wash in 0.2×SSC, and 0.1% SDS at 65° C.; or 6×SSPE, 10% formamide, 0.01%, Tween 20, 0.1×TE buffer, 0.5 mg/ml BSA, 0.1 mg/ml herring sperm DNA, incubating at 42° C. with wash in 0.5×SSPE and 6×SSPE at 45° C.

The patient may be any organism such as vertebrate, particularly any mammal, including both a human and another mammal, e.g. an animal such as a rodent, a rabbit, or a monkey. The rodent may be a mouse, rat, hamster, guinea pig, or chinchilla. Preferably, the patient is a human or a rodent.

Preferably, multiples sclerosis (MS) is relapsing-remitting multiple sclerosis (RR-MS), secondary progressive multiple sclerosis (SPMS), progressive relapsing multiple sclerosis (PRMS), or primary progressive multiple sclerosis (PPMS). More preferably, multiples sclerosis (MS) is relapsing-remitting multiple sclerosis (RR-MS).

As mentioned above, the method of determining whether a patient responds to a therapeutic treatment of multiple sclerosis (MS) comprises the step of:
determining the level of at least one miRNA, e.g. 1, 2, 3, 4, 5, 6, 7, 8, 9, 10, 11, 12, 13, 14, or 15 miRNA(s), in a test sample isolated from the patient, wherein the nucleotide sequence of the at least one miRNA is selected from the group consisting of SEQ ID NO: 1 to SEQ ID NO: 15, a fragment thereof, and a sequence having at least 80% sequence identity thereto.

It is preferred that the level of the miRNA is the expression level. Said level of the miRNA, particularly expression level of the miRNA, may be indicated as (relative) miRNA concentration, (relative) miRNA amount, or (relative) miRNA extinction units such as relative fluorescence units.

The determination may be carried out by any convenient means for determining the level of the miRNA, particularly, the expression level of the miRNA. For example, qualitative, semi-quantitative and/or quantitative detection methods may be used. A variety of techniques are well known to the person skilled in the art. Preferably the level of the miRNA, particularly the expression level of the miRNA, is determined by nucleic acid hybridization, nucleic acid amplification, polymerase extension, sequencing, mass spectroscopy or any combination thereof.

Nucleic acid amplification may be performed using real time polymerase chain reaction (RT-PCR) such as real time quantitative polymerase chain reaction (RT qPCR). The real time polymerase chain reaction (RT-PCR) is preferred for the analysis of a single miRNA or a low number of miRNAs. It is particularly suitable for detecting low abundance miR- NAs. The real time quantitative polymerase chain reaction (RT qPCR), however, allows the analysis of a single miRNA and a high number of miRNAs.

The aforesaid real time polymerase chain reaction (RT-PCR) may include the following steps: (i) extracting the total RNA from a test (e.g. whole blood, serum, or plasma) sample of a patient and obtaining cDNA samples by RNA reverse transcription (RT) reaction using miRNA-specific primers, or collecting a test (e.g. whole blood, serum, or plasma) sample of a patient and conducting reverse transcriptase reaction using miRNA-specific primers with the test (e.g. whole blood, serum, or plasma) sample being a buffer so as to prepare cDNA samples, (ii) designing miRNA-specific cDNA forward primers and providing universal reverse primers to amplify the cDNA via polymerase chain reaction (PCR), (iii) adding a fluorescent probe to conduct PCR, and (iv) detecting the miRNA(s) level in the test (e.g. whole blood, serum, or plasma) sample.

A variety of kits and protocols to determine the expression level by real time polymerase chain reaction (RT-PCR) such as real time quantitative polymerase chain reaction (RT qPCR) are available. For example, reverse transcription of miRNAs may be performed using the TaqMan MicroRNA Reverse Transcription Kit (Applied Biosystems) according to manufacturer's recommendations. Briefly, miRNA may be combined with dNTPs, MultiScribe reverse transcriptase and the primer specific for the target miRNA. The resulting cDNA may be diluted and may be used for PCR reaction. The PCR may be performed according to the manufacturer's recommendation (Applied Biosystems). Briefly, cDNA may be combined with the TaqMan assay specific for the target miRNA and PCR reaction may be performed using ABI7300.

Nucleic acid hybridization may be performed using a microarray/biochip or in situ hybridization. In situ hybridization is preferred for the analysis of a single miRNA or a low number of miRNAs. The microarray/biochip, however, allows the analysis of a single miRNA and a high number of miRNAs.

Preferably, (i) the nucleic acid hybridization is performed using a microarray/biochip or beads, or using in situ hybridization, and/or (ii) the nucleic acid amplification is performed using real-time PCR.

In a preferred embodiment, the (expression) level of the at least one miRNA is determined by determining the level of the cDNA generated/transcribed from said miRNA. Preferably, said level is determined using a real time quantitative polymerase chain reaction (RT qPCR).

In another preferred embodiment, the level of the at least one miRNA is determined after a size selection of RNA which is smaller than 1000 base pairs, preferably smaller than 500 base pairs, more preferably smaller than 100 base pairs, and most preferably smaller than 30 base pairs.

In a further preferred embodiment the level of the at least one miRNA is determined from a test sample that includes means for stabilizing the RNA-fraction, especially the small RNA fraction. Preferably, the means for stabilizing the RNA fraction, especially the small RNA-fraction, have been either added to the test sample during or after blood collection (e.g. by adding RNAlater, or RNAretain) or were already included in the blood collection tube (e.g PAXgene tube, PAXgene blood RNA tube, or Tempus blood RNA tube).

It is preferred that the polynucleotide (probe) according to the sixth aspect of the invention or the polynucleotide set comprising at least two different polynucleotide (probes) according to the seventh aspect of the invention is used in the method of the first aspect of the invention to determine the level, particularly expression level, of at least one miRNA in a test sample isolated from the patient, wherein the nucleotide sequence of the at least one miRNA is selected from the group consisting of SEQ ID NO: 1 to SEQ ID NO: 15, a fragment thereof, and a sequence having at least 80% sequence identity thereto. It is particularly preferred that said polynucleotide is part of a biochip, or comprised on beads or microspheres or said at least two different polynucleotides are comprised on a biochip, or on a set of beads or microspheres.

In a second aspect, the present invention relates to a method of monitoring the course of multiple sclerosis (MS) in a patient comprising the step of:

determining the level of at least one miRNA in a test sample isolated from the patient, wherein the nucleotide sequence of the at least one miRNA is selected from the group consisting of SEQ ID NO: 1 to SEQ ID NO: 15, a fragment thereof, and a sequence having at least 80% sequence identity thereto.

It is preferred that the level of the nucleotide sequence of the miRNA having SEQ ID NO: 1, SEQ ID NO: 2, SEQ ID NO: 3, SEQ ID NO: 4, SEQ ID NO: 9, a fragment thereof, or a sequence having at least 80% sequence identity thereto is determined. It is particularly preferred that the level of the nucleotide sequence of the miRNA having SEQ ID NO: 1, SEQ ID NO: 2, a fragment thereof, or a sequence having at least 80% sequence identity thereto is determined.

In an alternative embodiment, the level of the nucleotide sequence of the miRNA having SEQ ID NO: 3, a fragment thereof, or a sequence having at least 80% sequence identity thereto, and/or the level of the nucleotide sequence of the miRNA having SEQ ID NO: 9, a fragment thereof, or a sequence having at least 80% sequence identity thereto is not determined.

It is further preferred that the level of the nucleotide sequences of the miRNAs having SEQ ID NO: 1 to SEQ ID NO: 15, fragments thereof, or sequences having at least 80% sequence identity thereto is determined. It is particularly preferred that the level of the nucleotide sequences of the miRNAs having SEQ ID NO: 1 to SEQ ID NO: 8, fragments thereof, or sequences having at least 80% sequence identity thereto is determined or that the level of nucleotide sequences of the miRNAs having SEQ ID NO: 9 to SEQ ID NO: 15, fragments thereof, or sequences having at least 80% sequence identity thereto is determined. It is more preferred that the level of the nucleotide sequences of the miRNAs having SEQ ID NO: 1 to SEQ ID NO: 4 and SEQ ID NO: 9, fragments thereof, or sequences having at least 80% sequence identity thereto is determined. It is particularly more preferred that the level of the nucleotide sequences of the miRNAs having SEQ ID NO: 1 to SEQ ID NO: 4, fragments thereof, or sequences having at least 80% sequence identity thereto is determined. It is most preferred that the level of the nucleotide sequences of the miRNAs having (i) SEQ ID NO: 1 and SEQ ID NO: 2, fragments thereof, or sequence having at least 80% sequence identity thereto, (ii) SEQ ID NO: 1 and SEQ ID NO: 3, fragments thereof, or sequences having at least 80% sequence identity thereto, (iii) SEQ ID NO: 1 and SEQ ID NO: 4, fragments thereof, or sequences having at least 80% sequence identity thereto, (iv) SEQ ID NO: 2 and SEQ ID NO: 3, fragments thereof, or sequences having at least 80% sequence identity thereto, (v) SEQ ID NO: 2 and SEQ ID NO: 4, fragments thereof, or sequences having at least 80% sequence identity thereto, or (vi) SEQ ID NO: 3 and SEQ ID NO: 4, fragments thereof, or sequences having at least 80% sequence identity thereto is determined.

In case of the miRNA having a nucleotide sequence according to SEQ ID NO: 3, a fragment thereof, or a sequence having at least 80% sequence identity thereto, it is preferred that the level of this miRNA is only determined together with the level of at least one further miRNA having a nucleotide sequence selected from the group consisting of SEQ ID NO: 1, SEQ ID NO: 2, SEQ ID NO: 4 to SEQ ID NO: 15, a fragment thereof, and a sequence having at least 80% sequence identity thereto, particularly selected from the group consisting of SEQ ID NO: 1, SEQ ID NO: 2, SEQ ID NO: 4 to SEQ ID NO: 8, SEQ ID NO: 10 to SEQ ID NO: 15, a fragment thereof, and a sequence having at least 80% sequence identity thereto, or in case of the miRNA having a nucleotide sequence according to SEQ ID NO: 9, a fragment thereof, or a sequence having at least 80% sequence identity thereto, it is preferred that the level of this miRNA is only determined together with the level of at least one further miRNA having a nucleotide sequence selected from the group consisting of SEQ ID NO: 1 to SEQ ID NO: 8, SEQ ID NO: 10 to SEQ ID NO: 15, a fragment thereof, and a sequence having at least 80% sequence identity thereto, particularly selected from the group consisting of SEQ ID NO: 1, SEQ ID NO: 2, SEQ ID NO: 4 to SEQ ID NO: 8, SEQ ID NO: 10 to SEQ ID NO: 15, a fragment thereof, and a sequence having at least 80% sequence identity thereto. In addition, in case of miRNAs having nucleotide sequences according to SEQ ID NO: 3, SEQ ID NO: 9, a fragment thereof, or a sequence having at least 80% sequence identity thereto, it is preferred that the level of these miRNA is only determined together with the level of at least one further miRNA having a nucleotide sequence selected from the group consisting of SEQ ID NO: 1, SEQ ID NO: 2, SEQ ID NO: 4 to SEQ ID NO: 8, SEQ ID NO: 10 to SEQ ID NO: 15, a fragment thereof, and a sequence having at least 80% sequence identity thereto. Other preferred miRNA combinations are listed in FIG. 8.

In a preferred embodiment of the second aspect of the invention, the method aims at determining whether the multiple sclerosis (MS) in the patient improves, exacerbates or is stable.

Preferably, the level of the at least one miRNA, e.g. 1, 2, 3, 4, 5, 6, 7, 8, 9, 10, 11, 12, 13, 14, or 15 miRNA(s), in the test sample is compared to a reference level of the (said) at least one miRNA. Thus, in a preferred embodiment, the method of monitoring the course of multiple sclerosis (MS) comprises the steps of:
(i) determining the level of at least one miRNA, e.g. 1, 2, 3, 4, 5, 6, 7, 8, 9, 10, 11, 12, 13, 14, or 15 miRNA(s), in a test sample isolated from the patient, wherein the nucleotide sequence of the at least one miRNA is selected from the group consisting of SEQ ID NO: 1 to SEQ ID NO: 15, a fragment thereof, and a sequence having at least 80% sequence identity thereto, and
(ii) comparing the level of the at least one miRNA in the test sample to a reference level of the (said) at least one miRNA, e.g. 1, 2, 3, 4, 5, 6, 7, 8, 9, 10, 11, 12, 13, 14, or 15 miRNA(s),
particularly, wherein the method aims at determining whether the multiple sclerosis (MS) in the patient improves, exacerbates or is stable In a preferred embodiment, the reference level is the level of the (said) at least one miRNA, e.g. 1, 2, 3, 4, 5, 6, 7, 8, 9, 10, 11, 12, 13, 14, or 15 miRNA(s), determined empirically by measuring a number of reference samples, preferably at least two reference samples, more preferably at least 2 to 40 reference samples, even more preferably at least 10 to 60 reference samples, and most preferably at least 50 to 100 reference samples, e.g. at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 reference samples, from (different) patients. Preferably or alternatively, said reference level is an average level. The average level is particularly determined by measuring a number of reference samples, preferably at least two reference samples, more preferably at least 2 to 40 reference samples, even more preferably at least 10 to 60 reference samples, and most preferably at least 50 to 100 reference samples, e.g. at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 reference samples, from a number of patients and calculating the "middle" value (e.g. median or mean value) of the reference levels determined therein. Said reference samples are preferably samples from multiple sclerosis (MS) patients, e.g. relapsing-remitting multiple sclerosis (RR-MS), secondary progressive multiple sclerosis (SPMS), progressive relapsing multiple sclerosis (PRMS), or primary progressive multiple sclerosis (PPMS) patients. As to the definition of the term "multiple sclerosis (MS), e.g. RR-MS, SP-MS, PR-MS, or PP-MS, patients", it is referred to the first aspect of the invention.

It is also (alternatively or additionally) preferred that the reference level is determined in a reference sample isolated from the patient, particularly prior to the isolation of the test sample. For example, the reference level is the level of the (said) at least one miRNA, e.g. 1, 2, 3, 4, 5, 6, 7, 8, 9, 10, 11, 12, 13, 14, or 15 miRNA(s), determined empirically by measuring a number of reference samples, particularly at least two reference samples, from patients and the reference level is determined in the reference sample isolated from the patient prior to the isolation of the test sample. Further, for example, the reference level is the level of the (said) at least one miRNA, e.g. 1, 2, 3, 4, 5, 6, 7, 8, 9, 10, 11, 12, 13, 14, or 15 miRNA(s), determined empirically by measuring a number of reference samples, particularly at least two reference samples, from patients, said reference samples are samples from multiple sclerosis patients, e.g. relapsing-remitting multiple sclerosis (RR-MS), secondary progressive multiple sclerosis (SPMS), progressive relapsing multiple sclerosis (PRMS), or primary progressive multiple sclerosis (PPMS) patients, and the reference level is determined in the reference sample isolated from the patient prior to the isolation of the test sample. It is particularly preferred that the reference sample is isolated from the patient in a time period of between 9 months and 1 day or between 6 months and 1 day prior to the isolation of the test sample, it is particularly more preferred that the reference sample is isolated from the patient in a time period of between 3 months and 1 day prior to the isolation of the test sample, it is particularly even more preferred that the reference sample is isolated from the patient in a time period of between 1 month and 1 day prior to the isolation of the test sample, and it is particularly most preferred that the reference sample is isolated from the patient in a time period of between 3 weeks and 1 day prior to the isolation of the test sample, e.g. 1, 2, 3, 4, 5, 6 day(s), 1, 2, 3 4, 5, 6, 7, 8, or 9 month(s) prior to the isolation of the test sample.

In an alternative preferred embodiment, the reference level is the level of the (said) at least one miRNA, e.g. 1, 2, 3, 4, 5, 6, 7, 8, 9, 10, 11, 12, 13, 14, or 15 miRNA(s), determined in a reference sample isolated from the same patient. Particularly, the reference level is determined in a reference sample isolated from the same patient prior to the isolation of the test sample. Preferably, said (multiple sclerosis) patient is a relapsing-remitting multiple sclerosis (RR-MS) patient, secondary progressive multiple sclerosis (SPMS) patient, progressive relapsing multiple sclerosis (PRMS) patient, or primary progressive multiple sclerosis (PPMS) patient. As to the definition of the term "multiple sclerosis (MS), e.g. RR-MS, SP-MS, PR-MS, or PP-MS, patient", it is referred to the first aspect of the invention. For example, the reference level is the level of the (said) at least one miRNA, e.g. 1, 2, 3, 4, 5, 6, 7, 8, 9, 10, 11, 12, 13, 14, or 15 miRNA(s), determined in a reference sample isolated from the same patient, particularly prior to the isolation of the test sample, and said patient is a relapsing-remitting multiple sclerosis (RR-MS) patient, secondary progressive multiple sclerosis (SPMS) patient, progressive relapsing multiple sclerosis (PRMS) patient, or primary progressive multiple sclerosis (PPMS) patient. It is particularly preferred that the reference sample is isolated from the same patient in a time period of between 9 months and 1 day or between 6 months and 1 day prior to the isolation of the test sample, it is particularly more preferred that the reference sample is isolated from the same patient in a time period of between 3 months and 1 day prior to the isolation of the test sample, it is particularly even more preferred that the reference sample is isolated from the same patient in a time period of between 1 month and 1 day prior to the isolation of the test sample, and it is particularly most preferred that the reference sample is isolated from the same patient in a time period of between 3 weeks and 1 day prior to the isolation of the test sample, e.g. 1, 2, 3, 4, 5, 6 day(s), 1, 2, 3 week(s), 1, 2, 3 4, 5, 6, 7, 8, or 9 month(s) prior to the isolation of the test sample.

As to the definition of the terms "test sample" and "reference sample" and as to the preferred embodiments of the "test sample" and "reference sample", it is referred to the first aspect of the invention.

As mentioned above, it is preferred that the level of the at least one miRNA, e.g. 1, 2, 3, 4, 5, 6, 7, 8, 9, 10, 11, 12, 13, 14, or 15 miRNA(s), in the test sample is compared to a reference level of the (said) at least one miRNA. In addition, the preferred embodiments of the reference level and reference sample are described above.

In a preferred embodiment, the nucleotide sequence of the at least one miRNA, e.g. 1, 2, 3, 4, 5, 6, 7, or 8 miRNA(s), is selected from the group consisting of SEQ ID NO: 1 to SEQ ID NO: 8, a fragment thereof, and a sequence having at least 80% sequence identity thereto, preferably SEQ ID NO: 1, SEQ ID NO: 2, SEQ ID NO: 5 to SEQ ID NO: 8, a fragment thereof, and a sequence having at least 80% sequence identity thereto, more preferably SEQ ID NO: 1, SEQ ID NO: 2, a fragment thereof, and a sequence having at least 80% sequence identity thereto, wherein an increase of the level of the at least one miRNA in the test sample when compared to the reference level of the at least one miRNA indicates that multiple sclerosis in the patient improves. More preferably, the miRNAs have nucleotide sequences according to SEQ ID NO: 1, a fragment thereof, or a sequence having at least 80% sequence identity thereto and according to SEQ ID NO: 2, a fragment thereof, or a sequence having at least 80% sequence identity thereto. In a particularly preferred embodiment, the nucleotide sequence of the at least one miRNA, e.g. 1 or 2 miRNA(s), is selected from the group consisting of SEQ ID NO: 3, SEQ ID NO: 4, a fragment thereof, and a sequence having at least 80% sequence identity thereto, wherein an increase of the level of the at least one miRNA in the test sample when compared to the reference level of the at least one miRNA only indicates that multiple sclerosis in the patient improves when the level of at least one miRNA, e.g. 1 or 2 miRNA(s), selected from the group consisting of SEQ ID NO: 1, SEQ ID NO: 2, a fragment thereof, and a sequence having at least 80% sequence identity thereto in the test sample when compared to the reference level of the at least one miRNA is not decreased.

In another preferred embodiment, the nucleotide sequence of the at least one miRNA, e.g. 1, 2, 3, 4, 5, 6, or 7 miRNA(s), is selected from the group consisting of SEQ ID NO: 9 to SEQ ID NO: 15, a fragment thereof, and a sequence having at least 80% sequence identity thereto, preferably SEQ ID NO: 10 to SEQ ID NO: 15, a fragment thereof, and a sequence having at least 80% sequence identity thereto, wherein a decrease of the level of the at least one miRNA in the test sample when compared to the reference level of the at least one miRNA indicates that multiple sclerosis in the patient improves. In a particularly preferred embodiment, the nucleotide sequence of the at least one miRNA is SEQ ID NO: 9, a fragment thereof, and a sequence having at least 80% sequence identity thereto, wherein a decrease of the level of the at least one miRNA in the test sample when compared to the reference level of the at least one miRNA only indicates that multiple sclerosis in the patient improves when the level of at least one miRNA, e.g. 1 or 2 miRNA(s), selected from the group consisting of SEQ ID NO: 1, SEQ ID NO: 2, a fragment thereof, and a sequence having at least 80% sequence identity thereto in the test sample when compared to the reference level of the at least one miRNA is not decreased.

More preferably,
(i) an at least 1.2 fold increase, preferably an at least 1.4 fold increase, of the level of the miRNA having a nucleotide sequence according to SEQ ID NO: 1, an at least 1.2 fold increase, preferably an at least 1.4 fold increase, of the level of the miRNA having a nucleotide sequence according to SEQ ID NO: 2, an at least 1.2 fold increase, preferably an at least 1.4 fold increase, of the level of the miRNA having a nucleotide sequence according to SEQ ID NO: 3, an at least 1.2 fold increase, preferably an at least 1.4 fold increase, of the level of the miRNA having a nucleotide sequence according to SEQ ID NO: 4, an at least 1.2 fold increase, preferably an at least 1.4 fold increase, of the level of the miRNA having a nucleotide sequence according to SEQ ID NO: 5, an at least 1.2 fold increase, preferably an at least 1.4 fold increase, of the level of the miRNA having a nucleotide sequence according to SEQ ID NO: 6, an at least 1.2 fold increase, preferably an at least 1.4 fold increase, of the level of the miRNA having a nucleotide sequence according to SEQ ID NO: 7, and/or an at least 1.2 fold increase, preferably an at least 1.4 fold increase, of the level of the miRNA having a nucleotide sequence according to SEQ ID NO: 8 indicates that multiple sclerosis in the patient improves, and/or
(ii) an at least 1.2 fold decrease, preferably an at least 1.4 fold decrease, of the level of the miRNA having a nucleotide sequence according to SEQ ID NO: 9, an at least 1.2 fold decrease, preferably an at least 1.4 fold decrease, of the level of the miRNA having a nucleotide sequence according to SEQ ID NO: 10, an at least 1.2 fold decrease, preferably an at least 1.4 fold decrease, of the level of the miRNA having a nucleotide sequence according to SEQ ID NO: 11, an at least 1.2 fold decrease, preferably an at least 1.4 fold decrease, of the level of the miRNA having a nucleotide sequence according to SEQ ID NO: 12, an at least 1.2 fold decrease, preferably an at least 1.4 fold decrease, of the level of the miRNA having a nucleotide sequence according to SEQ ID NO: 13, an at least 1.2 fold decrease, preferably an at least 1.4 fold decrease, of the level of the miRNA having a nucleotide sequence according to SEQ ID NO: 14, and/or an at least 1.2 fold decrease, preferably an at least 1.4 fold decrease, of the level of the miRNA having a nucleotide sequence according to SEQ ID NO: 15 indicates that multiple sclerosis in the patient improves.

In a further preferred embodiment, the nucleotide sequence of the at least one miRNA, e.g. 1, 2, 3, 4, 5, 6, 7, or 8 miRNA(s), is selected from the group consisting of SEQ ID NO: 1 to SEQ ID NO: 8, a fragment thereof, and a sequence having at least 80% sequence identity thereto, preferably SEQ ID NO: 1, SEQ ID NO: 2, SEQ ID NO: 5 to SEQ ID NO: 8, a fragment thereof, and a sequence having at least 80% sequence identity thereto, more preferably SEQ ID NO: 1, SEQ ID NO: 2, a fragment thereof, and a sequence having at least 80% sequence identity thereto, wherein a non-alteration of the level of the at least one miRNA in the test sample when compared to the reference level of the at least one miRNA indicates that multiple sclerosis in the patient is stable. More preferably, the miRNAs have nucleotide sequences according to SEQ ID NO: 1, a fragment thereof, or a sequence having at least 80% sequence identity thereto and according to SEQ ID NO: 2, a fragment thereof, or a sequence having at least 80% sequence identity thereto. In a particularly preferred embodiment, the nucleotide sequence of the at least one miRNA, e.g. 1 or 2 miRNA(s), is selected from the group consisting of SEQ ID NO: 3, SEQ ID NO: 4, a fragment thereof, and a sequence having at least 80% sequence identity thereto, wherein a non-alteration of the level of the at least one miRNA in the test sample when compared to the reference level of the at least one miRNA only indicates that multiple sclerosis in the patient is stable when the level of at least one miRNA, e.g. 1 or 2 miRNA(s), selected from the group consisting of SEQ ID NO: 1, SEQ ID NO: 2, a fragment thereof, and a sequence having at least 80% sequence identity thereto in the test sample when compared to the reference level of the at least one miRNA is not altered.

In another further preferred embodiment, the nucleotide sequence of the at least one miRNA, e.g. 1, 2, 3, 4, 5, 6, or 7 miRNA(s), is selected from the group consisting of SEQ ID NO: 9 to SEQ ID NO: 15, a fragment thereof, and a sequence having at least 80% sequence identity thereto, preferably SEQ ID NO: 10 to SEQ ID NO: 15, a fragment thereof, and a sequence having at least 80% sequence identity thereto, wherein a non-alteration of the level of the at least one miRNA in the test sample when compared to the reference level of the at least one miRNA indicates that multiple sclerosis in the patient is stable. In a particularly preferred embodiment, the nucleotide sequence of the at least one miRNA is SEQ ID NO: 9, a fragment thereof, and a sequence having at least 80% sequence identity thereto, wherein a non-alteration of the level of the at least one miRNA in the test sample when compared to the reference level of the at least one miRNA only indicates that multiple sclerosis in the patient is stable when the level of at least one miRNA, e.g. 1 or 2 miRNA(s), selected from the group consisting of SEQ ID NO: 1, SEQ ID NO: 2, a fragment thereof, and a sequence having at least 80% sequence identity thereto in the test sample when compared to the reference level of the at least one miRNA is not altered.

The term "that the level of the at least one miRNA in the test sample when compared to the reference level of the at least one miRNA is not altered" may mean that the level of the at least one miRNA in the test sample when compared to the reference level varies between >0 to 20%, preferably between >0 to 10%, and more preferably between >0 to 5% or between >0 to 3%, e.g. 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, or 20%. Most preferably, the level of the at least ne miRNA in the test sample when compared to the reference level does not vary or is constant.

In an additional preferred embodiment, the nucleotide sequence of the at least one miRNA, e.g. 1, 2, 3, 4, 5, 6, 7, or 8 miRNA(s), is selected from the group consisting of SEQ ID NO: 1 to SEQ ID NO: 8, a fragment thereof, and a sequence having at least 80% sequence identity thereto, preferably SEQ ID NO: 1, SEQ ID NO: 2, SEQ ID NO: 5 to SEQ ID NO: 8, a fragment thereof, and a sequence having at least 80% sequence identity thereto, more preferably SEQ ID NO: 1, SEQ ID NO: 2, a fragment thereof, and a sequence having at least 80% sequence identity thereto, wherein a decrease of the level of the at least one miRNA in the test sample when compared to the reference level of the at least one miRNA indicates that multiple sclerosis in the patient exacerbates. More preferably, the miRNAs have nucleotide sequences according to SEQ ID NO: 1, a fragment thereof, or a sequence having at least 80% sequence identity thereto and according to SEQ ID NO: 2, a fragment thereof, or a sequence having at least 80% sequence identity thereto. In a particularly preferred embodiment, the nucleotide sequence of the at least one miRNA, e.g. 1 or 2 miRNA(s), is selected from the group consisting of SEQ ID NO: 3, SEQ ID NO: 4, a fragment thereof, and a sequence having at least 80% sequence identity thereto, wherein a decrease of the level of the at least one miRNA in the test sample when compared to the reference level of the at least one miRNA only indicates that multiple sclerosis in the patient exacerbates when the level of at least one miRNA, e.g. 1 or 2 miRNA(s), selected from the group consisting of SEQ ID NO: 1, SEQ ID NO: 2, a fragment thereof, and a sequence having at least 80% sequence identity thereto in the test sample when compared to the reference level of the at least one miRNA is not increased.

In another additional preferred embodiment, the nucleotide sequence of the at least one miRNA, e.g. 1, 2, 3, 4, 5, 6, or 7 miRNA(s), is selected from the group consisting of SEQ ID NO: 9 to SEQ ID NO: 15, a fragment thereof, and a sequence having at least 80% sequence identity thereto, preferably SEQ ID NO: 10 to SEQ ID NO: 15, a fragment thereof, and a sequence having at least 80% sequence identity thereto, wherein an increase of the level of the at least one miRNA in the test sample when compared to the reference level of the at least one miRNA indicates that multiple sclerosis in the patient exacerbates. In a particularly preferred embodiment, the nucleotide sequence of the at least one miRNA is SEQ ID NO: 9, a fragment thereof, and a sequence having at least 80% sequence identity thereto, wherein an increase of the level of the at least one miRNA in the test sample when compared to the reference level of the at least one miRNA only indicates that multiple sclerosis in the patient exacerbates when the level of at least one miRNA e.g. 1 or 2 miRNA(s), selected from the group consisting of SEQ ID NO: 1, SEQ ID NO: 2, a fragment thereof, and a sequence having at least 80% sequence identity thereto in the test sample when compared to the reference level of the at least one miRNA is not increased.

The above method is a method which aims at determining whether multiple sclerosis (MS) in the patient improves, exacerbates or is stable. In a preferred embodiment of the above method, the patient is a patient which receives or has received a therapeutic treatment of multiple sclerosis. Preferably, said therapeutic treatment involves the application/administration of a drug for multiple sclerosis. Said drug may be selected from the group consisting of natalizumab, interferon beta 1a, interferon beta 1b, glatiramer acetate, alemtuzumab, fingolimod, dimethylfumarate, and mitoxantrone. The drug natalizumab is particularly preferred.

If the patient is a patient which receives or has received a therapeutic treatment of multiple sclerosis, the above method preferably further comprises the step of administering (i) a renewed dose of the drug when multiple sclerosis in said patient is stable, (ii) a dose which is increased compared to the previously administered dose of the drug when multiple sclerosis in said patient exacerbates, or (iii) a renewed dose of the drug or a dose which is decreased compared to the previously administered dose of the drug when multiple sclerosis in said patient improves. When multiple sclerosis in said patient exacerbates, the drug may also be changed, i.e. another drug (e.g. selected from the group consisting of natalizumab, interferon beta 1a, interferon beta 1b, glatiramer acetate, alemtuzumab, fingolimod, dimethylfumarate, and mitoxantrone) may be administered. Alternatively, if the patient is a patient which receives or has received a therapeutic treatment of multiple sclerosis, the above method preferably further comprises the step of continuing the treatment of multiple sclerosis when multiple sclerosis in said patient is stable or improves, or discontinuing the treatment of multiple sclerosis when multiple sclerosis in said patient exacerbates. In the latter case, the administered drug may be changed, i.e. another drug (e.g. selected from the group consisting of natalizumab, interferon beta 1a, interferon beta 1b, glatiramer acetate, alemtuzumab, fingolimod, dimethylfumarate, and mitoxantrone) may be administered.

In another preferred embodiment of the second aspect of the invention, the method aims at determining whether the patient benefits from a therapeutic treatment of multiple sclerosis. Preferably, the patient receives or has received a therapeutic treatment of multiple sclerosis. More preferably, the method aims at determining whether the patient benefits from a therapeutic treatment of multiple sclerosis, wherein the patient receives or has received a therapeutic treatment of multiple sclerosis. It is particularly preferred that said therapeutic treatment involves the application/administration of a drug for multiple sclerosis. Said drug may be selected from the group consisting of natalizumab, interferon beta 1a, interferon beta 1b, glatiramer acetate, alemtuzumab, fingolimod, dimethylfumarate, and mitoxantrone. It is more particularly preferred that said drug is natalizumab.

Preferably, the level of the at least one miRNA in the test sample is compared to a reference level of the (said) at least one miRNA. Thus, in a preferred embodiment, the method of monitoring the course of multiple sclerosis (MS) comprises the steps of:
(i) determining the level of at least one miRNA, e.g. 1, 2, 3, 4, 5, 6, 7, 8, 9, 10, 11, 12, 13, 14 or 15 miRNA(s), in a test sample isolated from the patient, wherein the nucleotide sequence of the at least one miRNA is selected from the group consisting of SEQ ID NO: 1 to SEQ ID NO: 15, a fragment thereof, and a sequence having at least 80% sequence identity thereto, and
(ii) comparing the level of the at least one miRNA in the test sample to a reference level of the (said) at least one miRNA, e.g. 1, 2, 3, 4, 5, 6, 7, 8, 9, 10, 11, 12, 13, 14, or 15 miRNA(s), particularly, wherein the method aims at determining whether the patient benefits from a therapeutic treatment of multiple sclerosis. Preferably, the patient receives or has received a therapeutic treatment of multiple sclerosis. It is particularly preferred that said therapeutic treatment involves the application/administration of a drug for multiple sclerosis. Said drug may be selected from the group consisting of natalizumab, interferon beta 1a, interferon beta 1b, glatiramer acetate, alemtuzumab, fingolimod, dimethylfumarate, and mitoxantrone. It is more particularly preferred that said drug is natalizumab.

In a preferred embodiment, the reference level is the level of the (said) at least one miRNA, e.g. 1, 2, 3, 4, 5, 6, 7, 8, 9, 10, 11, 12, 13, 14, or 15 miRNA(s), determined empirically by measuring a number of reference samples, preferably at least two reference samples, more preferably at least 2 to 40 reference samples, even more preferably at least 10 to 60 reference samples, and most preferably at least 50 to 100 reference samples, e.g. at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 reference samples, from (different) patients. Preferably or alternatively, said reference level is an average level. The average level is particularly determined by measuring a number of reference samples, preferably at least two reference samples, more preferably at least 2 to 40 reference samples, even more preferably at least 10 to 60 reference samples, and most preferably at least 50 to 100 reference samples, e.g. at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 reference samples, from a number of patients and calculating the "middle" value (e.g. median or mean value) of the reference levels determined therein. Said reference samples are preferably samples from multiple sclerosis (MS) patients, e.g. relapsing-remitting multiple sclerosis (RR-MS), secondary progressive multiple sclerosis (SPMS), progressive relapsing multiple sclerosis (PRMS), or primary progressive multiple sclerosis (PPMS) patients. As to the definition of the term "multiple sclerosis (MS), e.g. RR-MS, SP-MS, PR-MS, or PP-MS, patients", it is referred to the first aspect of the invention.

It is also (alternatively or additionally) preferred that the reference level is determined in a reference sample isolated from the patient, particularly prior to the isolation of the test sample. For example, the reference level is the level of the (said) at least one miRNA, e.g. 1, 2, 3, 4, 5, 6, 7, 8, 9, 10, 11, 12, 13, 14, or 15 miRNA(s), determined empirically by measuring a number of reference samples, particularly at least two reference samples, from patients and the reference level is determined in the reference sample isolated from the patient prior to the isolation of the test sample. Further, for example, the reference level is the level of the (said) at least one miRNA, e.g. 1, 2, 3, 4, 5, 6, 7, 8, 9, 10, 11, 12, 13, 14, or 15 miRNA(s), determined empirically by measuring a number of reference samples, particularly at least two reference samples, from patients, said reference samples are samples from multiple sclerosis patients, e.g. relapsing-remitting multiple sclerosis (RR-MS), secondary progressive multiple sclerosis (SPMS), progressive relapsing multiple sclerosis (PRMS), or primary progressive multiple sclerosis (PPMS) patients, and the reference level is determined in the reference sample isolated from the patient prior to the isolation of the test sample.

It is further preferred that the reference sample is isolated from the patient in a time period of between 9 months and 1 day or between 6 months and 1 day prior to the isolation of the test sample, it is more preferred that the reference sample is isolated from the patient in a time period of between 3 months and 1 day prior to the isolation of the test sample, it is even more preferred that the reference sample is isolated from the patient in a time period of between 1 month and 1 day prior to the isolation of the test sample, and it is most preferred that the reference sample is isolated from the patient in a time period of between 3 weeks and 1 day prior to the isolation of the test sample, e.g. 1, 2, 3, 4, 5, 6 day(s), 1, 2, 3 week(s), 1, 2, 3 4, 5, 6, 7, 8, or 9 month(s) prior to the isolation of the test sample.

It is particularly preferred that said reference sample is isolated prior to the therapeutic treatment of multiple sclerosis and said test sample is isolated after the therapeutic treatment or during a therapeutic treatment of multiple sclerosis.

It is also particularly preferred that said reference sample is isolated after the initiation of the therapeutic treatment of multiple sclerosis and said test sample is isolated after the therapeutic treatment or during a therapeutic treatment of multiple sclerosis.

It is particularly more preferred that the reference sample is isolated in a time period of between 3 months and immediately prior to the therapeutic treatment of multiple sclerosis, particularly by administration of a drug for multiple sclerosis, it is particularly even more preferred that the reference sample is isolated in a time period of between 3 weeks and immediately prior to the therapeutic treatment of multiple sclerosis, particularly by administration of a drug for multiple sclerosis, and it is particularly most preferred that the reference sample is isolated in a time period of between 1 day and immediately prior to the therapeutic treatment of multiple sclerosis, particularly by administration of a drug for multiple sclerosis, or between 1 hour and immediately prior to the therapeutic treatment of multiple sclerosis, particularly by administration of a drug for multiple sclerosis, e.g. immediately, 10, 20, 30, 40, 50 minutes, 1, 2, 3, 4, 5, 6, 7, 8, 9, 10, 11, 12, 13, 14, 15, 16, 17, 18, 19, 20, 21, 22, 23 hour(s), 1, 2, 3, 4, 5, 6 day(s), 1, 2, 3 week(s), 1, 2, or 3 month(s) prior to the therapeutic treatment of multiple sclerosis, particularly by administration of a drug for multiple sclerosis.

It is further (alternatively or additionally) particularly more preferred that the reference sample is isolated in a time period of between 3 months and immediately after the initiation of the therapeutic treatment, particularly by administration of a drug for multiple sclerosis, it is particularly even more preferred that the reference sample is isolated in a time period of between 3 weeks and immediately after the initiation of the therapeutic treatment, particularly by administration of a drug for multiple sclerosis, and it is particularly most preferred that the reference sample is isolated in a time period of between 1 day and immediately after the initiation of the therapeutic treatment, particularly by administration of a drug for multiple sclerosis, or between 1 hour and immediately after the initiation of the therapeutic treatment, particularly by administration of a drug for multiple sclerosis, e.g. immediately, 10, 20, 30, 40, 50 minutes, 1, 2, 3, 4, 5, 6, 7, 8, 9, 10, 11, 12, 13, 14, 15, 16, 17, 18, 19, 20, 21, 22, 23 hour(s), 1, 2, 3, 4, 5, 6 day(s), 1, 2, 3 week(s), 1, 2, or 3 month(s) after the initiation of the therapeutic treatment, particularly by administration of a drug for multiple sclerosis.

It is also (alternatively or additionally) particularly more preferred that the test sample is isolated in a time period of between 6 months and immediately after the therapeutic treatment, particularly by administration of a drug for multiple sclerosis, or between 3 months and immediately after the therapeutic treatment, particularly by administration of a drug for multiple sclerosis, it is particularly even more preferred that the test sample is isolated in a time period of between 3 weeks and immediately after the therapeutic treatment, particularly by administration of a drug for multiple sclerosis, and it is particularly most preferred that the test sample is isolated in a time period of between 1 day and immediately after the therapeutic treatment, particularly by administration of a drug for multiple sclerosis, or between 1 hour and immediately after the therapeutic treatment, particularly by administration of a drug for multiple sclerosis, e.g. immediately, 10, 20, 30, 40, 50 minutes, 1, 2, 3, 4, 5, 6, 7, 8, 9, 10, 11, 12, 13, 14, 15, 16, 17, 18, 19, 20, 21, 22, 23 hour(s), 1, 2, 3, 4, 5, 6 day(s), 1, 2, 3 week(s), 1, 2, 3, 4, 5, or 6 month(s) after the therapeutic treatment, particularly by administration of a drug for multiple sclerosis.

In an alternative preferred embodiment, the reference level is the level of the (said) at least one miRNA, e.g. 1, 2, 3, 4, 5, 6, 7, 8, 9, 10, 11, 12, 13, 14, or 15 miRNA(s), determined in a reference sample isolated from the same patient. Particularly, the reference level is determined in a reference sample isolated from the same patient prior to the isolation of the test sample. Preferably, said (multiple sclerosis) patient is a relapsing-remitting multiple sclerosis (RR-MS) patient, secondary progressive multiple sclerosis (SPMS) patient, progressive relapsing multiple sclerosis (PRMS) patient, or primary progressive multiple sclerosis (PPMS) patient. As to the definition of the term "multiple sclerosis (MS), e.g. RR-MS, SP-MS, PR-MS, or PP-MS, patient", it is referred to the first aspect of the invention. For example, the reference level is the level of the (said) at least one miRNA, e.g. 1, 2, 3, 4, 5, 6, 7, 8, 9, 10, 11, 12, 13, 14, or 15 miRNA(s), determined in a reference sample isolated from the same patient, particularly prior to the isolation of the test sample, and said patient is a relapsing-remitting multiple sclerosis (RR-MS) patient, secondary progressive multiple sclerosis (SPMS) patient, progressive relapsing multiple sclerosis (PRMS) patient, or primary progressive multiple sclerosis (PPMS) patient.

It is further preferred that the reference sample is isolated from the same patient in a time period of between 9 months and 1 day or between 6 months and 1 day prior to the isolation of the test sample, it is more preferred that the reference sample is isolated from the same patient in a time period of between 3 months and 1 day prior to the isolation of the test sample, it is even more preferred that the reference sample is isolated from the same patient in a time period of between 1 month and 1 day prior to the isolation of the test sample, and it is most preferred that the reference sample is isolated from the same patient in a time period of between 3 weeks and 1 day prior to the isolation of the test sample, e.g. 1, 2, 3, 4, 5, 6 day(s), 1, 2, 3 week(s), 1, 2, 3 4, 5, 6, 7, 8, or 9 month(s) prior to the isolation of the test sample.

It is particularly preferred that said reference sample is isolated prior to the therapeutic treatment of multiple sclerosis and said test sample is isolated after the therapeutic treatment or during a therapeutic treatment of multiple sclerosis, particularly from the same patient.

It is also particularly preferred that said reference sample is isolated after the initiation of the therapeutic treatment of multiple sclerosis and said test sample is isolated after the therapeutic treatment or during a therapeutic treatment of multiple sclerosis, particularly from the same patient.

It is particularly more preferred that the reference sample is isolated in a time period of between 3 months and immediately prior to the therapeutic treatment of multiple sclerosis, particularly by administration of a drug for multiple sclerosis, it is particularly even more preferred that the reference sample is isolated in a time period of between 3 weeks and immediately prior to the therapeutic treatment of multiple sclerosis, particularly by administration of a drug for multiple sclerosis, and it is particularly most preferred that the reference sample is isolated in a time period of between 1 day and immediately prior to the therapeutic treatment of multiple sclerosis, particularly by administration of a drug for multiple sclerosis, or between 1 hour and immediately prior to the therapeutic treatment of multiple sclerosis, particularly by administration of a drug for multiple sclerosis, e.g. immediately, 10, 20, 30, 40, 50 minutes, 1, 2, 3, 4, 5, 6, 7, 8, 9, 10, 11, 12, 13, 14, 15, 16, 17, 18, 19, 20, 21, 22, 23 hour(s), 1, 2, 3, 4, 5, 6 day(s), 1, 2, 3 week(s), 1, 2, or 3 month(s) prior to the therapeutic treatment of multiple sclerosis, particularly by administration of a drug for multiple sclerosis.

It is further (alternatively or additionally) particularly more preferred that the reference sample is isolated in a time period of between 3 months and immediately after the initiation of the therapeutic treatment, particularly by administration of a drug for multiple sclerosis, it is particularly even more preferred that the reference sample is isolated in a time period of between 3 weeks and immediately after the initiation of the therapeutic treatment, particularly by administration of a drug for multiple sclerosis, and it is particularly most preferred that the reference sample is isolated in a time period of between 1 day and immediately after the initiation of the therapeutic treatment, particularly by administration of a drug for multiple sclerosis, or between 1 hour and immediately after the initiation of the therapeutic treatment, particularly by administration of a drug for multiple sclerosis, e.g. immediately, 10, 20, 30, 40, 50 minutes, 1, 2, 3, 4, 5, 6, 7, 8, 9, 10, 11, 12, 13, 14, 15, 16, 17, 18, 19, 20, 21, 22, 23 hour(s), 1, 2, 3, 4, 5, 6 day(s), 1, 2, 3 week(s), 1, 2, or 3 month(s) after the initiation of the therapeutic treatment, particularly by administration of a drug for multiple sclerosis.

It is also (alternatively or additionally) particularly more preferred that the test sample is isolated in a time period of between 6 months and immediately after the therapeutic treatment, particularly by administration of a drug for multiple sclerosis, or between 3 months and immediately after the therapeutic treatment, particularly by administration of a drug for multiple sclerosis, it is particularly even more preferred that the test sample is isolated in a time period of between 3 weeks and immediately after the therapeutic treatment, particularly by administration of a drug for multiple sclerosis, and it is particularly most preferred that the test sample is isolated in a time period of between 1 day and immediately after the therapeutic treatment, particularly by administration of a drug for multiple sclerosis, or between 1 hour and immediately after the therapeutic treatment, particularly by administration of a drug for multiple sclerosis, e.g. immediately, 10, 20, 30, 40, 50 minutes, 1, 2, 3, 4, 5, 6, 7, 8, 9, 10, 11, 12, 13, 14, 15, 16, 17, 18, 19, 20, 21, 22, 23 hour(s), 1, 2, 3, 4, 5, 6 day(s), 1, 2, 3 week(s), 1, 2, 3, 4, 5, or 6 month(s) after the therapeutic treatment, particularly by administration of a drug for multiple sclerosis.

As to the definition of the terms "test sample" and "reference sample" and as to the preferred embodiments of the "test sample" and "reference sample", it is referred to the first aspect of the invention.

As mentioned above, it is preferred that the level of the at least one miRNA, e.g. 1, 2, 3, 4, 5, 6, 7, 8, 9, 10, 11, 12, 13, 14, or 15 miRNA(s), in the test sample is compared to a reference level of the (said) at least one miRNA. In addition, the preferred embodiments of the reference level and reference sample are described above.

In a preferred embodiment, the nucleotide sequence of the at least one miRNA, e.g. 1, 2, 3, 4, 5, 6, 7, or 8 miRNA(s), is selected from the group consisting of SEQ ID NO: 1 to SEQ ID NO: 8, a fragment thereof, and a sequence having at least 80% sequence identity thereto, preferably SEQ ID NO: 1, SEQ ID NO: 2, SEQ ID NO: 5 to SEQ ID NO: 8, a fragment thereof, and a sequence having at least 80% sequence identity thereto, more preferably SEQ ID NO: 1, SEQ ID NO: 2, a fragment thereof, and a sequence having at least 80% sequence identity thereto, wherein an increase of the level of the at least one miRNA in the test sample when compared to the reference level of the at least one miRNA indicates that the patient benefits from said treatment of multiples sclerosis. More preferably, the miRNAs have nucleotide sequences according to SEQ ID NO: 1, a fragment thereof, or a sequence having at least 80% sequence identity thereto and according to SEQ ID NO: 2, a fragment thereof, or a sequence having at least 80% sequence identity thereto. In a particularly preferred embodiment, the nucleotide sequence of the at least one miRNA, e.g. 1 or 2 miRNA(s), is selected from the group consisting of SEQ ID NO: 3, SEQ ID NO: 4, a fragment thereof, and a sequence having at least 80% sequence identity thereto, wherein an increase of the level of the at least one miRNA in the test sample when compared to the reference level of the at least one miRNA only indicates that the patient benefits from said treatment of multiples sclerosis when the level of at least one miRNA, e.g. 1 or 2 miRNA(s), selected from the group consisting of SEQ ID NO: 1, SEQ ID NO: 2, a fragment thereof, and a sequence having at least 80% sequence identity thereto in the test sample when compared to the reference level of the at least one miRNA is not decreased.

In another preferred embodiment, the nucleotide sequence of the at least one miRNA, e.g. 1 or 2 miRNA(s), is selected from the group consisting of SEQ ID NO: 1, SEQ ID NO: 2, a fragment thereof, and a sequence having at least 80% sequence identity thereto, wherein a decrease of the level of the at least one miRNA in the test sample when compared to the reference level of the at least one miRNA indicates that the patient does not benefit from said treatment of multiples sclerosis. More preferably, the miRNAs have nucleotide sequences according to SEQ ID NO: 1, a fragment thereof, or a sequence having at least 80% sequence identity thereto and according to SEQ ID NO: 2, a fragment thereof, or a sequence having at least 80% sequence identity thereto.

In a further preferred embodiment, the nucleotide sequence of the at least one miRNA, e.g. 1, 2, 3, 4, 5, 6, or 7 miRNA(s), is selected from the group consisting of SEQ ID NO: 9 to SEQ ID NO: 15, a fragment thereof, and a sequence having at least 80% sequence identity thereto, preferably SEQ ID NO: 10 to SEQ ID NO: 15, a fragment thereof, and a sequence having at least 80% sequence identity thereto, wherein a decrease of the level of the at least one miRNA in the test sample when compared to the reference level of the at least one miRNA indicates that the patient benefits from said treatment of multiples sclerosis. In a particularly preferred embodiment, the nucleotide sequence of the at least one miRNA is SEQ ID NO: 9, a fragment thereof, and a sequence having at least 80% sequence identity thereto, wherein a decrease of the level of the at least one miRNA in the test sample when compared to the reference level of the at least one miRNA only indicates that the patient benefits from said treatment of multiples sclerosis when the level of at least one miRNA, e.g. 1 or 2 miRNA(s), selected from the group consisting of SEQ ID NO: 1, SEQ ID NO: 2, a fragment thereof, and a sequence having at least 80% sequence identity thereto in the test sample when compared to the reference level of the at least one miRNA is not decreased.

More preferably, (i) an at least 1.2 fold increase, preferably an at least 1.4 fold increase, of the level of the miRNA having a nucleotide sequence according to SEQ ID NO: 1, an at least 1.2 fold increase, preferably an at least 1.4 fold increase, of the level of the miRNA having a nucleotide sequence according to SEQ ID NO: 2, an at least 1.2 fold increase, preferably an at least 1.4 fold increase, of the level of the miRNA having a nucleotide sequence according to SEQ ID NO: 3, an at least 1.2 fold increase, preferably an at least 1.4 fold increase, of the level of the miRNA having a nucleotide sequence according to SEQ ID NO: 4, an at least 1.2 fold increase, preferably an at least 1.4 fold increase, of the level of the miRNA having a nucleotide sequence according to SEQ ID NO: 5, an at least 1.2 fold increase, preferably an at least 1.4 fold increase, of the level of the miRNA having a nucleotide sequence according to SEQ ID NO: 6, an at least 1.2 fold increase, preferably an at least 1.4 fold increase, of the level of the miRNA having a nucleotide sequence according to SEQ ID NO: 7, and/or an at least 1.2 fold increase, preferably an at least 1.4 fold increase, of the level of the miRNA having a nucleotide sequence according to SEQ ID NO: 8 indicates that the patient benefits from said treatment of multiples sclerosis, and/or (ii) an at least 1.2 fold decrease, preferably an at least 1.4 fold decrease, of the level of the miRNA having a nucleotide sequence according to SEQ ID NO: 9, an at least 1.2 fold decrease, preferably an at least 1.4 fold decrease, of the level of the miRNA having a nucleotide sequence according to SEQ ID NO: 10, an at least 1.2 fold decrease, preferably an at least 1.4 fold decrease, of the level of the miRNA having a nucleotide sequence according to SEQ ID NO: 11, an at least 1.2 fold decrease, preferably an at least 1.4 fold decrease, of the level of the miRNA having a nucleotide sequence according to SEQ ID NO: 12, an at least 1.2 fold decrease, preferably an at least 1.4 fold decrease, of the level of the miRNA having a nucleotide sequence according to SEQ ID NO: 13, an at least 1.2 fold decrease, preferably an at least 1.4 fold decrease, of the level of the miRNA having a nucleotide sequence according to SEQ ID NO: 14, and/or an at least 1.2 fold decrease, preferably an at least 1.4 fold decrease, of the level of the miRNA having a nucleotide sequence according to SEQ ID NO: 15 indicates that the patient benefits from said treatment of multiples sclerosis.

The above method is a method which aims at determining whether the patient benefits from a therapeutic treatment of multiple sclerosis. Said patient may be a patient which receives or has received a therapeutic treatment of multiple sclerosis. Said therapeutic treatment may involve the application/administration of a drug for multiple sclerosis. Said drug may be selected from the group consisting of natalizumab, interferon beta 1a, interferon beta 1b, glatiramer acetate, alemtuzumab, fingolimod, dimethylfumarate, and mitoxantrone. In a preferred embodiment, the above method further comprises the step of administering a renewed dose of the drug when the patient benefits from said treatment of multiple sclerosis, or administering a dose of the drug which is increased compared to the previously administered dose of the drug when the patient does not benefit from said treatment of multiple sclerosis. Alternatively, when the patient does not benefit from said treatment of multiple sclerosis, the administered drug may be changed, i.e. another drug (e.g. selected from the group consisting of natalizumab, interferon beta 1a, interferon beta 1b, glatiramer acetate, alemtuzumab, fingolimod, dimethylfumarate, and mitoxantrone) may be administered. In another preferred embodiment, the above method further comprises the step of continuing the treatment of multiple sclerosis when the patient benefits from said treatment, or discontinuing the treatment of multiple sclerosis when the patient does not benefit from said treatment. In the latter case, the administered drug may be changed (i.e. another drug e.g. selected from the group consisting of natalizumab, interferon beta 1a, interferon beta 1b, glatiramer acetate, alemtuzumab, fingolimod, dimethylfumarate, and mitoxantrone may be administered) and particularly, the benefit of the patient to the therapeutic treatment of multiple sclerosis may be retested.

In an additional preferred embodiment of the second aspect of the invention, the method aims at determining whether multiple sclerosis in the patient further improves, again exacerbates or is stable. Preferably, the patient receives or has received a successful therapeutic treatment of multiple sclerosis. More preferably, the method aims at determining whether multiple sclerosis in the patient further improves, again exacerbates or is stable, wherein the patient receives or has received a successful therapeutic treatment of multiple sclerosis. It is particularly preferred that said therapeutic treatment involves the application/administration of a drug for multiple sclerosis. Said drug may be selected from the group consisting of natalizumab, interferon beta 1a, interferon beta 1b, glatiramer acetate, alemtuzumab, fingolimod, dimethylfumarate, and mitoxantrone. It is more particularly preferred that said drug is natalizumab.

Preferably, the level of the at least one miRNA, e.g. 1, 2, 3, 4, 5, 6, 7, 8, 9, 10, 11, 12, 13, 14, or 15 miRNA(s), in the test sample is compared to a reference level of the (said) at least one miRNA. Thus, in a preferred embodiment, the method of monitoring the course of multiple sclerosis (MS) comprises the steps of:

(i) determining the level of at least one miRNA, e.g. 1, 2, 3, 4, 5, 6, 7, 8, 9, 10, 11, 12, 13, 14, or 15 miRNA(s), in a test sample isolated from the patient, wherein the nucleotide sequence of the at least one miRNA is selected from the group consisting of SEQ ID NO: 1 to SEQ ID NO: 15, a fragment thereof, and a sequence having at least 80% sequence identity thereto, and (ii) comparing the level of the at least one miRNA in the test sample to a reference level of the (said) at least one miRNA, e.g. 1, 2, 3, 4, 5, 6, 7, 8, 9, 10, 11, 12, 13, 14, or 15 miRNA(s), particularly, wherein the method aims at determining whether multiple sclerosis in the patient further improves, again exacerbates or is stable. Preferably, the patient receives or has received a successful therapeutic treatment of multiple sclerosis. It is particularly preferred that said therapeutic treatment involves the application/administration of a drug for multiple sclerosis. Said drug may be selected from the group consisting of natalizumab, interferon beta 1a, interferon beta 1b, glatiramer acetate, alemtuzumab, fingolimod, dimethylfumarate, and mitoxantrone. It is more particularly preferred that said drug is natalizumab.

In a preferred embodiment, the reference level is the level of the (said) at least one miRNA, e.g. 1, 2, 3, 4, 5, 6, 7, 8, 9, 10, 11, 12, 13, 14, or 15 miRNA(s), determined empirically by measuring a number of reference samples, preferably at least two reference samples, more preferably at least 2 to 40 reference samples, even more preferably at least 10 to 60 reference samples, and most preferably at least 50 to 100 reference samples, e.g. at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 reference samples, from (different) patients. Preferably or alternatively, said reference level is an average level. The average level is particularly determined by measuring a number of reference samples, preferably at least two reference samples, more preferably at least 2 to 40 reference samples, even more preferably at least 10 to 60 reference samples, and most preferably at least 50 to 100 reference samples, e.g. at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 reference samples, from a number of patients and calculating the "middle" value (e.g. median or mean value) of the reference levels determined therein.

Said reference samples are preferably samples from successfully treated multiple sclerosis patients, e.g. successfully treated relapsing-remitting multiple sclerosis (RR-MS), secondary progressive multiple sclerosis (SPMS), progressive relapsing multiple sclerosis (PRMS), or primary progressive multiple sclerosis (PPMS) patients.

The term "successfully treated multiple sclerosis (MS), e.g. RR-MS, SP-MS, PR-MS, or PP-MS, patient(s)", as used herein, refers to (a) patient(s) which has (have) already received a therapeutic treatment of multiples sclerosis, particularly by administration of a drug for multiples sclerosis, and responded to said treatment or benefited from said treatment. This response or benefit is particularly characterized by an increase of the level of the at least one miRNA, e.g. 1, 2, 3, 4, 5, 6, 7, or 8 miRNA(s), in the test sample when compared to the reference level of the (said) at least one miRNA, wherein the nucleotide sequence of the at least one miRNA is selected from the group consisting of SEQ ID NO: 1 to SEQ ID NO: 8, a fragment thereof, and a sequence having at least 80% sequence identity thereto, and/or this response or benefit is particularly characterized by a decrease of the level of the at least one miRNA, e.g. 1, 2, 3, 4, 5, 6, or 7 miRNA(s), in the test sample when compared to the reference level of the (said) at least one miRNA, wherein the nucleotide sequence of the at least one miRNA is selected form the group consisting of SEQ ID NO: 9 to SEQ ID NO: 15, a fragment thereof, and a sequence having at least 80% sequence identity thereto. Whether a patient responds to a therapeutic treatment can be determined with the method of the first aspect of the invention and whether a patient benefits from a therapeutic treatment can be determined with the above preferred embodiment of the method of the second aspect of the invention. The term "successfully treated multiple sclerosis (MS), e.g. RR-MS, SP-MS, PR-MS, or PP-MS, patient(s)" may further refer to (i) (a) patient(s) which has (have) already received a therapeutic treatment of multiples sclerosis, particularly by administration of a drug for multiples sclerosis, and which is (are) now free of symptoms of multiples sclerosis or (ii) (a) patient(s) which medical condition is (mostly) stable and does not worsen, preferably (a) patient(s) which has (have) not experienced a relapse over a time period of at least between 3 and 24 months, more preferably over a time period of at least between 6 and 24 months, and most preferably over a time period of at least between 12 and 24 months, e.g. 3, 4, 5, 6, 7, 8, 9, 10, 11, 12, 13, 14, 15, 16, 17, 18, 19, 20, 21, 22, 23, or 24 months. In the first case, the level of the (said) at least one miRNA in the test sample isolated from the (multiple sclerosis) patient increases (e.g. SEQ ID NO: 1 to SEQ ID NO: 8) or decreases (e.g. SEQ ID NO: 9 to SEQ ID NO: 15) due to therapeutic treatment and preferably approaches or reaches the level of the (said) at least one miRNA present in a healthy subject/control, or the average level of the (said) at least one miRNA present in a number of healthy subjects/controls, particularly at least two healthy subjects/controls. In the second case, the level of the (said) at least one miRNA in the test sample isolated from the patient increases (e.g. SEQ ID NO: 1 to SEQ ID NO: 8) or decreases (e.g. SEQ ID NO: 10 to SEQ ID NO: 15) due to therapeutic treatment and preferably reaches a plateau level characterized by a miRNA level which is mostly stable, particularly stable.

It is also (alternatively or additionally) preferred that the reference level is determined in a reference sample isolated from the patient, particularly prior to the isolation of the test sample. For example, the reference level is the level of the (said) at least one miRNA, e.g. 1, 2, 3, 4, 5, 6, 7, 8, 9, 10, 11, 12, 13, 14, or 15 miRNA(s), determined empirically by measuring a number of reference samples, particularly at least two reference samples, from patients and the reference level is determined in the reference sample isolated from the patient prior to the isolation of the test sample. Further, for example, the reference level is the level of the (said) at least one miRNA, e.g. 1, 2, 3, 4, 5, 6, 7, 8, 9, 10, 11, 12, 13, 14, or 15 miRNA(s), determined empirically by measuring a number of reference samples, particularly at least two reference samples, from patients, said reference samples are samples from successfully treated multiple sclerosis patients, e.g. successfully treated relapsing-remitting multiple sclerosis (RR-MS), secondary progressive multiple sclerosis (SPMS), progressive relapsing multiple sclerosis (PRMS), or primary progressive multiple sclerosis (PPMS) patients, and the reference level is determined in the reference sample isolated from the patient prior to the isolation of the test sample.

It is further preferred that the reference sample is isolated from the patient in a time period of between 9 months and 1 day or between 6 months and 1 day prior to the isolation of the test sample, it is more preferred that the reference sample is isolated from the patient in a time period of between 3 months and 1 day prior to the isolation of the test sample, it is even more preferred that the reference sample is isolated from the patient in a time period of between 1 month and 1 day prior to the isolation of the test sample, and it is most preferred that the reference sample is isolated from the patient in a time period of between 3 weeks and 1 day prior to the isolation of the test sample, e.g. 1, 2, 3, 4, 5, 6 day(s), 1, 2, 3 week(s), 1, 2, 3 4, 5, 6, 7, 8, or 9 month(s) prior to the isolation of the test sample.

It is particularly preferred that said reference sample is isolated prior to the therapeutic treatment of multiple sclerosis and said test sample is isolated after the therapeutic treatment or during a therapeutic treatment of multiple sclerosis.

It is also particularly preferred that said reference sample is isolated after the initiation of the therapeutic treatment of multiple sclerosis and said test sample is isolated after the therapeutic treatment or during a therapeutic treatment of multiple sclerosis.

It is particularly more preferred that the reference sample is isolated in a time period of between 3 months and immediately prior to the therapeutic treatment of multiple sclerosis, particularly by administration of a drug for multiple sclerosis, it is particularly even more preferred that the reference sample is isolated in a time period of between 3 weeks and immediately prior to the therapeutic treatment of multiple sclerosis, particularly by administration of a drug for multiple sclerosis, and it is particularly most preferred that the reference sample is isolated in a time period of between 1 day and immediately prior to the therapeutic treatment of multiple sclerosis, particularly by administration of a drug for multiple sclerosis, or between 1 hour and immediately prior to the therapeutic treatment of multiple sclerosis, particularly by administration of a drug for multiple sclerosis, e.g. immediately, 10, 20, 30, 40, 50 minutes, 1, 2, 3, 4, 5, 6, 7, 8, 9, 10, 11, 12, 13, 14, 15, 16, 17, 18, 19, 20, 21, 22, 23 hour(s), 1, 2, 3, 4, 5, 6 day(s), 1, 2, 3 week(s), 1, 2, or 3 month(s) prior to the therapeutic treatment of multiple sclerosis, particularly by administration of a drug for multiple sclerosis.

It is further (alternatively or additionally) particularly more preferred that the reference sample is isolated in a time period of between 3 months and immediately after the initiation of the therapeutic treatment, particularly by administration of a drug for multiple sclerosis, it is particularly even more preferred that the reference sample is isolated in a time period of between 3 weeks and immediately after the initiation of the therapeutic treatment, particularly by administration of a drug for multiple sclerosis, and it is particularly most preferred that the reference sample is isolated in a time period of between 1 day and immediately after the initiation of the therapeutic treatment, particularly by administration of a drug for multiple sclerosis, or between 1 hour and immediately after the initiation of the therapeutic treatment, particularly by administration of a drug for multiple sclerosis, e.g. immediately, 10, 20, 30, 40, 50 minutes, 1, 2, 3, 4, 5, 6, 7, 8, 9, 10, 11, 12, 13, 14, 15, 16, 17, 18, 19, 20, 21, 22, 23 hour(s), 1, 2, 3, 4, 5, 6 day(s), 1, 2, 3 week(s), 1, 2, or 3 month(s) after the initiation of the therapeutic treatment, particularly by administration of a drug for multiple sclerosis.

It is also (alternatively or additionally) particularly more preferred that the test sample is isolated in a time period of between 6 months and immediately after the therapeutic treatment, particularly by administration of a drug for multiple sclerosis, or between 3 months and immediately after the therapeutic treatment, particularly by administration of a drug for multiple sclerosis, it is particularly even more preferred that the test sample is isolated in a time period of between 3 weeks and immediately after the therapeutic treatment, particularly by administration of a drug for multiple sclerosis, and it is particularly most preferred that the test sample is isolated in a time period of between 1 day and immediately after the therapeutic treatment, particularly by administration of a drug for multiple sclerosis, or between 1 hour and immediately after the therapeutic treatment, particularly by administration of a drug for multiple sclerosis, e.g. immediately, 10, 20, 30, 40, 50 minutes, 1, 2, 3, 4, 5, 6, 7, 8, 9, 10, 11, 12, 13, 14, 15, 16, 17, 18, 19, 20, 21, 22, 23 hour(s), 1, 2, 3, 4, 5, 6 day(s), 1, 2, 3 week(s), 1, 2, 3, 4, 5, or 6 month(s) after the therapeutic treatment, particularly by administration of a drug for multiple sclerosis.

In an alternative preferred embodiment, the reference level is the level of the (said) at least one miRNA, e.g. 1, 2, 3, 4, 5, 6, 7, 8, 9, 10, 11, 12, 13, 14, or 15 miRNA(s), determined in a reference sample isolated from the same patient. Particularly, the reference level is determined in a reference sample isolated from the same patient prior to the isolation of the test sample. Preferably, said patient is a successfully treated multiple sclerosis patient, e.g. a successfully treated relapsing-remitting multiple sclerosis (RR-MS), secondary progressive multiple sclerosis (SPMS), progressive relapsing multiple sclerosis (PRMS), or primary progressive multiple sclerosis (PPMS) patient. As to the definition of the term "successfully treated multiple sclerosis patient", it is referred to the above. For example, the reference level is the level of the (said) at least one miRNA, e.g. 1, 2, 3, 4, 5, 6, 7, 8, 9, 10, 11, 12, 13, 14, or 15 miRNA(s), determined in a reference sample isolated from the same patient, particularly prior to the isolation of the test sample, and said patient is a relapsing-remitting multiple sclerosis (RR-MS) patient, secondary progressive multiple sclerosis (SPMS) patient, progressive relapsing multiple sclerosis (PRMS) patient, or primary progressive multiple sclerosis (PPMS) patient.

It is further preferred that the reference sample is isolated from the same patient in a time period of between 9 months and 1 day or between 6 months and 1 day prior to the isolation of the test sample, it is more preferred that the reference sample is isolated from the same patient in a time period of between 3 months and 1 day prior to the isolation of the test sample, it is even more preferred that the reference sample is isolated from the same patient in a time period of between 1 month and 1 day prior to the isolation of the test sample, and it is most preferred that the reference sample is isolated from the same patient in a time period of between 3 weeks and 1 day prior to the isolation of the test sample, e.g. 1, 2, 3, 4, 5, 6 day(s), 1, 2, 3 week(s), 1, 2, 3 4, 5, 6, 7, 8, or 9 month(s) prior to the isolation of the test sample.

It is particularly preferred that said reference sample is isolated prior to the therapeutic treatment of multiple sclerosis and said test sample is isolated after the therapeutic treatment or during a therapeutic treatment of multiple sclerosis, particularly from the same patient.

It is also particularly preferred that said reference sample is isolated after the initiation of the therapeutic treatment of multiple sclerosis and said test sample is isolated after the therapeutic treatment or during a therapeutic treatment of multiple sclerosis, particularly from the same patient.

It is particularly more preferred that the reference sample is isolated in a time period of between 3 months and immediately prior to the therapeutic treatment of multiple sclerosis, particularly by administration of a drug for multiple sclerosis, it is particularly even more preferred that the reference sample is isolated in a time period of between 3 weeks and immediately prior to the therapeutic treatment of multiple sclerosis, particularly by administration of a drug for multiple sclerosis, and it is particularly most preferred that the reference sample is isolated in a time period of between 1 day and immediately prior to the therapeutic treatment of multiple sclerosis, particularly by administration of a drug for multiple sclerosis, or between 1 hour and immediately prior to the therapeutic treatment of multiple sclerosis, particularly by administration of a drug for multiple sclerosis, e.g. immediately, 10, 20, 30, 40, 50 minutes, 1, 2, 3, 4, 5, 6, 7, 8, 9, 10, 11, 12, 13, 14, 15, 16, 17, 18, 19, 20, 21, 22, 23 hour(s), 1, 2, 3, 4, 5, 6 day(s), 1, 2, 3 week(s), 1, 2, or 3 month(s) prior to the therapeutic treatment of multiple sclerosis, particularly by administration of a drug for multiple sclerosis.

It is further (alternatively or additionally) particularly more preferred that the reference sample is isolated in a time period of between 3 months and immediately after the initiation of the therapeutic treatment, particularly by administration of a drug for multiple sclerosis, it is particularly even more preferred that the reference sample is isolated in a time period of between 3 weeks and immediately after the initiation of the therapeutic treatment, particularly by administration of a drug for multiple sclerosis, and it is particularly most preferred that the reference sample is isolated in a time period of between 1 day and immediately after the initiation of the therapeutic treatment, particularly by administration of a drug for multiple sclerosis, or between 1 hour and immediately after the initiation of the therapeutic treatment, particularly by administration of a drug for multiple sclerosis, e.g. immediately, 10, 20, 30, 40, 50 minutes, 1, 2, 3, 4, 5, 6, 7, 8, 9, 10, 11, 12, 13, 14, 15, 16, 17, 18, 19, 20, 21, 22, 23 hour(s), 1, 2, 3, 4, 5, 6 day(s), 1, 2, 3 week(s), 1, 2, or 3 month(s) after the initiation of the therapeutic treatment, particularly by administration of a drug for multiple sclerosis.

It is also (alternatively or additionally) particularly more preferred that the test sample is isolated in a time period of between 6 months and immediately after the therapeutic treatment, particularly by administration of a drug for multiple sclerosis, or between 3 months and immediately after the therapeutic treatment, particularly by administration of a drug for multiple sclerosis, it is particularly even more preferred that the test sample is isolated in a time period of between 3 weeks and immediately after the therapeutic treatment, particularly by administration of a drug for multiple sclerosis, and it is particularly most preferred that the test sample is isolated in a time period of between 1 day and immediately after the therapeutic treatment, particularly by administration of a drug for multiple sclerosis, or between 1 hour and immediately after the therapeutic treatment, particularly by administration of a drug for multiple sclerosis, e.g. immediately, 10, 20, 30, 40, 50 minutes, 1, 2, 3, 4, 5, 6, 7, 8, 9, 10, 11, 12, 13, 14, 15, 16, 17, 18, 19, 20, 21, 22, 23 hour(s), 1, 2, 3, 4, 5, 6 day(s), 1, 2, 3 week(s), 1, 2, 3, 4, 5, or 6 month(s) after the therapeutic treatment, particularly by administration of a drug for multiple sclerosis.

As to the definition of the terms "test sample" and "reference sample" and as to the preferred embodiments of the "test sample" and "reference sample", it is referred to the first aspect of the invention.

As mentioned above, it is preferred that the level of the at least one miRNA, e.g. 1, 2, 3, 4, 5, 6, 7, 8, 9, 10, 11, 12, 13, 14, or 15 miRNA(s), in the test sample is compared to a reference level of the (said) at least one miRNA. In addition, the preferred embodiments of the reference level and reference sample are described above.

In a preferred embodiment, the nucleotide sequence of the at least one miRNA, e.g. 1, 2, 3, 4, 5, 6, 7, or 8 miRNA(s), is selected from the group consisting of SEQ ID NO: 1 to SEQ ID NO: 8, a fragment thereof, and a sequence having at least 80% sequence identity thereto, preferably SEQ ID NO: 1, SEQ ID NO: 2, SEQ ID NO: 5 to SEQ ID NO: 8, a fragment thereof, and a sequence having at least 80% sequence identity thereto, more preferably SEQ ID NO: 1, SEQ ID NO: 2, a fragment thereof, and a sequence having at least 80% sequence identity thereto, wherein an increase of the level of the at least one miRNA in the test sample when compared to the reference level of the at least one miRNA indicates that multiple sclerosis in the patient further improves. More preferably, the miRNAs have nucleotide sequences according to SEQ ID NO: 1, a fragment thereof, or a sequence having at least 80% sequence identity thereto and according to SEQ ID NO: 2, a fragment thereof, or a sequence having at least 80% sequence identity thereto. In a particularly preferred embodiment, the nucleotide sequence of the at least one miRNA, e.g. 1 or 2 miRNA(s), is selected from the group consisting of SEQ ID NO: 3, SEQ ID NO: 4, a fragment thereof, and a sequence having at least 80% sequence identity thereto, wherein an increase of the level of the at least one miRNA in the test sample when compared to the reference level of the at least one miRNA only indicates that multiple sclerosis in the patient further improves when the level of at least one miRNA, e.g. 1 or 2 miRNA(s), selected from the group consisting of SEQ ID NO: 1, SEQ ID NO: 2, a fragment thereof, and a sequence having at least 80% sequence identity thereto in the test sample when compared to the reference level of the at least one miRNA is not decreased.

In another preferred embodiment, the nucleotide sequence of the at least one miRNA, e.g. 1, 2, 3, 4, 5, 6, or 7 miRNA(s), is selected from the group consisting of SEQ ID NO: 9 to SEQ ID NO: 15, a fragment thereof, and a sequence having at least 80% sequence identity thereto, preferably SEQ ID NO: 10 to SEQ ID NO: 15, a fragment thereof, and a sequence having at least 80% sequence identity thereto, wherein a decrease of the level of the at least one miRNA in the test sample when compared to the reference level of the at least one miRNA indicates that multiple sclerosis in the patient further improves. In a particularly preferred embodiment, the nucleotide sequence of the at least one miRNA is SEQ ID NO: 9, a fragment thereof, and a sequence having at least 80% sequence identity thereto, wherein a decrease of the level of the at least one miRNA in the test sample when compared to the reference level of the at least one miRNA only indicates that multiple sclerosis in the patient improves or further improves when the level of at least one miRNA, e.g. 1 or 2 miRNA(s), selected from the group consisting of SEQ ID NO: 1, SEQ ID NO: 2, a fragment thereof, and a sequence having at least 80% sequence identity thereto in the test sample when compared to the reference level of the at least one miRNA is not decreased.

More preferably,
(i) an at least 1.2 fold increase, preferably an at least 1.4 fold increase, of the level of the miRNA having a nucleotide sequence according to SEQ ID NO: 1, an at least 1.2 fold increase, preferably an at least 1.4 fold increase, of the level of the miRNA having a nucleotide sequence according to SEQ ID NO: 2, an at least 1.2 fold increase, preferably an at least 1.4 fold increase, of the level of the miRNA having a nucleotide sequence according to SEQ ID NO: 3, an at least 1.2 fold increase, preferably an at least 1.4 fold increase, of the level of the miRNA having a nucleotide sequence according to SEQ ID NO: 4, an at least 1.2 fold increase, preferably an at least 1.4 fold increase, of the level of the miRNA having a nucleotide sequence according to SEQ ID NO: 5, an at least 1.2 fold increase, preferably an at least 1.4 fold increase, of the level of the miRNA having a nucleotide sequence according to SEQ ID NO: 6, an at least 1.2 fold increase, preferably an at least 1.4 fold increase, of the level of the miRNA having a nucleotide sequence according to SEQ ID NO: 7, and/or an at least 1.2 fold increase, preferably an at least 1.4 fold increase, of the level of the miRNA having a nucleotide sequence according to SEQ ID NO: 8 indicates that multiple sclerosis in the patient improves or further improves, and/or (ii) an at least 1.2 fold decrease, preferably an at least 1.4 fold decrease, of the level of the miRNA having a nucleotide sequence according to SEQ ID NO: 9, an at least 1.2 fold decrease, preferably an at least 1.4 fold decrease, of the level of the miRNA having a nucleotide sequence according to SEQ ID NO: 10, an at least 1.2 fold decrease, preferably an at least 1.4 fold decrease, of the level of the miRNA having a nucleotide sequence according to SEQ ID NO: 11, an at least 1.2 fold decrease, preferably an at least 1.4 fold decrease, of the level of the miRNA having a nucleotide sequence according to SEQ ID NO: 12, an at least 1.2 fold decrease, preferably an at least 1.4 fold decrease, of the level of the miRNA having a nucleotide sequence according to SEQ ID NO: 13, an at least 1.2 fold decrease, preferably an at least 1.4 fold decrease, of the level of the miRNA having a nucleotide sequence according to SEQ ID NO: 14, and/or an at least 1.2 fold decrease, preferably an at least 1.4 fold decrease, of the level of the miRNA having a nucleotide sequence according to SEQ ID NO: 15 indicates that multiple sclerosis in the patient improves or further improves.

In a further preferred embodiment, the nucleotide sequence of the at least one miRNA, e.g. 1, 2, 3, 4, 5, 6, 7, or 8 miRNA(s), is selected from the group consisting of SEQ ID NO: 1 to SEQ ID NO: 8, a fragment thereof, and a sequence having at least 80% sequence identity thereto, preferably SEQ ID NO: 1, SEQ ID NO: 2, SEQ ID NO: 5 to SEQ ID NO: 8, a fragment thereof, and a sequence having at least 80% sequence identity thereto, more preferably SEQ ID NO: 1, SEQ ID NO: 2, a fragment thereof, and a sequence having at least 80% sequence identity thereto, wherein a non-alteration of the level of the at least one miRNA in the test sample when compared to the reference level of the at least one miRNA indicates that multiple sclerosis in the patient is stable. More preferably, the miRNAs have nucleotide sequences according to SEQ ID NO: 1, a fragment thereof, or a sequence having at least 80% sequence identity thereto and according to SEQ ID NO: 2, a fragment thereof, or a sequence having at least 80% sequence identity thereto. In a particularly preferred embodiment, the nucleotide sequence of the at least one miRNA, e.g. 1 or 2 miRNA(s), is selected from the group consisting of SEQ ID NO: 3, SEQ ID NO: 4, a fragment thereof, and a sequence having at least 80% sequence identity thereto, wherein a non-alteration of the level of the at least one miRNA in the test sample when compared to the reference level of the at least one miRNA only indicates that multiple sclerosis in the patient is stable when the level of at least one miRNA, e.g. 1 or 2 miRNA(s), selected from the group consisting of SEQ ID NO: 1, SEQ ID NO: 2, a fragment thereof, and a sequence having at least 80% sequence identity thereto in the test sample when compared to the reference level of the at least one miRNA is not altered.

In another further preferred embodiment, the nucleotide sequence of the at least one miRNA, e.g. 1, 2, 3, 4, 5, 6, or 7 miRNA(s), is selected from the group consisting of SEQ ID NO: 9 to SEQ ID NO: 15, a fragment thereof, and a sequence having at least 80% sequence identity thereto, preferably SEQ ID NO: 10 to SEQ ID NO: 15, a fragment thereof, and a sequence having at least 80% sequence identity thereto, wherein a non-alteration of the level of the at least one miRNA in the test sample when compared to the reference level of the at least one miRNA indicates that multiple sclerosis in the patient is stable. In a particularly preferred embodiment, the nucleotide sequence of the at least one miRNA is SEQ ID NO: 9, a fragment thereof, and a sequence having at least 80% sequence identity thereto, wherein a non-alteration of the level of the at least one miRNA in the test sample when compared to the reference level of the at least one miRNA only indicates that multiple sclerosis in the patient is stable when the level of at least one miRNA, e.g. 1 or 2 miRNA(s), selected from the group consisting of SEQ ID NO: 1, SEQ ID NO: 2, a fragment thereof, and a sequence having at least 80% sequence identity thereto in the test sample when compared to the reference level of the at least one miRNA is not altered.

The term "that the level of the at least one miRNA in the test sample when compared to the reference level of the at least one miRNA is not altered" may mean that the level of the at least one miRNA in the test sample when compared to the reference level varies between >0 to 20%, preferably between >0 to 10%, more preferably between >0 to 5% or between >0 to 3%, e.g. 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, or 20%. Most preferably, the level of the at least ne miRNA in the test sample when compared to the reference level does not vary or is constant.

In an additional preferred embodiment, the nucleotide sequence of the at least one miRNA, e.g. 1, 2, 3, 4, 5, 6, 7, or 8 miRNA(s), is selected from the group consisting of SEQ ID NO: 1 to SEQ ID NO: 8, a fragment thereof, and a sequence having at least 80% sequence identity thereto, preferably SEQ ID NO: 1, SEQ ID NO: 2, SEQ ID NO: 5 to SEQ ID NO: 8, a fragment thereof, and a sequence having at least 80% sequence identity thereto, more preferably SEQ ID NO: 1, SEQ ID NO: 2, a fragment thereof, and a sequence having at least 80% sequence identity thereto, wherein a decrease of the level of the at least one miRNA in the test sample when compared to the reference level of the at least one miRNA indicates that multiple sclerosis in the patient again exacerbates. More preferably, the miRNAs have nucleotide sequences according to SEQ ID NO: 1, a fragment thereof, or a sequence having at least 80% sequence identity thereto and according to SEQ ID NO: 2, a fragment thereof, or a sequence having at least 80% sequence identity thereto. In a particularly preferred embodiment, the nucleotide sequence of the at least one miRNA, e.g. 1 or 2 miRNA(s), is selected from the group consisting of SEQ ID NO: 3, SEQ ID NO: 4, a fragment thereof, and a sequence having at least 80% sequence identity thereto, wherein a decrease of the level of the at least one miRNA in the test sample when compared to the reference level of the at least one miRNA only indicates that multiple sclerosis in the patient again exacerbates when the level of at least one miRNA, e.g. 1 or 2 miRNA(s), selected from the group consisting of SEQ ID NO: 1, SEQ ID NO: 2, a fragment thereof, and a sequence having at least 80% sequence identity thereto in the test sample when compared to the reference level of the at least one miRNA is not increased.

In another additional preferred embodiment, the nucleotide sequence of the at least one miRNA, e.g. 1, 2, 3, 4, 5, 6, or 7 miRNA(s), is selected from the group consisting of SEQ ID NO: 9 to SEQ ID NO: 15, a fragment thereof, and a sequence having at least 80% sequence identity thereto, preferably SEQ ID NO: 10 to SEQ ID NO: 15, a fragment thereof, and a sequence having at least 80% sequence identity thereto, wherein an increase of the level of the at least one miRNA in the test sample when compared to the reference level of the at least one miRNA indicates that multiple sclerosis in the patient again exacerbates. In a particularly preferred embodiment, the nucleotide sequence of the at least one miRNA is SEQ ID NO: 9, a fragment thereof, and a sequence having at least 80% sequence identity thereto, wherein an increase of the level of the at least one miRNA in the test sample when compared to the reference level of the at least one miRNA only indicates that multiple sclerosis in the patient again exacerbates when the level of at least one miRNA, e.g. 1 or 2 miRNA(s), selected from the group consisting of SEQ ID NO: 1, SEQ ID NO: 2, a fragment thereof, and a sequence having at least 80% sequence identity thereto in the test sample when compared to the reference level of the at least one miRNA is not increased.

The above method is a method which aims at determining whether multiple sclerosis in the patient further improves, again exacerbates or is stable. Said patient may be a patient which receives or has received a successful therapeutic treatment of multiple sclerosis. Said therapeutic treatment may involve the application/administration of a drug for multiple sclerosis. Said drug may be selected from the group consisting of natalizumab, interferon beta 1a, interferon beta 1b, glatiramer acetate, alemtuzumab, fingolimod, dimethylfumarate, and mitoxantrone. In a preferred embodiment, the above method further comprises the step of administering (i) a renewed dose of the drug when multiple sclerosis in said patient is stable, (ii) a dose which is increased compared to the previously administered dose of the drug when multiple sclerosis in said patient again exacerbates, or (iii) a renewed dose of the drug or a dose which is decreased compared to the previously administered dose of the drug when multiple sclerosis in said patient further improves. Alternatively, when multiple sclerosis in said patient again exacerbates, the drug may be changed, i.e. another drug (e.g. selected from the group consisting of natalizumab, interferon beta 1a, interferon beta 1b, glatiramer acetate, alemtuzumab, fingolimod, dimethylfumarate, and mitoxantrone) may be administered. In another preferred embodiment, the above method further comprises the step of continuing the treatment of multiple sclerosis when multiple sclerosis in said patient is stable or further improves, or discontinuing the treatment of multiple sclerosis when multiple sclerosis in said patient again exacerbates. In the latter case, the administered drug may be changed, i.e. another drug (e.g. selected from the group consisting of natalizumab, interferon beta 1a, interferon beta 1b, glatiramer acetate, alemtuzumab, fingolimod, dimethylfumarate, and mitoxantrone) may be administered.

The above mentioned nucleotide sequence of the miRNA, particularly the nucleotide sequence of the miRNA referred to in the preferred embodiment of the second aspect of the invention, in the another preferred embodiment of the second aspect of the invention, and in the additional preferred embodiment of the second aspect of the invention, is selected from the group consisting of
(i) a nucleotide sequence according to SEQ ID NO: 1 to SEQ ID NO: 15,
(ii) a nucleotide sequence that is a fragment of the nucleotide sequence according to (i), preferably, a nucleotide sequence that is a fragment which is between 1 and 12, more preferably between 1 and 8, and most preferably between 1 and 5 or 1 and 3, i.e. 1, 2, 3, 4, 5, 6, 7, 8, 9, 10, 11, or 12, nucleotides shorter than the nucleotide sequence according to (i), and
(iii) a nucleotide sequence that has at least 80%, preferably at least 85%, more preferably at least 90%, and most preferably at least 95% or 99%, i.e. 80, 81, 82, 83, 84, 85, 86, 87, 88, 89, 90, 91, 92, 93, 94, 95, 96, 97, 98, or 99%, sequence identity to the nucleotide sequence according to (i) or nucleotide sequence fragment according to (ii).

It is particularly preferred that the nucleotide sequence as defined in (iii) has at least 80%, preferably at least 85%, more preferably at least 90%, and most preferably at least 95% or 99%, i.e. 80, 81, 82, 83, 84, 85, 86, 87, 88, 89, 90, 91, 92, 93, 94, 95, 96, 97, 98, or 99%, sequence identity over a continuous stretch of at least 10, 11, 12, 13, 14, 15, 16, 17, 18, 19, 20 or more nucleotides, preferably over the whole length, to the nucleotide sequence of the nucleotide according to (i) or nucleotide fragment according to (ii).

In addition, the nucleotide sequence as defined in (ii) (i.e. nucleotide sequence fragment) or (iii) (i.e. nucleotide sequence variant or nucleotide sequence fragment variant) is only regarded as a nucleotide sequence as defined in (ii) (i.e. nucleotide sequence fragment) or (iii) (i.e. nucleotide sequence variant or nucleotide sequence fragment variant) within the context of the present invention, if it can still be bound, hybridized, recognized, or detected by a polynucleotide (probe) of complementary sequence, e.g. a polynucleotide (probe) which is complementary to the respective nucleotide sequence as defined in (i), through one or more types of chemical bonds, usually through complementary base pairing, usually through hydrogen bond formation under stringent hybridization conditions. The skilled person can readily assess whether a nucleotide sequence as defined in (ii) (i.e. nucleotide sequence fragment) or (iii) (i.e. nucleotide sequence variant or nucleotide sequence fragment variant) can still be bound, hybridized, recognized, or detected by a polynucleotide (probe) of complementary sequence, e.g. a polynucleotide (probe) which is complementary to the respective nucleotide sequence as defined in (i). Suitable assays to determine whether hybridization under stringent conditions still occurs are well known in the art. However, as an example, a suitable assay to determine whether hybridization still occurs comprises the steps of: (a) incubating a nucleotide sequence as defined in (ii) or (iii) labelled with biotin with a polynucleotide (probe) of complementary sequence, e.g. a polynucleotide (probe) which is complementary to the respective nucleotide sequence as defined in (i), wherein the polynucleotide (probe) is attached onto a biochip, under stringent hybridization conditions, (b) washing the biochip to remove unspecific bindings, (c) subjecting the biochip to a detection system, and (c) analyzing whether the nucleotide sequence can still be hybridized or detected by a polynucleotide (probe) of complementary sequence, e.g. a polynucleotide (probe) which is complementary to the respective nucleotide sequence as defined in (i). As a positive control, the respective miRNA as defined in (i) may be used. Preferably stringent hybridization conditions include the following: 50% formamide, 5×SSC, and 1% SDS, incubating at 42° C., or, 5×SSC, 1% SDS, incubating at 65° C., with wash in 0.2×SSC, and 0.1% SDS at 65° C.; or 6×SSPE, 10% formamide, 0.01%, Tween 20, 0.1×TE buffer, 0.5 mg/ml BSA, 0.1 mg/ml herring sperm DNA, incubating at 42° C. with wash in 0.5×SSPE and 6×SSPE at 45° C.

The patient may be any organism such as vertebrate, particularly any mammal, including both a human and another mammal, e.g. an animal such as a rodent, a rabbit, or a monkey. The rodent may be a mouse, rat, hamster, guinea pig, or chinchilla. Preferably, the patient is a human or a rodent.

Preferably, multiples sclerosis (MS) is relapsing-remitting multiple sclerosis (RR-MS), secondary progressive multiple sclerosis (SPMS), progressive relapsing multiple sclerosis (PRMS), or primary progressive multiple sclerosis (PPMS). More preferably, multiples sclerosis (MS) is relapsing-remitting multiple sclerosis (RR-MS).

As mentioned above, the method of monitoring the course of multiple sclerosis comprises the step of:
determining the level of at least one miRNA, e.g. 1, 2, 3, 4, 5, 6, 7, 8, 9, 10, 11, 12, 13, 14, or 15 miRNA(s), in a test sample isolated from the patient, wherein the nucleotide sequence of the at least one miRNA is selected from the group consisting of SEQ ID NO: 1 to SEQ ID NO: 15, a fragment thereof, and a sequence having at least 80% sequence identity thereto.

It is preferred that the level of the miRNA is the expression level. Said level of the miRNA, particularly expression level of the miRNA, may be indicated as (relative) miRNA concentration, (relative) miRNA amount, or (relative) miRNA extinction units such as relative fluorescence units.

Preferably the level of the miRNA, particularly the expression level of the miRNA, is determined by nucleic acid hybridization, nucleic acid amplification, polymerase extension, sequencing, mass spectroscopy or any combination thereof. More preferably, (i) the nucleic acid hybridization is performed using a microarray/biochip or beads, or using in situ hybridization, and/or (ii) the nucleic acid amplification is performed using real-time PCR. As to the above means to determine the level of the miRNA, particularly expression level of the miRNA, it is also referred to the first aspect of the invention.

In a preferred embodiment, the (expression) level of the at least one miRNA is determined by determining the level of the cDNA generated/transcribed from said miRNA. Preferably, said level is determined using a real time quantitative polymerase chain reaction (RT qPCR).

In another preferred embodiment, the level of the at least one miRNA is determined after a size selection of RNA which is smaller than 1000 base pairs, preferably smaller than 500 base pairs, more preferably smaller than 100 base pairs, and most preferably smaller than 30 base pairs.

In a further preferred embodiment the level of the at least one miRNA is determined from a test sample that includes means for stabilizing the RNA-fraction, especially the small RNA fraction. Preferably, the means for stabilizing the RNA fraction, especially the small RNA-fraction have been either added to the test sample during or after blood collection (e.g. by adding RNAlater, or RNAretain) or were already included in the blood collection tube (e.g PAXgene tube, PAXgene blood RNA tube, or Tempus blood RNA tube)

It is preferred that the polynucleotide (probe) according to the sixth aspect of the invention or the polynucleotide set comprising at least two different polynucleotide (probes) according to the seventh aspect of the invention is used in the method of the second aspect of the invention to determine the level, particularly expression level, of at least one miRNA in a test sample isolated from the patient, wherein the nucleotide sequence of the at least one miRNA is selected from the group consisting of SEQ ID NO: 1 to SEQ ID NO: 15, a fragment thereof, and a sequence having at least 80% sequence identity thereto. It is particularly preferred that said polynucleotide is part of a biochip, or comprised on beads or microspheres or said at least two different polynucleotides are comprised on a biochip, or on a set of beads or microspheres.

In a third aspect, the present invention relates to a method of determining the risk for a relapse of multiple sclerosis (MS) in a patient comprising the step of:
determining the level of at least one miRNA in a test sample isolated from the patient, wherein the nucleotide sequence of the at least one miRNA is selected from the group consisting of SEQ ID NO: 1 to SEQ ID NO: 15, a fragment thereof, and a sequence having at least 80% sequence identity thereto.

It is preferred that the level of the nucleotide sequence of the miRNA having SEQ ID NO: 1, SEQ ID NO: 2, SEQ ID NO: 3, SEQ ID NO: 4, SEQ ID NO: 9, a fragment thereof, or a sequence having at least 80% sequence identity thereto is determined. It is particularly preferred that the level of the nucleotide sequence of the miRNA having SEQ ID NO: 1, SEQ ID NO: 2, a fragment thereof, or a sequence having at least 80% sequence identity thereto is determined.

In an alternative embodiment, the level of the nucleotide sequence of the miRNA having SEQ ID NO: 3, a fragment thereof, or a sequence having at least 80% sequence identity thereto, and/or the level of the nucleotide sequence of the miRNA having SEQ ID NO: 9, a fragment thereof, or a sequence having at least 80% sequence identity thereto is not determined.

It is further preferred that the level of the nucleotide sequences of the miRNAs having SEQ ID NO: 1 to SEQ ID NO: 15, fragments thereof, or sequences having at least 80% sequence identity thereto is determined. It is particularly preferred that the level of the nucleotide sequences of the miRNAs having SEQ ID NO: 1 to SEQ ID NO: 8, fragments thereof, or sequences having at least 80% sequence identity thereto is determined or that the level of nucleotide sequences of the miRNAs having SEQ ID NO: 9 to SEQ ID NO: 15, fragments thereof, or sequences having at least 80% sequence identity thereto is determined. It is more preferred that the level of the nucleotide sequences of the miRNAs having SEQ ID NO: 1 to SEQ ID NO: 4 and SEQ ID NO: 9, fragments thereof, or sequences having at least 80% sequence identity thereto is determined. It is particularly more preferred that the level of the nucleotide sequences of the miRNAs having SEQ ID NO: 1 to SEQ ID NO: 4, fragments thereof, or sequences having at least 80% sequence identity thereto is determined. It is most preferred that the level of the nucleotide sequences of the miRNAs having (i) SEQ ID NO: 1 and SEQ ID NO: 2, fragments thereof, or sequence having at least 80% sequence identity thereto, (ii) SEQ ID NO: 1 and SEQ ID NO: 3, fragments thereof, or sequences having at least 80% sequence identity thereto, (iii) SEQ ID NO: 1 and SEQ ID NO: 4, fragments thereof, or sequences having at least 80% sequence identity thereto, (iv) SEQ ID NO: 2 and SEQ ID NO: 3, fragments thereof, or sequences having at least 80% sequence identity thereto, (v) SEQ ID NO: 2 and SEQ ID NO: 4, fragments thereof, or sequences having at least 80% sequence identity thereto, or (vi) SEQ ID NO: 3 and SEQ ID NO: 4, fragments thereof, or sequences having at least 80% sequence identity thereto is determined.

In case of the miRNA having a nucleotide sequence according to SEQ ID NO: 3, a fragment thereof, or a sequence having at least 80% sequence identity thereto, it is preferred that the level of this miRNA is only determined together with the level of at least one further miRNA having a nucleotide sequence selected from the group consisting of SEQ ID NO: 1, SEQ ID NO: 2, SEQ ID NO: 4 to SEQ ID NO: 15, a fragment thereof, and a sequence having at least 80% sequence identity thereto, particularly selected from the group consisting of SEQ ID NO: 1, SEQ ID NO: 2, SEQ ID NO: 4 to SEQ ID NO: 8, SEQ ID NO: 10 to SEQ ID NO: 15, a fragment thereof, and a sequence having at least 80% sequence identity thereto, or in case of the miRNA having a nucleotide sequence according to SEQ ID NO: 9, a fragment thereof, or a sequence having at least 80% sequence identity thereto, it is preferred that the level of this miRNA is only determined together with the level of at least one further miRNA having a nucleotide sequence selected from the group consisting of SEQ ID NO: 1 to SEQ ID NO: 8, SEQ ID NO: 10 to SEQ ID NO: 15, a fragment thereof, and a sequence having at least 80% sequence identity thereto, particularly selected from the group consisting of SEQ ID NO: 1, SEQ ID NO: 2, SEQ ID NO: 4 to SEQ ID NO: 8, SEQ ID NO: 10 to SEQ ID NO: 15, a fragment thereof, and a sequence having at least 80% sequence identity thereto. In addition, in case of miRNAs having nucleotide sequences according to SEQ ID NO: 3, SEQ ID NO: 9, a fragment thereof, or a sequence having at least 80% sequence identity thereto, it is preferred that the level of these miRNA is only determined together with the level of at least one further miRNA having a nucleotide sequence selected from the group consisting of SEQ ID NO: 1, SEQ ID NO: 2, SEQ ID NO: 4 to SEQ ID NO: 8, SEQ ID NO: 10 to SEQ ID NO: 15, a fragment thereof, and a sequence having at least 80% sequence identity thereto. Other preferred miRNA combinations are listed in FIG. 8.

It is preferred that the patient receives or has received a therapeutic treatment of multiple sclerosis.

It is also, alternatively or additionally, preferred that the test sample is isolated during or after therapeutic treatment of multiple sclerosis. It is particularly preferred that the test sample is isolated in a time period of between 6 months and immediately after therapeutic treatment of multiple sclerosis, it is particularly more preferred that the test sample is isolated in a time period of between 3 months and immediately after therapeutic treatment of multiple sclerosis, it is particularly even more preferred that the test sample is isolated in a time period of between 3 weeks and immediately after therapeutic treatment of multiple sclerosis, and it is particularly most preferred that the test sample is isolated in a time period of between 1 day and immediately after therapeutic treatment of multiple sclerosis or between 1 hour and immediately after therapeutic treatment of multiple sclerosis, e.g. immediately, 10, 20, 30, 40, 50 minutes, 1, 2, 3, 4, 5, 6, 7, 8, 9, 10, 11, 12, 13, 14, 15, 16, 17, 18, 19, 20, 21, 22, 23 hour(s), 1, 2, 3, 4, 5, 6 day(s), 1, 2, 3 week(s), 1, 2, 3, 4, 5, or 6 month(s) after therapeutic treatment of multiple sclerosis. It is more preferred that said treatment involves the administration of a drug for multiple sclerosis. Said drug may be selected from the group consisting of natalizumab, interferon beta 1a, interferon beta 1b, glatiramer acetate, alemtuzumab, fingolimod, dimethylfumarate, and mitoxantrone. Preferably, the drug is natalizumab.

Preferably, the level of the at least one miRNA, e.g. 1, 2, 3, 4, 5, 6, 7, 8, 9, 10, 11, 12, 13, 14, or 15 miRNA(s), in the test sample is compared to a reference level of the (said) at least one miRNA. Thus, in a preferred embodiment, the method of determining the risk for a relapse of multiples sclerosis in a patient comprises the steps of:
(i) determining the level of at least one miRNA, e.g. 1, 2, 3, 4, 5, 6, 7, 8, 9, 10, 11, 12, 13, 14, or 15 miRNA(s), in a test sample isolated from the patient, wherein the nucleotide sequence of the at least one miRNA is selected from the group consisting of SEQ ID NO: 1 to SEQ ID NO: 15, a fragment thereof, and a sequence having at least 80% sequence identity thereto, and
(ii) comparing the level of the at least one miRNA in the test sample to a reference level of the (said) at least one miRNA, e.g. 1, 2, 3, 4, 5, 6, 7, 8, 9, 10, 11, 12, 13, 14, or 15 miRNA(s).

It is preferred that the patient receives or has received a therapeutic treatment of multiple sclerosis. It is also, alternatively or additionally, preferred that the test sample is isolated during or after therapeutic treatment of multiple sclerosis. It is more preferred that said treatment involves the administration of a drug for multiple sclerosis. Said drug may be selected from the group consisting of natalizumab, interferon beta 1a, interferon beta 1b, glatiramer acetate, alemtuzumab, fingolimod, dimethylfumarate, and mitoxantrone. Preferably, the drug is natalizumab.

In a preferred embodiment, the reference level is the level of the (said) at least one miRNA, e.g. 1, 2, 3, 4, 5, 6, 7, 8, 9, 10, 11, 12, 13, 14, or 15 miRNA(s), determined empirically by measuring a number of reference samples, preferably at least two reference samples, more preferably at least 2 to 40 reference samples, even more preferably at least 10 to 60 reference samples, and most preferably at least 50 to 100 reference samples, e.g. at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 reference samples, from (different) patients. Preferably or alternatively, said reference level is an average level. The average level is particularly determined by measuring a number of reference samples, preferably at least two reference samples, more preferably at least 2 to 40 reference samples, even more preferably at least 10 to 60 reference samples, and most preferably at least 50 to 100 reference samples, e.g. at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 reference samples, from a number of patients and calculating the "middle" value (e.g. median or mean value) of the reference levels determined therein. The reference samples may be isolated during therapeutic treatment of multiple sclerosis. Said reference samples are preferably samples from successfully treated multiple sclerosis patients, e.g. successfully treated relapsing-remitting multiple sclerosis (RR-MS), secondary progressive multiple sclerosis (SPMS), progressive relapsing multiple sclerosis (PRMS), or primary progressive multiple sclerosis (PPMS) patients. As to the definition of the term "successfully treated multiple sclerosis patients", it is referred to the second aspect of the invention.

It is (alternatively or additionally) preferred that the reference level is determined in a reference sample isolated from the patient, particularly prior to the isolation of the test sample. It is also (alternatively or additionally) preferred that the reference sample is isolated during the therapeutic treatment of multiple sclerosis. For example, the reference level is the level of the (said) at least one miRNA, e.g. 1, 2, 3, 4, 5, 6, 7, 8, 9, 10, 11, 12, 13, 14, or 15 miRNA(s), determined empirically by measuring a number of reference samples, particularly at least two reference samples, from patients, and the reference level is determined in the reference sample isolated from the patient prior to the isolation of the test sample. Said reference samples may further be samples from successfully treated multiple sclerosis patients, e.g. successfully treated relapsing-remitting multiple sclerosis (RR-MS), secondary progressive multiple sclerosis (SPMS), progressive relapsing multiple sclerosis (PRMS), or primary progressive multiple sclerosis (PPMS) patients. Further, for example, the reference level is the level of the (said) at least one miRNA, e.g. 1, 2, 3, 4, 5, 6, 7, 8, 9, 10, 11, 12, 13, 14, or 15 miRNA(s), determined empirically by measuring a number of reference samples, particularly at least two reference samples, from patients, and the reference sample is isolated during the therapeutic treatment of multiple sclerosis. Said reference samples may further be samples from successfully treated multiple sclerosis patients, e.g. successfully treated relapsing-remitting multiple sclerosis (RR-MS), secondary progressive multiple sclerosis (SPMS), progressive relapsing multiple sclerosis (PRMS), or primary progressive multiple sclerosis (PPMS) patients. Furthermore, for example, the reference level is the level of the (said) at least one miRNA, e.g. 1, 2, 3, 4, 5, 6, 7, 8, 9, 10, 11, 12, 13, 14, or 15 miRNA(s), determined empirically by measuring a number of reference samples, particularly at least two reference samples, from patients, the reference level is determined in the reference sample isolated from the patient prior to the isolation of the test sample, and the reference sample is isolated during the therapeutic treatment of multiple sclerosis. Said reference samples may further be samples from successfully treated multiple sclerosis patients, e.g. successfully treated relapsing-remitting multiple sclerosis (RR-MS), secondary progressive multiple sclerosis (SPMS), progressive relapsing multiple sclerosis (PRMS), or primary progressive multiple sclerosis (PPMS) patients. It is particularly preferred that the reference sample is isolated from the patient in a time period of between 9 months and 1 day or between 6 months and 1 day prior to the isolation of the test sample, it is particularly more preferred that the reference sample is isolated from the patient in a time period of between 3 months and 1 day prior to the isolation of the test sample, it is particularly even more preferred that the reference sample is isolated from the patient in a time period of between 1 month and 1 day prior to the isolation of the test sample, and it is particularly most preferred that the reference sample is isolated from the patient in a time period of between 3 weeks and 1 day prior to the isolation of the test sample, e.g. 1, 2, 3, 4, 5, 6 day(s), 1, 2, 3 week(s), 1, 2, 3 4, 5, 6, 7, 8, or 9 month(s) prior to the isolation of the test sample.

Preferably,
(i) the nucleotide sequence of the at least one miRNA, e.g. 1, 2, 3, 4, 5, 6, 7, or 8 miRNA(s), is selected from the group consisting of SEQ ID NO: 1 to SEQ ID NO: 8, a fragment thereof, and a sequence having at least 80% sequence identity thereto, wherein said reference level represents the maximal level of the (said) at least one miRNA achievable/achieved in the patient by the therapeutic treatment of multiple sclerosis, and/or
(ii) the nucleotide sequence of the at least one miRNA, e.g. 1, 2, 3, 4, 5, 6, or 7 miRNA(s), is selected from the group consisting of SEQ ID NO: 9 to SEQ ID NO: 15, a fragment thereof, and a sequence having at least 80% sequence identity thereto, wherein said reference level represents the minimal level of the (said) at least one miRNA achievable/achieved in the patient by the therapeutic treatment of multiple sclerosis.

Thus, it is preferred that the method of determining the risk for a relapse of multiples sclerosis in a patient comprises the steps of:
(i) determining the level of at least one miRNA, e.g. 1, 2, 3, 4, 5, 6, 7, or 8 miRNA(s), in a test sample isolated from the patient, wherein the nucleotide sequence of the at least one miRNA is selected from the group consisting of SEQ ID NO: 1 to SEQ ID NO: 8, a fragment thereof, and a sequence having at least 80% sequence identity thereto, and
(ii) comparing the level of the at least one miRNA in the test sample to a reference level of the (said) at least one miRNA, e.g. 1, 2, 3, 4, 5, 6, 7, or 8 miRNA(s), which represents the maximal level of the at least one miRNA achievable in the patient by the therapeutic treatment of multiple sclerosis by the therapeutic treatment of multiple sclerosis.

It is also preferred that the method of determining the risk for a relapse of multiples sclerosis in a patient comprises the steps of:
(i) determining the level of at least one miRNA, e.g. 1, 2, 3, 4, 5, 6, or 7 miRNA(s), in a test sample isolated from the patient, wherein the nucleotide sequence of the at least one miRNA is selected from the group consisting of SEQ ID NO: 9 to SEQ ID NO: 15, a fragment thereof, and a sequence having at least 80% sequence identity thereto, and
(ii) comparing the level of the at least one miRNA in the test sample to a reference level of the (said) at least one miRNA, e.g. 1, 2, 3, 4, 5, 6, or 7 miRNA(s), which represents the minimal level of the at least one miRNA achievable in the patient by the therapeutic treatment of multiple sclerosis.

In an alternative preferred embodiment, the reference level is the level of the (said) at least one miRNA, e.g. 1, 2, 3, 4, 5, 6, 7, 8, 9, 10, 11, 12, 13, 14, or 15 miRNA(s), determined in a reference sample isolated from the same patient. Particularly, the reference level is determined in a reference sample isolated from the same patient prior to the isolation of the test sample. It is further preferred that the reference sample is isolated during therapeutic treatment of multiple sclerosis.

It is also (alternatively or additionally) preferred that said patient is a successfully treated multiple sclerosis patient, e.g. a successfully treated relapsing-remitting multiple sclerosis (RR-MS), secondary progressive multiple sclerosis (SPMS), progressive relapsing multiple sclerosis (PRMS), or primary progressive multiple sclerosis (PPMS) patient. As to the definition of the term "successfully treated multiple sclerosis patients", it is referred to the second aspect of the invention. For example, the reference level is the level of the (said) at least one miRNA, e.g. 1, 2, 3, 4, 5, 6, 7, 8, 9, 10, 11, 12, 13, 14, or 15 miRNA(s), determined in a reference sample isolated from the same patient, particularly prior to the isolation of the test sample, and the reference sample is isolated during therapeutic treatment of multiple sclerosis. Further, for example, the reference level is the level of the (said) at least one miRNA, e.g. 1, 2, 3, 4, 5, 6, 7, 8, 9, 10, 11, 12, 13, 14, or 15 miRNA(s), determined in a reference sample isolated from the same patient, particularly prior to the isolation of the test sample, and said patient is a relapsing-remitting multiple sclerosis (RR-MS) patient, secondary progressive multiple sclerosis (SPMS) patient, progressive relapsing multiple sclerosis (PRMS) patient, or primary progressive multiple sclerosis (PPMS) patient. Furthermore, for example, the reference sample is isolated during therapeutic treatment of multiple sclerosis, and said patient is a relapsing-remitting multiple sclerosis (RR-MS) patient, secondary progressive multiple sclerosis (SPMS) patient, progressive relapsing multiple sclerosis (PRMS) patient, or primary progressive multiple sclerosis (PPMS) patient. In addition, for example, the reference level is the level of the (said) at least one miRNA, e.g. 1, 2, 3, 4, 5, 6, 7, 8, 9, 10, 11, 12, 13, 14, or 15 miRNA(s), determined in a reference sample isolated from the same patient, particularly prior to the isolation of the test sample, the reference sample is isolated during therapeutic treatment of multiple sclerosis, and said patient is a relapsing-remitting multiple sclerosis (RR-MS) patient, secondary progressive multiple sclerosis (SPMS) patient, progressive relapsing multiple sclerosis (PRMS) patient, or primary progressive multiple sclerosis (PPMS) patient. It is particularly preferred that the reference sample is isolated from the same patient in a time period of between 9 months and 1 day or between 6 months and 1 day prior to the isolation of the test sample, it is particularly more preferred that the reference sample is isolated from the same patient in a time period of between 3 months and 1 day prior to the isolation of the test sample, it is particularly even more preferred that the reference sample is isolated from the same patient in a time period of between 1 month and 1 day prior to the isolation of the test sample, and it is particularly most preferred that the reference sample is isolated from the same patient in a time period of between 3 weeks and 1 day prior to the isolation of the test sample, e.g. 1, 2, 3, 4, 5, 6 day(s), 1, 2, 3 week(s), 1, 2, 3 4, 5, 6, 7, 8, or 9 month(s) prior to the isolation of the test sample.

Preferably,
(i) the nucleotide sequence of the at least one miRNA, e.g. 1, 2, 3, 4, 5, 6, 7, or 8 miRNA(s), is selected from the group consisting of SEQ ID NO: 1 to SEQ ID NO: 8, a fragment thereof, and a sequence having at least 80% sequence identity thereto, wherein said reference level represents the maximal level of the (said) at least one miRNA achievable/achieved in the patient by the therapeutic treatment of multiple sclerosis, and/or
(ii) the nucleotide sequence of the at least one miRNA, e.g. 1, 2, 3, 4, 5, 6, or 7 miRNA(s), is selected from the group consisting of SEQ ID NO: 9 to SEQ ID NO: 15, a fragment thereof, and a sequence having at least 80% sequence identity thereto, wherein said reference level represents the minimal level of the (said) at least one miRNA achievable/achieved in the patient by the therapeutic treatment of multiple sclerosis.

Thus, it is preferred that the method of determining the risk for a relapse of multiples sclerosis in a patient comprises the steps of:
(i) determining the level of at least one miRNA, e.g. 1, 2, 3, 4, 5, 6, 7, or 8 miRNA(s), in a test sample isolated from the patient, wherein the nucleotide sequence of the at least one miRNA is selected from the group consisting of SEQ ID NO: 1 to SEQ ID NO: 8, a fragment thereof, and a sequence having at least 80% sequence identity thereto, and
(ii) comparing the level of the at least one miRNA in the test sample to a reference level of the (said) at least one miRNA, e.g. 1, 2, 3, 4, 5, 6, 7, or 8 miRNA(s), which represents the maximal level of the at least one miRNA achievable in the patient by the therapeutic treatment of multiple sclerosis by the therapeutic treatment of multiple sclerosis.

It is also preferred that the method of determining the risk for a relapse of multiples sclerosis in a patient comprises the steps of:
(i) determining the level of at least one miRNA, e.g. 1, 2, 3, 4, 5, 6, or 7 miRNA(s), in a test sample isolated from the patient, wherein the nucleotide sequence of the at least one miRNA is selected from the group consisting of SEQ ID NO: 9 to SEQ ID NO: 15, a fragment thereof, and a sequence having at least 80% sequence identity thereto, and
(ii) comparing the level of the at least one miRNA in the test sample to a reference level of the (said) at least one miRNA, e.g. 1, 2, 3, 4, 5, 6, or 7 miRNA(s), which represents the minimal level of the at least one miRNA achievable in the patient by the therapeutic treatment of multiple sclerosis.

Said above mentioned maximal level or minimal level may be a single value achievable/achieved in a patient by the therapeutic treatment of multiple sclerosis, or may be an average value of said value achievable/achieved in a number of patients, particularly at least two patients, by the therapeutic treatment of multiple sclerosis. Further, said above mentioned maximal level or minimal level may be an average value achievable/achieved in a patient by the therapeutic treatment of multiple sclerosis, or may be an average value of said value achievable/achieved in a number of patients, particularly at least two patients, by the therapeutic treatment of multiple sclerosis.

In a further preferred embodiment, the (average) maximal level, particularly expression level, achievable/achieved regarding the miRNA having a nucleotide sequence according to SEQ ID NO: 1 is at least 1500, preferably at least 1643, SEQ ID NO: 2 is at least 800, preferably at least 978, SEQ ID NO: 3 is at least 4900, preferably at least 5061, SEQ ID NO: 4 is at least 9000, preferably at least 10489, SEQ ID NO: 5 is at least 300, preferably at least 406, SEQ ID NO: 6 is at least 1900, preferably at least 2035, SEQ ID NO: 7 is at least 6000, preferably at least 6722, or SEQ ID NO: 8 is at least 3500, preferably at least 462 in relative extinction units such as relative fluorescence units, and/or the (average) minimal level, particularly expression level, achievable/achieved as to the miRNA having a nucleotide sequence according to SEQ ID NO: 9 is at least 120, preferably at least 150, SEQ ID NO: 10 is at least 60, preferably at least 78, SEQ ID NO: 11 is at least 80, preferably at least 92, SEQ ID NO: 12 is at least 80, preferably at least 96, SEQ ID NO: 13 is at least 80, preferably at least 94, SEQ ID NO: 14 is at least 180, preferably at least 213, or SEQ ID NO: 15 is at least 120, preferably at least 156 in relative extinction units such as relative fluorescence units.

As to the definition of the terms "test sample" and "reference sample" and as to the preferred embodiments of the "test sample" and "reference sample", it is referred to the first aspect of the invention.

As mentioned above, it is preferred that the level of the at least one miRNA, e.g. 1, 2, 3, 4, 5, 6, 7, 8, 9, 10, 11, 12, 13, 14, or 15 miRNA(s), in the test sample is compared to a reference level of the (said) at least one miRNA. In addition, the preferred embodiments of the reference level and reference sample are described above.

In a preferred embodiment, the nucleotide sequence of the at least one miRNA, e.g. 1, 2, 3, 4, 5, 6, 7, or 8 miRNA(s), is selected from the group consisting of SEQ ID NO: 1 to SEQ ID NO: 8, a fragment thereof, and a sequence having at least 80% sequence identity thereto, preferably SEQ ID NO: 1, SEQ ID NO: 2, SEQ ID NO: 5 to SEQ ID NO: 8, a fragment thereof, and a sequence having at least 80% sequence identity thereto, more preferably SEQ ID NO: 1, SEQ ID NO: 2, a fragment thereof, and a sequence having at least 80% sequence identity thereto, wherein a decrease of the level of the at least one miRNA in the test sample when compared to the reference level of the at least one miRNA indicates a risk of the patient for a relapse of multiple sclerosis. More preferably, the miRNAs have nucleotide sequences according to SEQ ID NO: 1, a fragment thereof, or a sequence having at least 80% sequence identity thereto and according to SEQ ID NO: 2, a fragment thereof, or a sequence having at least 80% sequence identity thereto. In a particularly preferred embodiment, the nucleotide sequence of the at least one miRNA, e.g. 1 or 2 miRNA(s), is selected from the group consisting of SEQ ID NO: 3, SEQ ID NO: 4, a fragment thereof, and a sequence having at least 80% sequence identity thereto, wherein a decrease of the level of the at least one miRNA in the test sample when compared to the reference level of the at least one miRNA only indicates a risk of the patient for a relapse of multiple sclerosis when the level of at least one miRNA, e.g. 1 or 2 miRNA(s), selected from the group consisting of SEQ ID NO: 1, SEQ ID NO: 2, a fragment thereof, and a sequence having at least 80% sequence identity thereto in the test sample when compared to the reference level of the at least one miRNA is not increased.

In another preferred embodiment, the nucleotide sequence of the at least one miRNA, e.g. 1, 2, 3, 4, 5, 6, or 7 miRNA(s), is selected from the group consisting of SEQ ID NO: 9 to SEQ ID NO: 15, a fragment thereof, and a sequence having at least 80% sequence identity thereto, preferably SEQ ID NO: 10 to SEQ ID NO: 15, a fragment thereof, and a sequence having at least 80% sequence identity thereto, wherein an increase of the level of the at least one miRNA in the test sample when compared to the reference level of the at least one miRNA indicates a risk of the patient for a relapse of multiple sclerosis. In a particularly preferred embodiment, the nucleotide sequence of the at least one miRNA is SEQ ID NO: 9, a fragment thereof, and a sequence having at least 80% sequence identity thereto, wherein an increase of the level of the at least one miRNA in the test sample when compared to the reference level of the at least one miRNA only indicates a risk of the patient for a relapse of multiple sclerosis when the level of at least one miRNA, e.g. 1 or 2 miRNA(s), selected from the group consisting of SEQ ID NO: 1, SEQ ID NO: 2, a fragment thereof, and a sequence having at least 80% sequence identity thereto in the test sample when compared to the reference level of the at least one miRNA is not increased.

It is more preferred that the method of determining the risk for a relapse of multiples sclerosis in a patient comprises the steps of:
(i) determining the level of at least one miRNA, e.g. 1, 2, 3, 4, 5, 6, 7, or 8 miRNA(s), in a test sample isolated from the patient, wherein the nucleotide sequence of the at least one miRNA is selected from the group consisting of SEQ ID NO: 1 to SEQ ID NO: 8, a fragment thereof, and a sequence having at least 80% sequence identity thereto, preferably SEQ ID NO: 1, SEQ ID NO: 2, SEQ ID NO: 5 to SEQ ID NO: 8, a fragment thereof, and a sequence having at least 80% sequence identity thereto, more preferably SEQ ID NO: 1, SEQ ID NO: 2, a fragment thereof, and a sequence having at least 80% sequence identity thereto, and
(ii) comparing the level of the at least one miRNA in the test sample to a reference level of the at least one miRNA, e.g. 1, 2, 3, 4, 5, 6, 7, or 8 miRNA(s), which represents the maximal level of the at least one miRNA achievable/achieved in the patient by the therapeutic treatment of multiple sclerosis,
wherein a decrease of the level of said at least one miRNA in the test sample when compared to the reference level of said at least one miRNA indicates a risk of the patient for a relapse of multiple sclerosis, wherein said reference level.

It is most preferred that the nucleotide sequence of the at least one miRNA, e.g. 1 or 2 miRNA(s), is selected from the group consisting of SEQ ID NO: 3, SEQ ID NO: 4, a fragment thereof, and a sequence having at least 80% sequence identity thereto, wherein a decrease of the level of the at least one miRNA in the test sample when compared to the reference level of the at least one miRNA only indicates a risk of the patient for a relapse of multiple sclerosis when the level of at least one miRNA, e.g. 1 or 2 miRNA(s), selected from the group consisting of SEQ ID NO: 1, SEQ ID NO: 2, a fragment thereof, and a sequence having at least 80% sequence identity thereto in the test sample when compared to the reference level of the at least one miRNA is not increased.

It is also more preferred that the method of determining the risk for a relapse of multiples sclerosis in a patient comprises the steps of:
(i) determining the level of at least one miRNA, e.g. 1, 2, 3, 4, 5, 6, or 7 miRNA(s), in a test sample isolated from the patient, wherein the nucleotide sequence of the at least one miRNA is selected from the group consisting of SEQ ID NO: 9 to SEQ ID NO: 15, a fragment thereof, and a sequence having at least 80% sequence identity thereto, preferably SEQ ID NO: 10 to SEQ ID NO: 15, a fragment thereof, and a sequence having at least 80% sequence identity thereto, and
(ii) comparing the level of the at least one miRNA in the test sample to a reference level of the at least one miRNA, e.g. 1, 2, 3, 4, 5, 6, or 7 miRNA(s), which represents the minimal level of the at least one miRNA achievable/achieved in the patient by the therapeutic treatment of multiple sclerosis,
wherein an increase of the level of said at least one miRNA in the test sample when compared to the reference level of said at least one miRNA indicates a risk of the patient for a relapse of multiple sclerosis, wherein said reference level.

It is most preferred that the nucleotide sequence of the at least one miRNA is SEQ ID NO: 9, a fragment thereof, and a sequence having at least 80% sequence identity thereto, wherein an increase of the level of the at least one miRNA in the test sample when compared to the reference level of the at least one miRNA only indicates a risk of the patient for a relapse of multiple sclerosis when the level of at least one miRNA, e.g. 1 or 2 miRNA(s), selected from the group consisting of SEQ ID NO: 1, SEQ ID NO: 2, a fragment thereof, and a sequence having at least 80% sequence identity thereto in the test sample when compared to the reference level of the at least one miRNA is not increased.

The above method is a method of determining the risk of relapse of multiple sclerosis (MS) in a patient. Said patient may be a patient which receives or has received a therapeutic treatment of multiple sclerosis. Said therapeutic treatment may involve the application/administration of a drug for multiple sclerosis. Said drug may be selected from the group consisting of natalizumab, interferon beta 1a, interferon beta 1b, glatiramer acetate, alemtuzumab, fingolimod, dimethylfumarate, and mitoxantrone. In a preferred embodiment, the above method further comprises the step of administering a renewed dose of the drug or a dose of the drug which is increased compared to the previously administered dose of the drug when there is a risk of the patient for a relapse of multiple sclerosis. In another preferred embodiment, the above method further comprises the step of continuing the treatment of multiple sclerosis when there is a risk of the patient for a relapse of multiple sclerosis.

The above (in the context of the third aspect of the invention) mentioned nucleotide sequence of the miRNA is selected from the group consisting of
(i) a nucleotide sequence according to SEQ ID NO: 1 to SEQ ID NO: 15,
(ii) a nucleotide sequence that is a fragment of the nucleotide sequence according to (i), preferably, a nucleotide sequence that is a fragment which is between 1 and 12, more preferably between 1 and 8, and most preferably between 1 and 5 or 1 and 3, i.e. 1, 2, 3, 4, 5, 6, 7, 8, 9, 10, 11, or 12, nucleotides shorter than the nucleotide sequence according to (i), and
(iii) a nucleotide sequence that has at least 80%, preferably at least 85%, more preferably at least 90%, and most preferably at least 95% or 99%, i.e. 80, 81, 82, 83, 84, 85, 86, 87, 88, 89, 90, 91, 92, 93, 94, 95, 96, 97, 98, or 99%, sequence identity to the nucleotide sequence according to (i) or nucleotide sequence fragment according to (ii).

It is particularly preferred that the nucleotide sequence as defined in (iii) has at least 80%, preferably at least 85%, more preferably at least 90%, and most preferably at least 95% or 99%, i.e. 80, 81, 82, 83, 84, 85, 86, 87, 88, 89, 90, 91, 92, 93, 94, 95, 96, 97, 98, or 99%, sequence identity over a continuous stretch of at least 10, 11, 12, 13, 14, 15, 16, 17, 18, 19, 20 or more nucleotides, preferably over the whole length, to the nucleotide sequence of the nucleotide according to (i) or nucleotide fragment according to (ii).

In addition, the nucleotide sequence as defined in (ii) (i.e. nucleotide sequence fragment) or (iii) (i.e. nucleotide sequence variant or nucleotide sequence fragment variant) is only regarded as a nucleotide sequence as defined in (ii) (i.e. nucleotide sequence fragment) or (iii) (i.e. nucleotide sequence variant or nucleotide sequence fragment variant) within the context of the present invention, if it can still be bound, hybridized, recognized, or detected by a polynucleotide (probe) of complementary sequence, e.g. a polynucleotide (probe) which is complementary to the respective nucleotide sequence as defined in (i), through one or more types of chemical bonds, usually through complementary base pairing, usually through hydrogen bond formation under stringent hybridization conditions. The skilled person can readily assess whether a nucleotide sequence as defined in (ii) (i.e. nucleotide sequence fragment) or (iii) (i.e. nucleotide sequence variant or nucleotide sequence fragment variant) can still be bound, hybridized, recognized, or detected by a polynucleotide (probe) of complementary sequence, e.g. a polynucleotide (probe) which is complementary to the respective nucleotide sequence as defined in (i). Suitable assays to determine whether hybridization under stringent conditions still occurs are well known in the art. However, as an example, a suitable assay to determine whether hybridization still occurs comprises the steps of: (a) incubating a nucleotide sequence as defined in (ii) or (iii) labelled with biotin with a polynucleotide (probe) of complementary sequence, e.g. a polynucleotide (probe) which is complementary to the respective nucleotide sequence as defined in (i), wherein the polynucleotide (probe) is attached onto a biochip, under stringent hybridization conditions, (b) washing the biochip to remove unspecific bindings, (c) subjecting the biochip to a detection system, and (c) analyzing whether the nucleotide sequence can still be hybridized or detected by a polynucleotide (probe) of complementary sequence, e.g. a polynucleotide (probe) which is complementary to the respective nucleotide sequence as defined in (i). As a positive control, the respective miRNA as defined in (i) may be used. Preferably stringent hybridization conditions include the following: 50% formamide, 5×SSC, and 1% SDS, incubating at 42° C., or, 5×SSC, 1% SDS, incubating at 65° C., with wash in 0.2×SSC, and 0.1% SDS at 65° C.; or 6×SSPE, 10% formamide, 0.01%, Tween 20, 0.1×TE buffer, 0.5 mg/ml BSA, 0.1 mg/ml herring sperm DNA, incubating at 42° C. with wash in 0.5×SSPE and 6×SSPE at 45° C.

The patient may be any organism such as vertebrate, particularly any mammal, including both a human and another mammal, e.g. an animal such as a rodent, a rabbit, or a monkey. The rodent may be a mouse, rat, hamster, guinea pig, or chinchilla. Preferably, the patient is a human or a rodent.

Preferably, multiples sclerosis (MS) is relapsing-remitting multiple sclerosis (RR-MS), secondary progressive multiple sclerosis (SPMS), progressive relapsing multiple sclerosis (PRMS), or primary progressive multiple sclerosis (PPMS). More preferably, multiples sclerosis (MS) is relapsing-remitting multiple sclerosis (RR-MS).

As mentioned above, the method of determining the risk for a relapse of multiples sclerosis (MS) in a patient comprises the step of:
determining the level of at least one miRNA, e.g. 1, 2, 3, 4, 5, 6, 7, 8, 9, 10, 11, 12, 13, 14, or 15 miRNA(s), in a test sample isolated from the patient, wherein the nucleotide sequence of the at least one miRNA is selected from the group consisting of SEQ ID NO: 1 to SEQ ID NO: 15, a fragment thereof, and a sequence having at least 80% sequence identity thereto.

It is preferred that the level of the miRNA is the expression level. Said level of the miRNA, particularly expression level of the miRNA, may be indicated as (relative) miRNA concentration, (relative) miRNA amount, or (relative) miRNA extinction units such as relative fluorescence units.

Preferably the level of the miRNA, particularly the expression level of the miRNA, is determined by nucleic acid hybridization, nucleic acid amplification, polymerase extension, sequencing, mass spectroscopy or any combination thereof. More preferably, (i) the nucleic acid hybridization is performed using a microarray/biochip or beads, or using in situ hybridization, and/or (ii) the nucleic acid amplification is performed using real-time PCR. As to the above means to determine the level of the miRNA, particularly expression level of the miRNA, it is also referred to the first aspect of the invention.

In a preferred embodiment, the (expression) level of the at least one miRNA is determined by determining the level of the cDNA generated/transcribed from said miRNA. Preferably, said level is determined using a real time quantitative polymerase chain reaction (RT qPCR).

In another preferred embodiment, the level of the at least one miRNA is determined after a size selection of RNA which is smaller than 1000 base pairs, preferably smaller than 500 base pairs, more preferably smaller than 100 base pairs, and most preferably smaller than 30 base pairs. In a further preferred embodiment the level of the at least one miRNA is determined from a test sample that includes means for stabilizing the RNA-fraction, especially the small RNA fraction. Preferably, the means for stabilizing the RNA fraction, especially the small RNA-fraction have been either added to the test sample during or after blood collection (e.g. by adding RNAlater, or RNAretain) or were already included in the blood collection tube (e.g PAXgene tube, PAXgene blood RNA tube, or Tempus blood RNA tube)

It is preferred that the polynucleotide (probe) according to the sixth aspect of the invention or the polynucleotide set comprising at least two different polynucleotide (probes) according to the seventh aspect of the invention is used in the method of the third aspect of the invention to determine the level, particularly expression level, of at least one miRNA in a test sample isolated from the patient, wherein the nucleotide sequence of the at least one miRNA is selected from the group consisting of SEQ ID NO: 1 to SEQ ID NO: 15, a fragment thereof, and a sequence having at least 80% sequence identity thereto. It is particularly preferred that said polynucleotide is part of a biochip, or comprised on beads or microspheres or said at least two different polynucleotides are comprised on a biochip, or on a set of beads or microspheres.

In a fourth aspect, the present invention relates to a method of adjusting the dose of a therapeutic drug applied for therapeutic treatment of multiple sclerosis in a patient comprising the step of:

determining the level of at least one miRNA in a test sample isolated from the patient, wherein the nucleotide sequence of the at least one miRNA is selected from the group consisting of SEQ ID NO: 1 to SEQ ID NO: 15, a fragment thereof, and a sequence having at least 80% sequence identity thereto.

It is preferred that the level of the nucleotide sequence of the miRNA having SEQ ID NO: 1, SEQ ID NO: 2, SEQ ID NO: 3, SEQ ID NO: 4, SEQ ID NO: 9, a fragment thereof, or a sequence having at least 80% sequence identity thereto is determined. It is particularly preferred that the level of the nucleotide sequence of the miRNA having SEQ ID NO: 1, SEQ ID NO: 2, a fragment thereof, or a sequence having at least 80% sequence identity thereto is determined.

In an alternative embodiment, the level of the nucleotide sequence of the miRNA having SEQ ID NO: 3, a fragment thereof, or a sequence having at least 80% sequence identity thereto, and/or the level of the nucleotide sequence of the miRNA having SEQ ID NO: 9, a fragment thereof, or a sequence having at least 80% sequence identity thereto is not determined.

It is further preferred that the level of the nucleotide sequences of the miRNAs having SEQ ID NO: 1 to SEQ ID NO: 15, fragments thereof, or sequences having at least 80% sequence identity thereto is determined. It is particularly preferred that the level of the nucleotide sequences of the miRNAs having SEQ ID NO: 1 to SEQ ID NO: 8, fragments thereof, or sequences having at least 80% sequence identity thereto is determined or that the level of nucleotide sequences of the miRNAs having SEQ ID NO: 9 to SEQ ID NO: 15, fragments thereof, or sequences having at least 80% sequence identity thereto is determined. It is more preferred that the level of the nucleotide sequences of the miRNAs having SEQ ID NO: 1 to SEQ ID NO: 4 and SEQ ID NO: 9, fragments thereof, or sequences having at least 80% sequence identity thereto is determined. It is particularly more preferred that the level of the nucleotide sequences of the miRNAs having SEQ ID NO: 1 to SEQ ID NO: 4, fragments thereof, or sequences having at least 80% sequence identity thereto is determined. It is most preferred that the level of the nucleotide sequences of the miRNAs having (i) SEQ ID NO: 1 and SEQ ID NO: 2, fragments thereof, or sequence having at least 80% sequence identity thereto, (ii) SEQ ID NO: 1 and SEQ ID NO: 3, fragments thereof, or sequences having at least 80% sequence identity thereto, (iii) SEQ ID NO: 1 and SEQ ID NO: 4, fragments thereof, or sequences having at least 80% sequence identity thereto, (iv) SEQ ID NO: 2 and SEQ ID NO: 3, fragments thereof, or sequences having at least 80% sequence identity thereto, (v) SEQ ID NO: 2 and SEQ ID NO: 4, fragments thereof, or sequences having at least 80% sequence identity thereto, or (vi) SEQ ID NO: 3 and SEQ ID NO: 4, fragments thereof, or sequences having at least 80% sequence identity thereto is determined.

In case of the miRNA having a nucleotide sequence according to SEQ ID NO: 3, a fragment thereof, or a sequence having at least 80% sequence identity thereto, it is preferred that the level of this miRNA is only determined together with the level of at least one further miRNA having a nucleotide sequence selected from the group consisting of SEQ ID NO: 1, SEQ ID NO: 2, SEQ ID NO: 4 to SEQ ID NO: 15, a fragment thereof, and a sequence having at least 80% sequence identity thereto, particularly selected from the group consisting of SEQ ID NO: 1, SEQ ID NO: 2, SEQ ID NO: 4 to SEQ ID NO: 8, SEQ ID NO: 10 to SEQ ID NO: 15, a fragment thereof, and a sequence having at least 80% sequence identity thereto, or in case of the miRNA having a nucleotide sequence according to SEQ ID NO: 9, a fragment thereof, or a sequence having at least 80% sequence identity thereto, it is preferred that the level of this miRNA is only determined together with the level of at least one further miRNA having a nucleotide sequence selected from the group consisting of SEQ ID NO: 1 to SEQ ID NO: 8, SEQ ID NO: 10 to SEQ ID NO: 15, a fragment thereof, and a sequence having at least 80% sequence identity thereto, particularly selected from the group consisting of SEQ ID NO: 1, SEQ ID NO: 2, SEQ ID NO: 4 to SEQ ID NO: 8, SEQ ID NO: 10 to SEQ ID NO: 15, a fragment thereof, and a sequence having at least 80% sequence identity thereto. In addition, in case of miRNAs having nucleotide sequences according to SEQ ID NO: 3, SEQ ID NO: 9, a fragment thereof, or a sequence having at least 80% sequence identity thereto, it is preferred that the level of these miRNA is only determined together with the level of at least one further miRNA having a nucleotide sequence selected from the group consisting of SEQ ID NO: 1, SEQ ID NO: 2, SEQ ID NO: 4 to SEQ ID NO: 8, SEQ ID NO: 10 to SEQ ID NO: 15, a fragment thereof, and a sequence having at least 80% sequence identity thereto. Other preferred miRNA combinations are listed in FIG. 8.

It is preferred that the patient is a patient to whom a drug applied for therapeutic treatment is administered or has been administered. The drug applied for therapeutic treatment may be selected from the group consisting of natalizumab, interferon beta 1a, interferon beta 1b, glatiramer acetate, alemtuzumab, fingolimod, dimethylfumarate, and mitoxantrone. Preferably, the drug is natalizumab. The way of administration may be oral, nasal, rectal, parenteral, vaginal, or topical. Parental administration includes subcutaneous, intracutaneous, intramuscular, intravenous or intraperitoneal administration.

The dose of the drug applied for therapeutic treatment may be lower compared to a previous therapeutic treatment. Said dose may be about at least 10, 20, 30, 40, 50, 60, 70, or 80% lower compared to a previous therapeutic treatment. For example, the dose that is administered or that has been administered to the human patient may be about at least 0.5, 1, 1.5, 2, 2.5, 3, 3.5, 4, or 5 mg per kg bodyweight lower compared to a previous therapeutic treatment. The human patient may have received a dose of between 1 mg to 10 mg per kg bodyweight, e.g. 3 or 6 mg per kg bodyweight, in a previous therapeutic treatment.

It is also (alternatively or additionally) preferred that the level of the at least one miRNA, e.g. 1, 2, 3, 4, 5, 6, 7, 8, 9, 10, 11, 12, 13, 14, or 15 miRNA(s), in the test sample is compared to a reference level of the (said) at least one miRNA. Thus, in a preferred embodiment, the method of adjusting the dose of a therapeutic drug applied for therapeutic treatment of multiple sclerosis in a patient comprises the steps of:
(i) determining the level of at least one miRNA, e.g. 1, 2, 3, 4, 5, 6, 7, 8, 9, 10, 11, 12, 13, 14, or 15 miRNA(s), in a test sample isolated from the patient, wherein the nucleotide sequence of the at least one miRNA is selected from the group consisting of SEQ ID NO: 1 to SEQ ID NO: 15, a fragment thereof, and a sequence having at least 80% sequence identity thereto, and
(ii) comparing the level of the at least one miRNA in the test sample to a reference level of the (said) at least one miRNA, e.g. 1, 2, 3, 4, 5, 6, 7, 8, 9, 10, 11, 12, 13, 14, or 15 miRNA(s).

As mentioned above, it is preferred that the patient is a patient to whom a drug applied for therapeutic treatment is administered or has been administered. The drug applied for therapeutic treatment may be selected from the group consisting of natalizumab, interferon beta 1a, interferon beta 1b, glatiramer acetate, alemtuzumab, fingolimod, dimethylfumarate, and mitoxantrone. Preferably, the drug is natalizumab. The way of administration may be oral, nasal, rectal, parenteral, vaginal, or topical. Parental administration includes subcutaneous, intracutaneous, intramuscular, intravenous or intraperitoneal administration.

In a preferred embodiment, the reference level is the level of the (said) at least one miRNA, e.g. 1, 2, 3, 4, 5, 6, 7, 8, 9, 10, 11, 12, 13, 14, or 15 miRNA(s), determined empirically by measuring a number of reference samples, preferably at least two reference samples, more preferably at least 2 to 40 reference samples, even more preferably at least 10 to 60 reference samples, and most preferably at least 50 to 100 reference samples, e.g. at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 reference samples, from (different) patients. Preferably or alternatively, said reference level is an average level. The average level is particularly determined by measuring a number of reference samples, preferably at least two reference samples, more preferably at least 2 to 40 reference samples, even more preferably at least 10 to 60 reference samples, and most preferably at least 50 to 100 reference samples, e.g. at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 reference samples, from a number of patients and calculating the "middle" value (e.g. median or mean value) of the reference levels determined therein. Preferably, said reference samples are samples from multiple sclerosis patients, e.g. relapsing-remitting multiple sclerosis (RR-MS), secondary progressive multiple sclerosis (SPMS), progressive relapsing multiple sclerosis (PRMS), or primary progressive multiple sclerosis (PPMS) patients, or said reference samples are samples from successfully treated multiple sclerosis patients, e.g. successfully treated relapsing-remitting multiple sclerosis (RR-MS), secondary progressive multiple sclerosis (SPMS), progressive relapsing multiple sclerosis (PRMS), or primary progressive multiple sclerosis (PPMS) patients. As to the definition of the term "multiple sclerosis (MS), e.g. RR-MS, SP-MS, PR-MS, or PP-MS, patients", it is referred to the first aspect of the invention. Further, as to the definition of the term "successfully treated (MS), e.g. RR-MS, SP-MS, PR-MS, or PP-MS, patients", it is referred to the second aspect of the invention.

It is also (alternatively or additionally) preferred that the reference level is determined in a reference sample isolated from the patient, particularly prior to the isolation of the test sample. For example, the reference level is the level of the (said) at least one miRNA, e.g. 1, 2, 3, 4, 5, 6, 7, 8, 9, 10, 11, 12, 13, 14, or 15 miRNA(s), determined empirically by measuring a number of reference samples, particularly at least two reference samples, from patients and the reference level is determined in the reference sample isolated from the patient prior to the isolation of the test sample. Further, for example, the reference level is the level of the (said) at least one miRNA, e.g. 1, 2, 3, 4, 5, 6, 7, 8, 9, 10, 11, 12, 13, 14, or 15 miRNA(s), determined empirically by measuring a number of reference samples, particularly at least two reference samples, from patients, said reference samples are samples from multiple sclerosis patients, e.g. relapsing-remitting multiple sclerosis (RR-MS), secondary progressive multiple sclerosis (SPMS), progressive relapsing multiple sclerosis (PRMS), or primary progressive multiple sclerosis (PPMS) patients, and the reference level is determined in the reference sample isolated from the patient prior to the isolation of the test sample. It is preferred that the reference sample is isolated from the patient in a time period of between 9 months and 1 day or between 6 months and 1 day prior to the isolation of the test sample, it is more preferred that the reference sample is isolated from the patient in a time period of between 3 months and 1 day prior to the isolation of the test sample, it is even more preferred that the reference sample is isolated from the patient in a time period of between 1 month and 1 day prior to the isolation of the test sample, and it is most preferred that the reference sample is isolated from the patient in a time period of between 3 weeks and 1 day prior to the isolation of the test sample, e.g. 1, 2, 3, 4, 5, 6 day(s), 1, 2, 3 week(s), 1, 2, 3 4, 5, 6, 7, 8, or 9 month(s) prior to the isolation of the test sample.

It is particularly preferred that said reference sample and said test sample are isolated during therapeutic treatment of multiple sclerosis. Particularly, the reference sample and the test sample are isolated during therapeutic treatment from different patients. For example, the test sample may be isolated during therapeutic treatment of multiple sclerosis in a patient whose dose of a therapeutic drug may be adjusted and the reference sample may be isolated during therapeutic treatment of multiple sclerosis in a patient whose reference level is measured to subsequently determine an empirical reference level, particular average level, on the basis of a number of reference levels of patients. It is further particularly preferred that said reference sample and said test sample are isolated during therapeutic treatment of multiple sclerosis, wherein said test sample is isolated during the therapeutic treatment of multiple sclerosis with a lower dose of the therapeutic drug compared to the reference sample. Thus, said reference sample comprises a higher dose of the therapeutic drug compared to the test sample. Said drug may be selected from the group consisting of natalizumab, interferon beta 1a, interferon beta 1b, glatiramer acetate, alemtuzumab, fingolimod, dimethylfumarate, and mitoxantrone. It is particularly preferred that the drug is natalizumab. Said dose may be about at least 10, 20, 30, 40, 50, 60, 70, or 80% lower compared to the reference sample.

In an alternative preferred embodiment, the reference level is the level of the (said) at least one miRNA, e.g. 1, 2, 3, 4, 5, 6, 7, 8, 9, 10, 11, 12, 13, 14, or 15 miRNA(s), determined in a reference sample isolated from the same patient. Particularly, the reference level is determined in a reference sample isolated from the same patient prior to the isolation of the test sample. Preferably, said (multiple sclerosis) patient is a relapsing-remitting multiple sclerosis (RR-MS), secondary progressive multiple sclerosis (SPMS), progressive relapsing multiple sclerosis (PRMS), or primary progressive multiple sclerosis (PPMS) patient. It is also preferred that said multiple sclerosis patient is a successfully treated multiple sclerosis patient, e.g. a successfully treated relapsing-remitting multiple sclerosis (RR-MS), secondary progressive multiple sclerosis (SPMS), progressive relapsing multiple sclerosis (PRMS), or primary progressive multiple sclerosis (PPMS) patient. As to the definition of the term "multiple sclerosis (MS), e.g. RR-MS, SP-MS, PR-MS, or PP-MS, patient", it is referred to the first aspect of the invention. Further, as to the definition of the term "successfully treated multiple sclerosis (MS), e.g. RR-MS, SP-MS, PR-MS, or PP-MS, patient", it is referred to the second aspect of the invention. For example, the reference level is the level of the (said) at least one miRNA, e.g. 1, 2, 3, 4, 5, 6, 7, 8, 9, 10, 11, 12, 13, 14, or 15 miRNA(s), determined in a reference sample isolated from the same patient, particularly prior to the isolation of the test sample, and said patient is a relapsing-remitting multiple sclerosis (RR-MS) patient, secondary progressive multiple sclerosis (SPMS) patient, progressive relapsing multiple sclerosis (PRMS) patient, or primary progressive multiple sclerosis (PPMS) patient. It is preferred that the reference sample is isolated from the same patient in a time period of between 9 months and 1 day or between 6 months and 1 day prior to the isolation of the test sample, it is more preferred that the reference sample is isolated from the same patient in a time period of between 3 months and 1 day prior to the isolation of the test sample, it is even more preferred that the reference sample is isolated from the same patient in a time period of between 1 month and 1 day prior to the isolation of the test sample, and it is most preferred that the reference sample is isolated from the same patient in a time period of between 3 weeks and 1 day prior to the isolation of the test sample, e.g. 1, 2, 3, 4, 5, 6 day(s), 1, 2, 3 week(s), 1, 2, 3 4, 5, 6, 7, 8, or 9 month(s) prior to the isolation of the test sample.

It is particularly preferred that said reference sample and said test sample are isolated during therapeutic treatment of multiple sclerosis. Particularly, the reference sample and the test sample are isolated during therapeutic treatment from the same patient. It is further particularly preferred that said reference sample and said test sample are isolated during therapeutic treatment of multiple sclerosis, particularly from the same patient, wherein said test sample is isolated during the therapeutic treatment of multiple sclerosis with a lower dose of the therapeutic drug compared to the reference sample. Thus, said reference sample comprises a higher dose of the therapeutic drug compared to the test sample. Said drug may be selected from the group consisting of natalizumab, interferon beta 1a, interferon beta 1b, glatiramer acetate, alemtuzumab, fingolimod, dimethylfumarate, and mitoxantrone. It is particularly preferred that the drug is natalizumab. Said dose may be about at least 10, 20, 30, 40, 50, 60, 70, or 80% lower compared to the reference sample.

As to the definition of the terms "test sample" and "reference sample" and as to the preferred embodiments of the "test sample" and "reference sample", it is referred to the first aspect of the invention.

As mentioned above, it is preferred that the level of the at least one miRNA, e.g. 1, 2, 3, 4, 5, 6, 7, 8, 9, 10, 11, 12, 13, 14, or 15 miRNA(s), in the test sample is compared to a reference level of the (said) at least one miRNA. In addition, the preferred embodiments of the reference level and reference sample are described above.

In a preferred embodiment, the nucleotide sequence of the at least one miRNA, e.g. 1, 2, 3, 4, 5, 6, 7, or 8 miRNA(s), is selected from the group consisting of SEQ ID NO: 1 to SEQ ID NO: 8, a fragment thereof, and a sequence having at least 80% sequence identity thereto, preferably SEQ ID NO: 1, SEQ ID NO: 2, SEQ ID NO: 5 to SEQ ID NO: 8, a fragment thereof, and a sequence having at least 80% sequence identity thereto, more preferably SEQ ID NO: 1, SEQ ID NO: 2, a fragment thereof, and a sequence having at least 80% sequence identity thereto, wherein an increase or a maintenance of the level of the at least one miRNA in the test sample when compared to the reference level of the at least one miRNA indicates that the dose of the therapeutic drug applied for treating multiple sclerosis in the patient is sufficient and can optionally be lowered, particularly further be lowered. More preferably, the miRNAs have nucleotide sequences according to SEQ ID NO: 1, a fragment thereof, or a sequence having at least 80% sequence identity thereto and according to SEQ ID NO: 2, a fragment thereof, or a sequence having at least 80% sequence identity thereto. In a particularly preferred embodiment, the nucleotide sequence of the at least one miRNA, e.g. 1 or 2 miRNA(s), is selected from the group consisting of SEQ ID NO: 3, SEQ ID NO: 4, a fragment thereof, and a sequence having at least 80% sequence identity thereto, wherein an increase or a maintenance of the level of the at least one miRNA in the test sample when compared to the reference level of the at least one miRNA only indicates that the dose of the therapeutic drug applied for treating multiple sclerosis in the patient is sufficient and can optionally be lowered, particularly further be lowered, when the level of at least one miRNA, e.g. 1 or 2 miRNA(s), selected from the group consisting of SEQ ID NO: 1, SEQ ID NO: 2, a fragment thereof, and a sequence having at least 80% sequence identity thereto in the test sample when compared to the reference level of the at least one miRNA is not decreased or is maintained.

In another preferred embodiment, the nucleotide sequence of the at least one miRNA, e.g. 1, 2, 3, 4, 5, 6, or 7 miRNA(s), is selected from the group consisting of SEQ ID NO: 9 to SEQ ID NO: 15, a fragment thereof, and a sequence having at least 80% sequence identity thereto, preferably SEQ ID NO: 10 to SEQ ID NO: 15, a fragment thereof, and a sequence having at least 80% sequence identity thereto, wherein a decrease or a maintenance of the level of the at least one miRNA in the test sample when compared to the reference level of the at least one miRNA indicates that the dose of the therapeutic drug applied for treating multiple sclerosis in the patient is sufficient and can optionally be lowered, particularly further be lowered. In a particularly preferred embodiment, the nucleotide sequence of the at least one miRNA is SEQ ID NO: 9, a fragment thereof, and a sequence having at least 80% sequence identity thereto, wherein a decrease or a maintenance of the level of the at least one miRNA in the test sample when compared to the reference level of the at least one miRNA only indicates that the dose of the therapeutic drug applied for treating multiple sclerosis in the patient is sufficient and can optionally be lowered, particularly further be lowered, when the level of at least one miRNA, e.g. 1 or 2 miRNA(s), selected from the group consisting of SEQ ID NO: 1, SEQ ID NO: 2, a fragment thereof, and a sequence having at least 80% sequence identity thereto in the test sample when compared to the reference level of the at least one miRNA is not decreased or is maintained.

The term "that the level of the at least one miRNA in the test sample when compared to the reference level of the at least one miRNA is maintained" may mean that the level of the at least one miRNA in the test sample when compared to the reference level varies between >0 to 20%, preferably between >0 to 10%, more preferably between >0 to 5% or between >0 to 3%, e.g. 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, or 20%. Most preferably, the level of the at least ne miRNA in the test sample when compared to the reference level does not vary or is constant.

More preferably,
(i) an at least 1.2 fold increase, preferably an at least 1.4 fold increase, of the level of the miRNA having a nucleotide sequence according to SEQ ID NO: 1, an at least 1.2 fold increase, preferably an at least 1.4 fold increase, of the level of the miRNA having a nucleotide sequence according to SEQ ID NO: 2, an at least 1.2 fold increase, preferably an at least 1.4 fold increase, of the level of the miRNA having a nucleotide sequence according to SEQ ID NO: 3, an at least 1.2 fold increase, preferably an at least 1.4 fold increase, of the level of the miRNA having a nucleotide sequence according to SEQ ID NO: 4, an at least 1.2 fold increase, preferably an at least 1.4 fold increase, of the level of the miRNA having a nucleotide sequence according to SEQ ID NO: 5, an at least 1.2 fold increase, preferably an at least 1.4 fold increase, of the level of the miRNA having a nucleotide sequence according to SEQ ID NO: 6, an at least 1.2 fold increase, preferably an at least 1.4 fold increase, of the level of the miRNA having a nucleotide sequence according to SEQ ID NO: 7, and/or an at least 1.2 fold increase, preferably an at least 1.4 fold increase, of the level of the miRNA having a nucleotide sequence according to SEQ ID NO: 8 indicates that the dose of the therapeutic drug applied for treating multiple sclerosis in the patient is sufficient and can optionally be lowered, particularly further be lowered, and/or
(ii) an at least 1.2 fold decrease, preferably an at least 1.4 fold decrease, of the level of the miRNA having a nucleotide sequence according to SEQ ID NO: 9, an at least 1.2 fold decrease, preferably an at least 1.4 fold decrease, of the level of the miRNA having a nucleotide sequence according to SEQ ID NO: 10, an at least 1.2 fold decrease, preferably an at least 1.4 fold decrease, of the level of the miRNA having a nucleotide sequence according to SEQ ID NO: 11, an at least 1.2 fold decrease, preferably an at least 1.4 fold decrease, of the level of the miRNA having a nucleotide sequence according to SEQ ID NO: 12, an at least 1.2 fold decrease, preferably an at least 1.4 fold decrease, of the level of the miRNA having a nucleotide sequence according to SEQ ID NO: 13, an at least 1.2 fold decrease, preferably an at least 1.4 fold decrease, of the level of the miRNA having a nucleotide sequence according to SEQ ID NO: 14, and/or an at least 1.2 fold decrease, preferably an at least 1.4 fold decrease, of the level of the miRNA having a nucleotide sequence according to SEQ ID NO: 15 indicates that the dose of the therapeutic drug applied for treating multiple sclerosis in the patient is sufficient and can optionally be lowered, particularly further be lowered.

In an alternative preferred embodiment, the nucleotide sequence of the at least one miRNA, e.g. 1, 2, 3, 4, 5, 6, 7, or 8 miRNA(s), is selected from the group consisting of SEQ ID NO: 1 to SEQ ID NO: 8, a fragment thereof, and a sequence having at least 80% sequence identity thereto, preferably SEQ ID NO: 1, SEQ ID NO: 2, SEQ ID NO: 5 to SEQ ID NO: 8, a fragment thereof, and a sequence having at least 80% sequence identity thereto, more preferably SEQ ID NO: 1, SEQ ID NO: 2, a fragment thereof, and a sequence having at least 80% sequence identity thereto, wherein a decrease of the level of the at least one miRNA in the test sample when compared to the reference level of the at least one miRNA indicates that the dose of the therapeutic drug applied for treating multiple sclerosis in the patient is not sufficient and can optionally be increased, particularly increased again. More preferably, the miRNAs have nucleotide sequences according to SEQ ID NO: 1, a fragment thereof, or a sequence having at least 80% sequence identity thereto and according to SEQ ID NO: 2, a fragment thereof, or a sequence having at least 80% sequence identity thereto. In a particularly preferred embodiment, the nucleotide sequence of the at least one miRNA, e.g. 1 or 2 miRNA(s), is selected from the group consisting of SEQ ID NO: 3, SEQ ID NO: 4, a fragment thereof, and a sequence having at least 80% sequence identity thereto, wherein a decrease of the level of the at least one miRNA in the test sample when compared to the reference level of the at least one miRNA only indicates that the dose of the therapeutic drug applied for treating multiple sclerosis in the patient is not sufficient and can optionally be increased, particularly increased again, when the level of at least one miRNA, e.g. 1 or 2 miRNA(s), selected from the group consisting of SEQ ID NO: 1, SEQ ID NO: 2, a fragment thereof, and a sequence having at least 80% sequence identity thereto in the test sample when compared to the reference level of the at least one miRNA is not increased.

In another alternative preferred embodiment, the nucleotide sequence of the at least one miRNA, e.g. 1, 2, 3, 4, 5, 6, or 7 miRNA(s), is selected from the group consisting of SEQ ID NO: 9 to SEQ ID NO: 15, a fragment thereof, and a sequence having at least 80% sequence identity thereto, preferably SEQ ID NO: 10 to SEQ ID NO: 15, a fragment thereof, and a sequence having at least 80% sequence identity thereto, wherein an increase of the level of the at least one miRNA in the test sample when compared to the reference level of the at least one miRNA indicates that the dose of the therapeutic drug applied for treating multiple sclerosis in the patient is not sufficient and can optionally be increased, particularly increased again. In a particularly preferred embodiment, the nucleotide sequence of the at least one miRNA is SEQ ID NO: 9, a fragment thereof, and a sequence having at least 80% sequence identity thereto, wherein an increase of the level of the at least one miRNA in the test sample when compared to the reference level of the at least one miRNA only indicates that the dose of the therapeutic drug applied for treating multiple sclerosis in the patient is not sufficient and can optionally be increased, particularly increased again, when the level of at least one miRNA, e.g. 1 or 2 miRNA(s), selected from the group consisting of SEQ ID NO: 1, SEQ ID NO: 2, a fragment thereof, and a sequence having at least 80% sequence identity thereto in the test sample when compared to the reference level of the at least one miRNA is not increased.

Preferably, the above mentioned method steps can be carried out several times by further lowering the dose of the test sample compared to the reference sample to estimate whether the dose of the therapeutic drug is still sufficient for treating multiple sclerosis in the patient and whether optionally the dose can further be lowered or can be increased again.

The above method is a method of adjusting the dose of a therapeutic drug applied for therapeutic treatment of multiple sclerosis. Said patient may be a patient to whom a drug applied for therapeutic treatment is administered or has been administered. The drug applied for therapeutic treatment may be selected from the group consisting of natalizumab, interferon beta 1a, interferon beta 1b, glatiramer acetate, alemtuzumab, fingolimod, dimethylfumarate, and mitoxantrone. In a preferred embodiment, the above method further comprises the step of administering (i) a renewed dose of the drug when it is indicated that the dose of the therapeutic drug applied for treating multiple sclerosis in the patient is sufficient, (ii) a dose of the drug which is decreased compared to the previously administered dose of the drug when it is indicated that the dose of the therapeutic drug applied for treating multiple sclerosis in the patient can (further) be lowered, (iii) a dose of the drug which is increased compared to the previously administered dose of the drug when it is indicated that the dose of the therapeutic drug applied for treating multiple sclerosis in the patient is not sufficient, or (iv) a dose of the drug which is increased compared to the previously administered dose of the drug when it is indicated that the dose of the therapeutic drug applied for treating multiple sclerosis in the patient can be increased (again). Alternatively, when it is indicated that the dose of the therapeutic drug applied for treating multiple sclerosis in the patient is not sufficient, the administered drug may be changed, i.e. another drug (e.g. selected from the group consisting of natalizumab, interferon beta 1a, interferon beta 1b, glatiramer acetate, alemtuzumab, fingolimod, dimethylfumarate, and mitoxantrone) may be administered. In another preferred embodiment, the above method further comprises the step of continuing the treatment of multiple sclerosis when it is indicated that the dose of the therapeutic drug applied for treating multiple sclerosis in the patient is sufficient, or discontinuing the treatment of multiple sclerosis when it is indicated that the dose of the therapeutic drug applied for treating multiple sclerosis in the patient is not sufficient. In the latter case, the administered drug may be changed, i.e. another drug (e.g. selected from the group consisting of natalizumab, interferon beta 1a, interferon beta 1b, glatiramer acetate, alemtuzumab, fingolimod, dimethylfumarate, and mitoxantrone) may be administered.

The above (in the context of the fourth aspect of the invention) mentioned nucleotide sequence of the miRNA is selected from the group consisting of
(i) a nucleotide sequence according to SEQ ID NO: 1 to SEQ ID NO: 15,
(ii) a nucleotide sequence that is a fragment of the nucleotide sequence according to (i), preferably, a nucleotide sequence that is a fragment which is between 1 and 12, more preferably between 1 and 8, and most preferably between 1 and 5 or 1 and 3, i.e. 1, 2, 3, 4, 5, 6, 7, 8, 9, 10, 11, or 12, nucleotides shorter than the nucleotide sequence according to (i), and
(iii) a nucleotide sequence that has at least 80%, preferably at least 85%, more preferably at least 90%, and most preferably at least 95% or 99%, i.e. 80, 81, 82, 83, 84, 85, 86, 87, 88, 89, 90, 91, 92, 93, 94, 95, 96, 97, 98, or 99%, sequence identity to the nucleotide sequence according to (i) or nucleotide sequence fragment according to (ii).

It is particularly preferred that the nucleotide sequence as defined in (iii) has at least 80%, preferably at least 85%, more preferably at least 90%, and most preferably at least 95% or 99%, i.e. 80, 81, 82, 83, 84, 85, 86, 87, 88, 89, 90, 91, 92, 93, 94, 95, 96, 97, 98, or 99%, sequence identity over a continuous stretch of at least 10, 11, 12, 13, 14, 15, 16, 17, 18, 19, 20 or more nucleotides, preferably over the whole length, to the nucleotide sequence of the nucleotide according to (i) or nucleotide fragment according to (ii).

In addition, the nucleotide sequence as defined in (ii) (i.e. nucleotide sequence fragment) or (iii) (i.e. nucleotide sequence variant or nucleotide sequence fragment variant) is only regarded as a nucleotide sequence as defined in (ii) (i.e. nucleotide sequence fragment) or (iii) (i.e. nucleotide sequence variant or nucleotide sequence fragment variant) within the context of the present invention, if it can still be bound, hybridized, recognized, or detected by a polynucleotide (probe) of complementary sequence, e.g. a polynucleotide (probe) which is complementary to the respective nucleotide sequence as defined in (i), through one or more types of chemical bonds, usually through complementary base pairing, usually through hydrogen bond formation under stringent hybridization conditions. The skilled person can readily assess whether a nucleotide sequence as defined in (ii) (i.e. nucleotide sequence fragment) or (iii) (i.e. nucleotide sequence variant or nucleotide sequence fragment variant) can still be bound, hybridized, recognized, or detected by a polynucleotide (probe) of complementary sequence, e.g. a polynucleotide (probe) which is complementary to the respective nucleotide sequence as defined in (i). Suitable assays to determine whether hybridization under stringent conditions still occurs are well known in the art. However, as an example, a suitable assay to determine whether hybridization still occurs comprises the steps of: (a) incubating a nucleotide sequence as defined in (ii) or (iii) labelled with biotin with a polynucleotide (probe) of complementary sequence, e.g. a polynucleotide (probe) which is complementary to the respective nucleotide sequence as defined in (i), wherein the polynucleotide (probe) is attached onto a biochip, under stringent hybridization conditions, (b) washing the biochip to remove unspecific bindings, (c) subjecting the biochip to a detection system, and (c) analyzing whether the nucleotide sequence can still be hybridized or detected by a polynucleotide (probe) of complementary sequence, e.g. a polynucleotide (probe) which is complementary to the respective nucleotide sequence as defined in (i). As a positive control, the respective miRNA as defined in (i) may be used. Preferably stringent hybridization conditions include the following: 50% formamide, 5×SSC, and 1% SDS, incubating at 42° C., or, 5×SSC, 1% SDS, incubating at 65° C., with wash in 0.2×SSC, and 0.1% SDS at 65° C.; or 6×SSPE, 10% formamide, 0.01%, Tween 20, 0.1×TE buffer, 0.5 mg/ml BSA, 0.1 mg/ml herring sperm DNA, incubating at 42° C. with wash in 0.5×SSPE and 6×SSPE at 45° C.

The patient may be any organism such as vertebrate, particularly any mammal, including both a human and another mammal, e.g. an animal such as a rodent, a rabbit, or a monkey. The rodent may be a mouse, rat, hamster, guinea pig, or chinchilla. Preferably, the patient is a human or a rodent.

Preferably, multiples sclerosis (MS) is relapsing-remitting multiple sclerosis (RR-MS), secondary progressive multiple sclerosis (SPMS), progressive relapsing multiple sclerosis (PRMS), or primary progressive multiple sclerosis (PPMS). More preferably, multiples sclerosis (MS) is relapsing-remitting multiple sclerosis (RR-MS).

As mentioned above, the method of adjusting the does of a therapeutic drug applied for therapeutic treatment of multiple sclerosis (MS) in a patient comprises the step of: determining the level of at least one miRNA, e.g. 1, 2, 3, 4, 5, 6, 7, 8, 9, 10, 11, 12, 13, 14, or 15 miRNA(s), in a test sample isolated from the patient, wherein the nucleotide sequence of the at least one miRNA is selected from the group consisting of SEQ ID NO: 1 to SEQ ID NO: 15, a fragment thereof, and a sequence having at least 80% sequence identity thereto.

It is preferred that the level of the miRNA is the expression level. Said level of the miRNA, particularly expression level of the miRNA, may be indicated as (relative) miRNA concentration, (relative) miRNA amount, or (relative) miRNA extinction units such as relative fluorescence units.

Preferably the level of the miRNA, particularly the expression level of the miRNA, is determined by nucleic acid hybridization, nucleic acid amplification, polymerase extension, sequencing, mass spectroscopy or any combination thereof. More preferably, (i) the nucleic acid hybridization is performed using a microarray/biochip or beads, or using in situ hybridization, and/or (ii) the nucleic acid amplification is performed using real-time PCR. As to the above means to determine the level of the miRNA, particularly expression level of the miRNA, it is also referred to the first aspect of the invention.

In a preferred embodiment, the (expression) level of the at least one miRNA is determined by determining the level of the cDNA generated/transcribed from said miRNA. Preferably, said level is determined using a real time quantitative polymerase chain reaction (RT qPCR).

In another preferred embodiment, the level of the at least one miRNA is determined after a size selection of RNA which is smaller than 1000 base pairs, preferably smaller than 500 base pairs, more preferably smaller than 100 base pairs, and most preferably smaller than 30 base pairs.

In a further preferred embodiment the level of the at least one miRNA is determined from a test sample that includes means for stabilizing the RNA-fraction, especially the small RNA fraction. Preferably, the means for stabilizing the RNA fraction, especially the small RNA-fraction have been either added to the test sample during or after blood collection (e.g. by adding RNAlater, or RNAretain) or were already included in the blood collection tube (e.g PAXgene tube, PAXgene blood RNA tube, or Tempus blood RNA tube)

It is preferred that the polynucleotide (probe) according to the sixth aspect of the invention or the polynucleotide set comprising at least two different polynucleotide (probes) according to the seventh aspect of the invention is used in the method according to the fourth aspect of the invention to determine the level, particularly expression level, of at least one miRNA in a test sample isolated from the patient, wherein the nucleotide sequence of the at least one miRNA is selected from the group consisting of SEQ ID NO: 1 to SEQ ID NO: 15, a fragment thereof, and a sequence having at least 80% sequence identity thereto. It is particularly preferred that said polynucleotide is part of a biochip, or comprised on beads or microspheres or said at least two different polynucleotides are comprised on a biochip, or on a set of beads or microspheres.

In a fifth aspect, the present invention relates to a method of identifying a compound suitable for the treatment of multiple sclerosis in a patient comprising the steps of:
(i) providing a test system comprising at least one miRNA, e.g. 1, 2, 3, 4, 5, 6, 7, 8, 9, 10, 11, 12, 13, 14, or 15 miRNA(s), wherein the nucleotide sequence of the at least one miRNA is selected from the group consisting of SEQ ID NO: 1 to SEQ ID NO: 15, a fragment thereof, and a sequence having at least 80% sequence identity thereto,
(ii) contacting the test system with a test compound, and
(iii) determining the effect of the test compound on the test system, wherein the test compound is identified as a compound suitable for the treatment of multiple sclerosis in the patient, when a significant effect of the test compound on the test system relative to a control is detected.

It is preferred that the miRNA comprised in the test system has a nucleotide sequence according to SEQ ID NO: 1, SEQ ID NO: 2, SEQ ID NO: 3, SEQ ID NO: 4, SEQ ID NO: 9, a fragment thereof, or a sequence having at least 80% sequence identity thereto. It is particularly preferred that the miRNA comprised in the test system has a nucleotide sequence according to SEQ ID NO: 1, SEQ ID NO: 2, a fragment thereof, or a sequence having at least 80% sequence identity thereto.

In an alternative embodiment, the level of the nucleotide sequence of the miRNA having SEQ ID NO: 3, a fragment thereof, or a sequence having at least 80% sequence identity thereto, and/or the level of the nucleotide sequence of the miRNA having SEQ ID NO: 9, a fragment thereof, or a sequence having at least 80% sequence identity thereto is not determined.

It is further preferred that the miRNAs comprised in the test system have nucleotide sequences according to SEQ ID NO: 1 to SEQ ID NO: 15, fragments thereof, or sequences having at least 80% sequence identity thereto. It is particularly preferred that the miRNAs comprised in the test system have nucleotide sequences according to SEQ ID NO: 1 to SEQ ID NO: 8, fragments thereof, or sequences having at least 80% sequence identity thereto, or have nucleotide sequences according to SEQ ID NO: 9 to SEQ ID NO: 15, fragments thereof, or sequences having at least 80% sequence identity thereto. It is more preferred that the miRNAs comprised in the test system have nucleotide sequences according to SEQ ID NO: 1 to SEQ ID NO: 4 and SEQ ID NO: 9, fragments thereof, or sequences having at least 80% sequence identity thereto. It is particularly more preferred that the miRNAs comprised in the test system have nucleotide sequences according to SEQ ID NO: 1 to SEQ ID NO: 4, fragments thereof, or sequences having at least 80% sequence identity thereto. It is most preferred that the miRNAs comprised in the test system have nucleotide sequences according to (i) SEQ ID NO: 1 and SEQ ID NO: 2, fragments thereof, or sequences having at least 80% sequence identity thereto, (ii) SEQ ID NO: 1 and SEQ ID NO: 3, fragments thereof, or sequences having at least 80% sequence identity thereto, (iii) SEQ ID NO: 1 and SEQ ID NO: 4, fragments thereof, or sequences having at least 80% sequence identity thereto, (iv) SEQ ID NO: 2 and SEQ ID NO: 3, fragments thereof, or sequences having at least 80% sequence identity thereto, (v) SEQ ID NO: 2 and SEQ ID NO: 4, fragments thereof, or sequences having at least 80% sequence identity thereto, or (vi) SEQ ID NO: 3 and SEQ ID NO: 4, fragments thereof, or sequences having at least 80% sequence identity thereto. Other preferred combinations of the different miRNAs are listed in FIG. 8.

In case of the miRNA having a nucleotide sequence according to SEQ ID NO: 3, a fragment thereof, or a sequence having at least 80% sequence identity thereto, it is preferred that the level of this miRNA is only determined together with the level of at least one further miRNA having a nucleotide sequence selected from the group consisting of SEQ ID NO: 1, SEQ ID NO: 2, SEQ ID NO: 4 to SEQ ID NO: 15, a fragment thereof, and a sequence having at least 80% sequence identity thereto, particularly selected from the group consisting of SEQ ID NO: 1, SEQ ID NO: 2, SEQ ID NO: 4 to SEQ ID NO: 8, SEQ ID NO: 10 to SEQ ID NO: 15, a fragment thereof, and a sequence having at least 80% sequence identity thereto, or in case of the miRNA having a nucleotide sequence according to SEQ ID NO: 9, a fragment thereof, or a sequence having at least 80% sequence identity thereto, it is preferred that the level of this miRNA is only determined together with the level of at least one further miRNA having a nucleotide sequence selected from the group consisting of SEQ ID NO: 1 to SEQ ID NO: 8, SEQ ID NO: 10 to SEQ ID NO: 15, a fragment thereof, and a sequence having at least 80% sequence identity thereto, particularly selected from the group consisting of SEQ ID NO: 1, SEQ ID NO: 2, SEQ ID NO: 4 to SEQ ID NO: 8, SEQ ID NO: 10 to SEQ ID NO: 15, a fragment thereof, and a sequence having at least 80% sequence identity thereto. In addition, in case of miRNAs having nucleotide sequences according to SEQ ID NO: 3, SEQ ID NO: 9, a fragment thereof, or a sequence having at least 80% sequence identity thereto, it is preferred that the level of these miRNA is only determined together with the level of at least one further miRNA having a nucleotide sequence selected from the group consisting of SEQ ID NO: 1, SEQ ID NO: 2, SEQ ID NO: 4 to SEQ ID NO: 8, SEQ ID NO: 10 to SEQ ID NO: 15, a fragment thereof, and a sequence having at least 80% sequence identity thereto.

As to the definition of the terms "miRNA fragments", "miRNA variants", or "miRNA fragment variants", it is referred to the first aspect of the present invention.

Preferably, multiples sclerosis (MS) is relapsing-remitting multiple sclerosis (RR-MS), secondary progressive multiple sclerosis (SP-MS), progressive relapsing multiple sclerosis (PR-MS), or primary progressive multiple sclerosis (PP-MS). More preferably, multiples sclerosis (MS) is relapsing-remitting multiple sclerosis (RR-MS).

The patient may be any organism such as vertebrate, particularly any mammal, including both a human and another mammal, e.g. an animal such as a rodent, a rabbit, or a monkey. The rodent may be a mouse, rat, hamster, guinea pig, or chinchilla. Preferably, the patient is a human or a rodent.

It is preferred that the test system which comprises at least one miRNA, wherein the nucleotide sequence of the at least one miRNA is selected from the group consisting of SEQ ID NO: 1 to SEQ ID NO: 15, a fragment thereof, and a sequence having at least 80% sequence identity thereto is a multiple sclerosis (MS) test system, particularly RR-MS, SP-MS, PR-MS, or PP-MS test system. Said multiple sclerosis test system, particularly RR-MS, SP-MS, PR-MS, or PP-MS test system, may be characterized by a deregulation of the miRNA(s) which nucleotide sequence(s) is (are) selected from the group consisting of SEQ ID NO: 1 to SEQ ID NO: 6, SEQ ID NO: 8, SEQ ID NO: 9 to SEQ ID NO: 11, SEQ ID NO: 15, a fragment thereof, and a sequence having at least 80% sequence identity thereto compared to a healthy condition. Particularly, the level of the miRNA(s) which nucleotide sequence(s) is (are) selected from the group consisting of SEQ ID NO: 1 to SEQ ID NO: 6, SEQ ID NO: 8, a fragment thereof, and a sequence having at least 80% sequence identity thereto is decreased in MS, particularly RR-MS, compared to the level of the same miRNA in a healthy condition, while the level of the miRNA(s) which nucleotide sequence(s) is (are) selected from the group consisting of SEQ ID NO: 9 to SEQ ID NO: 11, SEQ ID NO: 15, a fragment thereof, and a sequence having at least 80% sequence identity thereto is increased in MS, particularly RR-MS, compared to the level of the same miRNA in a healthy condition.

The test system may be an in vitro test system. It is preferred that the (in vitro) test system comprises or consists of a test sample as defined herein or fractions thereof, e.g. a blood or urine sample (see first aspect of the invention). It is particularly preferred that said test system comprises or consists of cells or of a cell culture established by culturing or growing cells of a test sample as defined herein or fractions thereof, preferably under controlled conditions. In a preferred embodiment, the in vitro test system is a TruCulture Blood collection and Whole Blood Culture System (Myriad RBM). Said systems allow for blood collection, provision of nutrients for up to 48 hours incubation time and investigation of interactions of the compound with the test sample within the very same tube. Said test sample is preferably derived from a patient, e.g. a human or rodent such as a mouse or rat, suffering from multiple sclerosis, particularly RR-MS, SP-MS, PR-MS, or PP-MS.

Alternatively, the test system may be an in vivo test system. It is preferred that the (in vivo) test system comprising or consisting of an organism, preferably an organism suffering from multiple sclerosis, particularly RR-MS, SP-MS, PR-MS, or PP-MS, and more preferably a human or an animal such as a rodent, e.g. a mouse or rat, most preferably a human or an animal such as a rodent, e.g. a mouse or rat, suffering from multiple sclerosis, particularly RR-MS, SP-MS, PR-MS, or PP-MS. Model organisms for multiple sclerosis are well known in the art and include, for example, rodent, particularly mouse or rat, model systems. For example, experimental autoimmune encephalomyelitis (EAE) is an animal model for multiple sclerosis. Such an EAE model exists, for example, for rodents, e.g. mice and rats.

In case that an organism, e.g. a human or an animal such as a rodent, e.g. a mouse or rat, is used as a (in vivo) test system, it is also possible that a test sample is provided (see above), e.g. by removing body fluids, cell(s), cell colonies, an explant, or a section from said organism. For example, a tissue sample may be removed from said organism by conventional biopsy techniques or a blood sample may be taken from said organism by conventional blood collection techniques.

The term "test compound" means any compound suitable for pharmaceutical delivery. The test compound is preferably selected from the group consisting of cells, viruses, bacteria, genetically modified cells, nucleic acids (e.g. vectors comprising a transgene), proteins, peptides, hormones, antibodies, RNA, preferably siRNA or dsRNA, small molecules such as small organic or inorganic molecules, preferably about 800 Daltons more preferably about 500 Daltons, drugs, pharmaceutically active substances, metabolites, natural compounds, or samples of soil, plants or marine origin. Test compounds may be designed specifically or may be derived from libraries already available. The term "library" refers to a collection of samples. Preferably, the test compound is provided in form of a chemical compound library. Chemical compound libraries include a plurality of chemical compounds and have been assembled from any of multiple sources, including chemical synthesized molecules or natural products, or have been generated by combinatorial chemistry techniques. They are especially suitable for high-throughput screening and may be comprised of chemical compounds of a particular structure or compounds of a particular organism such as a plant. For instance, synthetic compound libraries are commercially available from Maybridge Chemical Co. (Trevillet, Cornwall, UK), ChemBridge Corporation (San Diego, Calif.), or Aldrich (Milwaukee, Wis.). A natural compound library is, for example, available from TimTec LLC (Newark, Del.). Alternatively, libraries of natural compounds in the form of bacterial, fungal, plant, and animal extracts can be used.

Test compounds to be used according to the fifth aspect of the invention may further be selected from the group consisting of natalizumab, interferon beta 1a, interferon beta 1b, glatiramer acetate, alemtuzumab, fingolimod, dimethyl fumarate, mitoxantrone or drugs known to be effective in immune or autoimmune diseases including, but not limited to, multiple sclerosis, psoriasis, rheumatoid arthritis, Crohn's disease, sarcoidosis, systemic lupus erythematosis, ulcerative colitis, Sjogren syndrome, and Type I diabetes.

The test compound may be contacted with the test system over a time period of an hour or several hours, e.g. 1, 2, 3, 4, 5, 6, 7, 8, 9, 10, 11, 12, 13, 14, 15, 16, 17, 18, 19, 20, 21, 22, 23, or 24 hours, over a time period of a day or several days, e.g. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 days, over a time period of a week or several weeks, e.g. 1, 2, 3, or 4 weeks, or over a time period of a month or several months, e.g. 1, 2, 3, 4, 5, 6, 7, 8, 9, 10, 11, or 12 months. Preferably, the test compound is contacted with the test system over a time period of between 1 day and 50 days, more preferably, between 10 or 13 days and 50 days, e.g. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 days.

The test compound may be contacted with the test system by application, e.g. cell medium supplementation, cell electroporation, or cell lipofection, or by administration, e.g. oral, nasal, rectal, parenteral, vaginal, or topical administration. For example, if the test system comprising or consisting of a test sample as defined herein or fractions thereof, e.g. a blood sample such as from a multiple sclerosis patient, or if the test system particularly comprises or consists of cells or of a cell culture established by culturing or growing cells of a test sample as defined herein or fractions thereof, e.g. a blood sample such as from a multiple sclerosis patient, the test compound may be contacted with the test system by applying the test compound to the test system. Further, for example, if the test system is a test system comprising or consisting of an organism, preferably an organism suffering from multiple sclerosis, and more preferably a human or an animal, most preferably a human or an animal suffering from multiple sclerosis, the compound may be contacted with the system by oral, nasal, rectal, parenteral, vaginal, or topical administration. Parental administration includes subcutaneous, intracutaneous, intramuscular, intravenous or intraperitoneal administration.

The determination of the effect of the test compound on the test system preferably comprises the determination of the level of the at least one miRNA, e.g. 1, 2, 3, 4, 5, 6, 7, 8, 9, 10, 11, 12, 13, 14, or 15 miRNA(s), in the test system, wherein the nucleotide sequence of the at least one miRNA is selected from the group consisting of SEQ ID NO: 1 to SEQ ID NO: 15, a fragment thereof, and a sequence having at least 80% sequence identity thereto. As to preferred miRNAs and miRNA combinations, it is referred to the above.

Preferably, the level of the at least one miRNA is the expression level. Said level of the miRNA, particularly expression level of the miRNA, may be indicated as (relative) miRNA concentration, (relative) miRNA amount, or (relative) miRNA extinction units such as relative fluorescence units. It is preferred that the level, particularly the expression level, is determined by nucleic acid hybridization, nucleic acid amplification, polymerase extension, sequencing, mass spectroscopy or any combination thereof.

More preferably, (i) the nucleic acid hybridization is performed using a microarray/biochip or beads, or using in situ hybridization, and/or (ii) the nucleic acid amplification is performed using real-time PCR.

For further information and preferred embodiments as to the determination of the level, particularly expression level, of the at least one miRNA, it is referred to the first aspect of the invention.

As mentioned above, the test compound is identified as a compound suitable for the treatment of multiple sclerosis, particularly RR-MS, SP-MS, PR-MS, or PP-MS, when a significant effect of the test compound on the test system relative to a control is detected. This significant effect preferably relies on/is based on a change of the level of the at least one miRNA, e.g. 1, 2, 3, 4, 5, 6, 7, 8, 9, 10, 11, 12, 13, 14, or 15 miRNA(s), comprised in the test system, wherein the nucleotide sequence of the at least one miRNA is selected from the group consisting of SEQ ID NO: 1 to SEQ ID NO: 15, a fragment thereof, and a sequence having at least 80% sequence identity thereto relative to a control. Said control may be a control (system) not contacted with the test compound. Preferably, the control is the same as the test system or the control system is the same as the test system but not contacted with the test compound. For example, if the test system is a blood sample from a multiple sclerosis patient, the control (system) is a blood sample from a multiple sclerosis patient but not contacted with the test compound. Further, for example, if the test system is an animal model for multiple sclerosis such as EAE, e.g. a mouse or rat EAE, the control (system) is an animal model for multiple sclerosis such as EAE, e.g. a mouse or rat EAE, but not contacted with the test compound. Instead of the test compound, the control (system) may be contracted with a placebo (compound), e.g. an aqueous solution or a salt solution such as a physiologic salt solution. It is particularly preferred that the control (system) resembles the test system in age and sex. For example, the test sample as test system and the sample as control (system) may be from age- and sex-matched patients, or the test organism as test system and the organism as control (system) may be from age- and sex-matched patients. It is also particularly preferred that the patients have undergone a wash-out period to remove any pharmaceutical substances from the body. For example, the patients that will be contacted with the test compound or the patients that will be contacted with the test compound and from which a test sample will subsequently be taken may have undergone a 3-month was-out period prior to receiving the test compound. Said control (system) comprises at least one miRNA, e.g. 1, 2, 3, 4, 5, 6, 7, 8, 9, 10, 11, 12, 13, 14, or 15 miRNA(s), wherein the nucleotide sequence of the at least one miRNA is selected from the group consisting of SEQ ID NO: 1 to SEQ ID NO: 15, a fragment thereof, and a sequence having at least 80% sequence identity thereto. The level of the at least one miRNA in the control (system) is preferably known or determinable and, thus, comparable with the level of said at least one miRNA in the test system. Said level may also be an average level of the at least one miRNA, e.g. 1, 2, 3, 4, 5, 6, 7, 8, 9, 10, 11, 12, 13, 14, or 15 miRNA(s), determined by measuring a number of controls or control systems, preferably at least two controls or control systems, more preferably at least 2 to 40 controls or control systems, even more preferably at least 10 to 60 controls or control systems, and most preferably at least 50 to 100 controls or control systems, e.g. at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 controls or control systems.

Preferably the polynucleotide (probe) according to the sixth aspect of the invention or the polynucleotide set comprising at least two different polynucleotide (probes) according to the seventh aspect of the invention is used to determine the level, particularly expression level, of the at least one miRNA in the test system or control (system), wherein the nucleotide sequence of the at least one miRNA is selected from the group consisting of SEQ ID NO: 1 to SEQ ID NO: 15, a fragment thereof, and a sequence having at least 80% sequence identity thereto.

It is preferred that the significant effect of the test compound on the test system relies on an increase of the level of the at least one miRNA, e.g. 1, 2, 3, 4, 5, 6, 7, or 8 miRNA(s), which nucleotide sequence is selected from the group consisting of SEQ ID NO: 1 to SEQ ID NO: 8, a fragment thereof, and a sequence having at least 80% sequence identity thereto, preferably SEQ ID NO: 1, SEQ ID NO: 2, SEQ ID NO: 5 to SEQ ID NO: 8, a fragment thereof, and a sequence having at least 80% sequence identity thereto, more preferably SEQ ID NO: 1, SEQ ID NO: 2, a fragment thereof, and a sequence having at least 80% sequence identity thereto, in the test system relative to a control (system), and/or relies on a decrease of the level of the at least one miRNA, e.g. 1, 2, 3, 4, 5, 6, or 7 miRNA(s), which nucleotide sequence is selected from the group consisting of SEQ ID NO: 9 to SEQ ID NO: 15, a fragment thereof, and a sequence having at least 80% sequence identity thereto, preferably SEQ ID NO: 10 to SEQ ID NO: 15, a fragment thereof, and a sequence having at least 80% sequence identity thereto, in the test system relative to a control (system). It is particularly preferred that the effect of the test compound on the test system is only significant, if the level of the at least one miRNA, e.g. 1 or 2 miRNA(s), which nucleotide sequence is selected from the group consisting of SEQ ID NO: 3, SEQ ID NO: 4, a fragment thereof, or a sequence having at least 80% sequence identity thereto in the test system is increased relative to a control (system) and when the level of the at least one miRNA, e.g. 1 or 2 miRNA(s), which nucleotide sequence is selected from the group consisting of SEQ ID NO: 1, SEQ ID NO: 2, a fragment thereof, or a sequence having at least 80% sequence identity thereto in the test system is not decreased relative to a control (system).

It is, alternatively or additionally, also particularly preferred that the effect of the test compound on the test system is only significant, if the level of the miRNA which nucleotide sequence is SEQ ID NO: 9, a fragment thereof, or a sequence having at least 80% sequence identity thereto in the test system is decreased relative to a control (system) and when the level of the at least one miRNA, e.g. 1 or 2 miRNA(s), which nucleotide sequence is selected from the group consisting of SEQ ID NO: 1, SEQ ID NO: 2, a fragment thereof, or a sequence having at least 80% sequence identity thereto in the test system is not decreased relative to a control (system).

More preferably, the significant effect of test system on the test compound relies on
(i) an at least 1.2 fold increase, preferably an at least 1.4 fold increase, of the level of the miRNA having a nucleotide sequence according to SEQ ID NO: 1, an at least 1.2 fold increase, preferably an at least 1.4 fold increase, of the level of the miRNA having a nucleotide sequence according to SEQ ID NO: 2, an at least 1.2 fold increase, preferably an at least 1.4 fold increase, of the level of the miRNA having a nucleotide sequence according to SEQ ID NO: 3, an at least 1.2 fold increase, preferably an at least 1.4 fold increase, of the level of the miRNA having a nucleotide sequence according to SEQ ID NO: 4, an at least 1.2 fold increase, preferably an at least 1.4 fold increase, of the level of the miRNA having a nucleotide sequence according to SEQ ID NO: 5, an at least 1.2 fold increase, preferably an at least 1.4 fold increase, of the level of the miRNA having a nucleotide sequence according to SEQ ID NO: 6, an at least 1.2 fold increase, preferably an at least 1.4 fold increase, of the level of the miRNA having a nucleotide sequence according to SEQ ID NO: 7, and/or an at least 1.2 fold increase, preferably an at least 1.4 fold increase, of the level of the miRNA having a nucleotide sequence according to SEQ ID NO: 8, and/or
(ii) an at least 1.2 fold decrease, preferably an at least 1.4 fold decrease, of the level of the miRNA having a nucleotide sequence according to SEQ ID NO: 9, an at least 1.2 fold decrease, preferably an at least 1.4 fold decrease, of the level of the miRNA having a nucleotide sequence according to SEQ ID NO: 10, an at least 1.2 fold decrease, preferably an at least 1.4 fold decrease, of the level of the miRNA having a nucleotide sequence according to SEQ ID NO: 11, an at least 1.2 fold decrease, preferably an at least 1.4 fold decrease, of the level of the miRNA having a nucleotide sequence according to SEQ ID NO: 12, an at least 1.2 fold decrease, preferably an at least 1.4 fold decrease, of the level of the miRNA having a nucleotide sequence according to SEQ ID NO: 13, an at least 1.2 fold decrease, preferably an at least 1.4 fold decrease, of the level of the miRNA having a nucleotide sequence according to SEQ ID NO: 14, and/or an at least 1.2 fold decrease, preferably an at least 1.4 fold decrease, of the level of the miRNA having a nucleotide sequence according to SEQ ID NO: 15.

In a preferred embodiment, the present invention relates to a method of identifying a compound suitable for the treatment of multiple sclerosis (MS), particularly relapsing-remitting multiple sclerosis (RR-MS), in a patient comprising the steps of:
(i) providing a multiple sclerosis (MS), particularly a relapsing-remitting multiple sclerosis (RR-MS), test system comprising at least one miRNA, e.g. 1, 2, 3, 4, 5, 6, 7, 8, 9, 10, 11, 12, 13, 14, or 15 miRNA(s), wherein the nucleotide sequence of the at least one miRNA is selected from the group consisting of SEQ ID NO: 1 to SEQ ID NO: 15, a fragment thereof, and a sequence having at least 80% sequence identity thereto,
(ii) contacting the multiple sclerosis (MS), particularly the relapsing-remitting multiple sclerosis (RR-MS), test system with a test compound, and
(iii) determining the effect of the test compound on the multiple sclerosis (MS), particularly relapsing-remitting multiple sclerosis (RR-MS), test system by determining the level of the at least one miRNA, e.g. 1, 2, 3, 4, 5, 6, 7, 8, 9, 10, 11, 12, 13, 14, or 15 miRNA(s),
wherein the nucleotide sequence of the at least one miRNA is selected from the group consisting of SEQ ID NO: 1 to SEQ ID NO: 15, a fragment thereof, and a sequence having at least 80% sequence identity thereto in the multiple sclerosis (MS), particularly relapsing-remitting multiple sclerosis (RR-MS), test system,
wherein the test compound is identified as a compound suitable for the treatment of multiple sclerosis (MS), particularly relapsing-remitting multiple sclerosis (RR-MS), in the patient, when the effect of the test compound on the multiple sclerosis, particularly relapsing-remitting multiple sclerosis (RR-MS), test system relies on an increase of the level of the at least one miRNA, e.g. 1, 2, 3, 4, 5, 6, 7, or 8 miRNA(s), wherein the nucleotide sequence of the at least one miRNA is selected from the group consisting of SEQ ID NO: 1 to SEQ ID NO: 8, a fragment thereof, and a sequence having at least 80% sequence identity thereto relative to a control (system) which is the same as the multiple sclerosis (MS), particularly relapsing-remitting multiple sclerosis (RR-MS), test system but not contacted with the test compound, or when the effect of the test compound on the test system relies on a decrease of the level of the at least one miRNA, e.g. 1, 2, 3, 4, 5, 6, or 7 miRNA(s), wherein the nucleotide sequence of the at least one miRNA is selected from the group consisting of SEQ ID NO: 9 to SEQ ID NO: 15, a fragment thereof, and a sequence having at least 80% sequence identity thereto relative to a control (system) which is the same as the multiple sclerosis (MS), particularly relapsing-remitting multiple sclerosis (RR-MS), test system but not contacted with the test compound.

In more preferred embodiments, the nucleotide sequence of the at least one miRNA is selected from the group consisting of SEQ ID NO: 1, SEQ ID NO: 2, SEQ ID NO: 5 to SEQ ID NO: 8, a fragment thereof, and a sequence having at least 80% sequence identity thereto, most preferably SEQ ID NO: 1, SEQ ID NO: 2, a fragment thereof, and a sequence having at least 80% sequence identity thereto, and/or the nucleotide sequence of the at least one miRNA is selected from the group consisting of SEQ ID NO: 10 to SEQ ID NO: 15, a fragment thereof, and a sequence having at least 80% sequence identity thereto.

It is particularly preferred, with respect to the above mentioned embodiments, that the effect of the test compound on the test system is only significant, if the level of the at least one miRNA, e.g. 1 or 2 miRNA(s), which nucleotide sequence is selected from the group consisting of SEQ ID NO: 3, SEQ ID NO: 4, a fragment thereof, or a sequence having at least 80% sequence identity thereto in the test system is increased relative to a control (system) and when the level of the at least one miRNA, e.g. 1 or 2 miRNA(s), which nucleotide sequence is selected from the group consisting of SEQ ID NO: 1, SEQ ID NO: 2, a fragment thereof, or a sequence having at least 80% sequence identity thereto in the test system is not decreased relative to a control (system).

It is, alternatively or additionally, also particularly preferred, with respect to the above mentioned embodiments, that the effect of the test compound on the test system is only significant, if the level of the miRNA which nucleotide sequence is SEQ ID NO: 9, a fragment thereof, or a sequence having at least 80% sequence identity thereto in the test system is decreased relative to a control (system) and when the level of the at least one miRNA, e.g. 1 or 2 miRNA(s), which nucleotide sequence is selected from the group consisting of SEQ ID NO: 1, SEQ ID NO: 2, a fragment thereof, or a sequence having at least 80% sequence identity thereto in the test system is not decreased relative to a control (system).

In a preferred embodiment, the (expression) level of the at least one miRNA is determined by determining the level of the cDNA generated/transcribed from said miRNA. Preferably, said level is determined using a real time quantitative polymerase chain reaction (RT qPCR).

In another preferred embodiment, the level of the at least one miRNA is determined after a size selection of RNA which is smaller than 1000 base pairs, preferably smaller than 500 base pairs, more preferably smaller than 100 base pairs, and most preferably smaller than 30 base pairs. In a further preferred embodiment the level of the at least one miRNA is determined from a test sample that includes means for stabilizing the RNA-fraction, especially the small RNA fraction. Preferably, the means for stabilizing the RNA fraction, especially the small RNA-fraction have been either added to the test sample during or after blood collection (e.g. by adding RNAlater, or RNAretain) or were already included in the blood collection tube (e.g PAXgene tube, PAXgene blood RNA tube, or Tempus blood RNA tube)

The above (in the context of the fifth aspect of the invention) mentioned nucleotide sequence of the miRNA is selected from the group consisting of (i) a nucleotide sequence according to SEQ ID NO: 1 to SEQ ID NO: 15, (ii) a nucleotide sequence that is a fragment of the nucleotide sequence according to (i), preferably, a nucleotide sequence that is a fragment which is between 1 and 12, more preferably between 1 and 8, and most preferably between 1 and 5 or 1 and 3, i.e. 1, 2, 3, 4, 5, 6, 7, 8, 9, 10, 11, or 12, nucleotides shorter than the nucleotide sequence according to (i), and (iii) a nucleotide sequence that has at least 80%, preferably at least 85%, more preferably at least 90%, and most preferably at least 95% or 99%, i.e. 80, 81, 82, 83, 84, 85, 86, 87, 88, 89, 90, 91, 92, 93, 94, 95, 96, 97, 98, or 99%, sequence identity to the nucleotide sequence according to (i) or nucleotide sequence fragment according to (ii).

It is particularly preferred that the nucleotide sequence as defined in (iii) has at least 80%, preferably at least 85%, more preferably at least 90%, and most preferably at least 95% or 99%, i.e. 80, 81, 82, 83, 84, 85, 86, 87, 88, 89, 90, 91, 92, 93, 94, 95, 96, 97, 98, or 99%, sequence identity over a continuous stretch of at least 10, 11, 12, 13, 14, 15, 16, 17, 18, 19, 20 or more nucleotides, preferably over the whole length, to the nucleotide sequence of the nucleotide according to (i) or nucleotide fragment according to (ii).

In addition, the nucleotide sequence as defined in (ii) (i.e. nucleotide sequence fragment) or (iii) (i.e. nucleotide sequence variant or nucleotide sequence fragment variant) is only regarded as a nucleotide sequence as defined in (ii) (i.e. nucleotide sequence fragment) or (iii) (i.e. nucleotide sequence variant or nucleotide sequence fragment variant) within the context of the present invention, if it can still be bound, hybridized, recognized, or detected by a polynucleotide (probe) of complementary sequence, e.g. a polynucleotide (probe) which is complementary to the respective nucleotide sequence as defined in (i), through one or more types of chemical bonds, usually through complementary base pairing, usually through hydrogen bond formation under stringent hybridization conditions. The skilled person can readily assess whether a nucleotide sequence as defined in (ii) (i.e. nucleotide sequence fragment) or (iii) (i.e. nucleotide sequence variant or nucleotide sequence fragment variant) can still be bound, hybridized, recognized, or detected by a polynucleotide (probe) of complementary sequence, e.g. a polynucleotide (probe) which is complementary to the respective nucleotide sequence as defined in (i). Suitable assays to determine whether hybridization under stringent conditions still occurs are well known in the art. However, as an example, a suitable assay to determine whether hybridization still occurs comprises the steps of: (a) incubating a nucleotide sequence as defined in (ii) or (iii) labelled with biotin with a polynucleotide (probe) of complementary sequence, e.g. a polynucleotide (probe) which is complementary to the respective nucleotide sequence as defined in (i), wherein the polynucleotide (probe) is attached onto a biochip, under stringent hybridization conditions, (b) washing the biochip to remove unspecific bindings, (c) subjecting the biochip to a detection system, and (c) analyzing whether the nucleotide sequence can still be hybridized or detected by a polynucleotide (probe) of complementary sequence, e.g. a polynucleotide (probe) which is complementary to the respective nucleotide sequence as defined in (i). As a positive control, the respective miRNA as defined in (i) may be used. Preferably stringent hybridization conditions include the following: 50% formamide, 5×SSC, and 1% SDS, incubating at 42° C., or, 5×SSC, 1% SDS, incubating at 65° C., with wash in 0.2×SSC, and 0.1% SDS at 65° C.; or 6×SSPE, 10% formamide, 0.01%, Tween 20, 0.1×TE buffer, 0.5 mg/ml BSA, 0.1 mg/ml herring sperm DNA, incubating at 42° C. with wash in 0.5×SSPE and 6×SSPE at 45° C.

In a further aspect, the invention relates to a compound obtainable by the method according to the fifth aspect. Said compound is preferably comprised in a pharmaceutical composition.

In another further aspect, the invention relates to a compound obtainable by the method according to the fifth aspect for use in the treatment of multiple sclerosis (MS), particularly RR-MS, SP-MS, PR-MS, or PP-MS, more particularly RR-MS. Said compound is preferably comprised in a pharmaceutical composition.

In a sixth aspect, the invention relates to the use of a polynucleotide (probe) for detecting a miRNA to determine whether a patient responds to a therapeutic treatment of multiple sclerosis, to monitor the course of multiple sclerosis in a patient, to determine the risk of a relapse of multiple sclerosis in a patient, to adjust the dose of a therapeutic drug applied for therapeutic treatment of multiple sclerosis in a patient, or to identify a compound suitable for the treatment of multiple sclerosis in a patient, wherein the nucleotide sequence of the miRNA is selected from the group consisting of SEQ ID NO: 1 to SEQ ID NO: 15.

Preferably, the polynucleotide (probe) is used for detecting a miRNA, wherein the nucleotide sequence of the miRNA is selected from the group consisting of SEQ ID NO: 1 to SEQ ID NO: 4 and SEQ ID NO: 5. More preferably, the polynucleotide (probe) is used for detecting a miRNA, wherein the nucleotide sequence of the miRNA is selected from the group consisting of SEQ ID NO: 1 and SEQ ID NO: 2.

In an alternative embodiment, the miRNA is not a miRNA having the nucleotide sequence according to SEQ ID NO: 3 or SEQ ID NO: 9.

As mentioned above, the polynucleotide (probe) is used to monitor the course of multiple sclerosis in a patient.

It is preferred that the polynucleotide (probe) is used to detect a miRNA for determining whether the patient benefits from a therapeutic treatment of multiple sclerosis. Said patient preferably receives or has received a therapeutic treatment of multiple sclerosis. It is also preferred that the polynucleotide (probe) is used to detect a miRNA for determining whether the multiple sclerosis (MS) in the patient improves, exacerbates or is stable. It is alternatively preferred that the polynucleotide (probe) is used to detect a miRNA for determining whether multiple sclerosis in the patient further improves, again exacerbates or is stable, wherein the patient preferably receives or has received a successful therapeutic treatment of multiple sclerosis.

Preferably, the polynucleotide (probe) used is useful for detecting a miRNA to determine whether a patient responds to a therapeutic treatment of multiple sclerosis, to monitor the course of multiple sclerosis in a patient, to determine the risk of a relapse of multiple sclerosis in a patient, to adjust the dose of a therapeutic drug applied for therapeutic treatment of multiple sclerosis in a patient, or to identify a compound suitable for the treatment of multiple sclerosis in a patient, wherein the nucleotide sequence of the miRNA is selected from the group consisting of SEQ ID NO: 1 to SEQ ID NO: 15.

Preferably, the polynucleotide (probe) used is useful for detecting a miRNA, wherein the nucleotide sequence of the miRNA is selected from the group consisting of SEQ ID NO: 1 to SEQ ID NO: 4 and SEQ ID NO: 5. More preferably, the polynucleotide (probe) used is useful for detecting a miRNA, wherein the nucleotide sequence of the miRNA is selected from the group consisting of SEQ ID NO: 1 and SEQ ID NO: 2.

In an alternative embodiment, the miRNA is not a miRNA having the nucleotide sequence according to SEQ ID NO: 3 or SEQ ID NO: 9.

It is also preferred that (i) the (above mentioned) polynucleotide (probe) is complementary to the miRNA, wherein the nucleotide sequence of the miRNA is selected from the group consisting of SEQ ID NO: 1 to SEQ ID NO: 15, preferably selected from the group consisting of SEQ ID NO: 1 to SEQ ID NO: 4 and SEQ ID NO: 9, and more preferably selected from the group consisting of SEQ ID NO: 1 and SEQ ID NO: 2, (ii) the (above mentioned) polynucleotide (probe) is a fragment of the polynucleotide according to (i), preferably the polynucleotide is a fragment which is between 1 and 12, more preferably between 1 and 8, and most preferably between 1 and 5 or between 1 and 3, e.g. 1, 2, 3, 4, 5, 6, 7, 8, 9, 10, 11, or 12, nucleotides shorter than the polynucleotide according to (i), or (iii) the (above mentioned) polynucleotide (probe) has at least 80%, preferably at least 85%, more preferably at least 90%, and most preferably at least 95% or 99%, e.g. 80, 81, 82, 83, 84, 85, 86, 87, 88, 89, 90, 91, 92, 93, 94, 95, 96, 97, 98, or 99%, sequence identity to the polynucleotide sequence of the polynucleotide according to (i) or polynucleotide fragment according to (ii).

It is particularly preferred that the polynucleotide as defined in (iii) has at least 80%, preferably at least 85%, more preferably at least 90%, and most preferably at least 95% or 99%, e.g. 80, 81, 82, 83, 84, 85, 86, 87, 88, 89, 90, 91, 92, 93, 94, 95, 96, 97, 98, or 99%, sequence identity over a continuous stretch of at least 10, 11, 12, 13, 14, 15, 16, 17, 18, 19, 20 or more nucleotides, preferably over the whole length, to the polynucleotide sequence of the polynucleotide according to (i) or polynucleotide fragment according to (ii).

In addition, the polynucleotide as defined in (ii) (i.e. polynucleotide fragment) or (iii) (i.e. polynucleotide variant or polynucleotide fragment variant) is only regarded as a polynucleotide as defined in (ii) (i.e. polynucleotide fragment) or (iii) (i.e. polynucleotide variant or polynucleotide fragment variant) within the context of the present invention, if it is still capable of binding to, hybridizing with, or detecting a target miRNA of complementary sequence, e.g. the respective target miRNA according to SEQ ID NO: 1 to SEQ ID NO: 15, through one or more types of chemical bonds, usually through complementary base pairing, usually through hydrogen bond formation under stringent hybridization conditions. The skilled person can readily assess whether a polynucleotide as defined in (ii) (i.e. polynucleotide fragment) or (iii) (i.e. polynucleotide variant or polynucleotide fragment variant) is still capable of binding to, hybridizing with, recognizing or detecting a target miRNA of complementary sequence, e.g. the respective target miRNA according to SEQ ID NO: 1 to SEQ ID NO: 15. Suitable assays to determine whether hybridization under stringent conditions still occurs are well known in the art. However, as an example, a suitable assay to determine whether hybridization still occurs comprises the steps of: (a) incubating the polynucleotide as defined in (ii) or (iii) attached onto a biochip with the miRNA of complementary sequence, e.g. the respective target miRNA according to SEQ ID NO: 1 to SEQ ID NO: 15, labeled with biotin under stringent hybridization conditions, (b) washing the biochip to remove unspecific bindings, (c) subjecting the biochip to a detection system, and (c) analyzing whether the polynucleotide can still hybridize with the target miRNA of complementary sequence, e.g. the respective target miRNA according to SEQ ID NO: 1 to SEQ ID NO: 15. As a positive control, the respective non-mutated and not fragmented polynucleotide as defined in (i) may be used. Preferably stringent hybridization conditions include the following: 50% formamide, 5×SSC, and 1% SDS, incubating at 42° C., or, 5×SSC, 1% SDS, incubating at 65° C., with wash in 0.2×SSC, and 0.1% SDS at 65° C.; or 6×SSPE, 10% formamide, 0.01%, Tween 20, 0.1×TE buffer, 0.5 mg/ml BSA, 0.1 mg/ml herring sperm DNA, incubating at 42° C. with wash in 0.5×SSPE and 6×SSPE at 45° C.

It is further preferred that the determination, monitoring, adjustment, or identification is carried out on the basis of a test sample isolated from a patient. Thus, the determination, monitoring, adjustment, or identification is carried out in vitro.

As to the term "test sample" and to the preferred embodiments of the "test sample", it is referred to the first aspect of the present invention.

The patient may be any mammal, including both a human and another mammal, e.g. an animal such as a rodent, a rabbit, or a monkey. The rodent may be a mouse, rat, hamster, guinea pig, or chinchilla. Preferably, the patient is a human or a rodent.

Preferably, multiples sclerosis (MS) is relapsing-remitting multiple sclerosis (RR-MS), secondary progressive multiple sclerosis (SPMS), progressive relapsing multiple sclerosis (PRMS), or primary progressive multiple sclerosis (PPMS). More preferably, multiples sclerosis (MS) is relapsing-remitting multiple sclerosis (RR-MS).

The polynucleotide (probe) used may be comprised on a solid support, substrate, surface, platform or matrix. Preferably, the polynucleotide (probe) used is part of a biochip/microarray. Said polynucleotide (probe) used may be attached or linked to the solid support, substrate, surface, platform or matrix. Preferably, the polynucleotide (probe) used is attached or linked to the solid phase of a biochip/microarray.

The terms "biochip" or "microarray", as used herein, refer to a solid phase comprising an attached or immobilized polynucleotide described herein as probe. The polynucleotide probe may be capable of hybridizing to a target sequence, such as a complementary miRNA or miRNA* sequence, under stringent hybridization conditions. The polynucleotide probe may be attached or immobilized at a spatially defined location on the solid phase. The polynucleotide probe may either be synthesized first, with subsequent attachment to the biochip, or may be directly synthesized on the biochip. The solid phase may be a material that may be modified to contain discrete individual sites appropriate for the attachment or association of the polynucleotide probe and is amenable to at least one detection method. Representative examples of solid phase materials include glass and modified or functionalized glass, plastics (including acrylics, polystyrene and copolymers of styrene and other materials, polypropylene, polyethylene, polybutylene, polyurethanes, Teflon, etc.), polysaccharides, nylon or nitrocellulose, resins, silica or silica-based materials including silicon and modified silicon, carbon, metals, inorganic glasses and plastics. The solid phase may allow optical detection without appreciably fluorescing. The solid phase may be planar, although other configurations of solid phase may be used as well. For example, the polynucleotide probe may be placed on the inside surface of a tube, for flow-through sample analysis to minimize sample volume. Similarly, the solid phase may be flexible, such as flexible foam, including closed cell foams made of particular plastics. The solid phase of the biochip and the probe may be modified with chemical functional groups for subsequent attachment of the two. For example, the biochip may be modified with a chemical functional group including, but not limited to, amino groups, carboxyl groups, oxo groups or thiol groups. One or more functional groups may be attached on the probe either directly or indirectly using a linker. The polynucleotide probe may be attached to the solid support by either the 5' terminus, 3' terminus, or via an internal nucleotide. The polynucleotide probe may also be attached to the solid support non-covalently. For example, a biotinylated polynucleotide can be made, which may bind to surfaces covalently coated with streptavidin, resulting in attachment. Alternatively, a polynucleotide probe may be synthesized on the surface using techniques such as photopolymerization and photolithography. In preferred embodiments, more than one probe is attached or linked to the solid support of the biochip/microarray. In the context of the present invention, the terms "biochip" and "microarray" are interchangeable used.

The terms "attached", "linked", or "immobilized", as used herein, refer to the binding between the polynucleotide and the solid support/phase and may mean that the binding between the polynucleotide probe and the solid support is sufficient to be stable under conditions of binding, washing, analysis and removal. The binding may be covalent or non-covalent. Covalent bonds may be formed directly between the polynucleotide and the solid support or may be formed by a cross linker or by inclusion of specific reactive groups on either the solid support or the polynucleotide, or both. Non-covalent binding may be electrostatic, hydrophilic and hydrophobic interactions or combinations thereof. Immobilization or attachment may also involve a combination of covalent and non-covalent interactions.

Alternatively, the polynucleotide (probe) used may be comprised on beads or microspheres. Preferably, the polynucleotide used is attached to or immobilized on the beads or microspheres, e.g. via a covalent or non-covalent linkage (see above). Preferably, said beads or microspheres are made of a synthetic material, e.g. polystyrene, polyethylene or polypropylene. It is preferred that said beads or microspheres have a mean diameter of between 2 to 20 microns, preferably 4 to 10 microns, most preferably 5 to 7 microns, e.g. 2, 3, 4, 5, 6, 7, 8, 9, 10, 11, 12, 13, 14, 15, 16, 17, 18, 19, or 20 microns. It is also preferred that said beads or microspheres are internally dyed, preferably with red and infrared fluorophores. For example, the bead or microsphere setting from Luminex may be used.

The polynucleotide (probe) may also be comprised as polynucleotide fragment, polynucleotide variant, or polynucleotide fragment variant on a solid support, substrate, surface, platform, matrix, particularly biochip/microarray, beads or microspheres.

In a seventh aspect, the invention relates to the use of a polynucleotide set comprising, essentially consisting of, or consisting of at least two different polynucleotides (probes), e.g. 2, 3, 4, 5, 6, 7, 8, 9, 10, 11, 12, 13, 14, or 15 polynucleotides (probes), according to the sixth aspect for detecting at least two different miRNAs, e.g. 2, 3, 4, 5, 6, 7, 8, 9, 10, 11, 12, 13, 14, or 15 miRNAs, to determine whether a patient responds to a therapeutic treatment of multiple sclerosis, to monitor the course of multiple sclerosis in a patient, to determine the risk of a relapse of multiple sclerosis in a patient, to adjust the dose of a therapeutic drug applied for therapeutic treatment of multiple sclerosis in a patient, or to identify a compound suitable for the treatment of multiple sclerosis in a patient.

It is preferred that the nucleotide sequences of the different miRNAs have SEQ ID NO: 1 to SEQ ID NO: 15. It is particularly preferred that the nucleotide sequences of the different miRNAs have SEQ ID NO: 1 to SEQ ID NO: 8 or SEQ ID NO: 9 to SEQ ID NO: 15. It is more preferred that the nucleotide sequences of the different miRNAs have SEQ ID NO: 1 to SEQ ID NO: 4 and SEQ ID NO: 9. It is particularly more preferred that the nucleotide sequences of the different miRNAs have SEQ ID NO: 1 to SEQ ID NO: 4. It is most preferred that the nucleotide sequences of the different miRNAs have SEQ ID NO: 1 and SEQ ID NO: 2, SEQ ID NO: 1 and SEQ ID NO: 3, SEQ ID NO: 1 and SEQ ID NO: 4, SEQ ID NO: 2 and SEQ ID NO: 3, SEQ ID NO: 2 and SEQ ID NO: 4, or SEQ ID NO: 3 and SEQ ID NO: 4. Other preferred combinations of the different miRNAs are listed in FIG. 8.

In case of the miRNA having a nucleotide sequence according to SEQ ID NO: 3, a fragment thereof, or a sequence having at least 80% sequence identity thereto, it is preferred that this miRNA is used together with at least one further miRNA having a nucleotide sequence selected from the group consisting of SEQ ID NO: 1, SEQ ID NO: 2, SEQ ID NO: 4 to SEQ ID NO: 15, a fragment thereof, and a sequence having at least 80% sequence identity thereto, particularly selected from the group consisting of SEQ ID NO: 1, SEQ ID NO: 2, SEQ ID NO: 4 to SEQ ID NO: 8, SEQ ID NO: 10 to SEQ ID NO: 15, a fragment thereof, and a sequence having at least 80% sequence identity thereto, or in case of the miRNA having a nucleotide sequence according to SEQ ID NO: 9, a fragment thereof, or a sequence having at least 80% sequence identity thereto, it is preferred that this miRNA is used together with at least one further miRNA having a nucleotide sequence selected from the group consisting of SEQ ID NO: 1 to SEQ ID NO: 8, SEQ ID NO: 10 to SEQ ID NO: 15, a fragment thereof, and a sequence having at least 80% sequence identity thereto, particularly selected from the group consisting of SEQ ID NO: 1, SEQ ID NO: 2, SEQ ID NO: 4 to SEQ ID NO: 8, SEQ ID NO: 10 to SEQ ID NO: 15, a fragment thereof, and a sequence having at least 80% sequence identity thereto. In addition, in case of miRNAs having nucleotide sequences according to SEQ ID NO: 3, SEQ ID NO: 9, a fragment thereof, or a sequence having at least 80% sequence identity thereto, it is preferred that these miRNA are used together with at least one further miRNA having a nucleotide sequence selected from the group consisting of SEQ ID NO: 1, SEQ ID NO: 2, SEQ ID NO: 4 to SEQ ID NO: 8, SEQ ID NO: 10 to SEQ ID NO: 15, a fragment thereof, and a sequence having at least 80% sequence identity thereto.

The at least two different polynucleotides (probes) of the polynucleotide set used may be comprised on a solid support, substrate, surface, platform or matrix. Preferably, the at least two different polynucleotides (probes) of the polynucleotide set used are part of a biochip/microarray. Said at least two different polynucleotides (probes) of the polynucleotide set used may be attached or linked to the solid support, substrate, surface, platform or matrix. Preferably, the at least two different polynucleotides (probes) of the polynucleotide set used are attached or linked to the solid phase of a biochip/microarray. The same applies for the polynucleotide fragments, polynucleotide variants, or polynucleotide fragment variants (probe) mentioned above.

As to the definition of the terms "biochip", "microarray", "attached", "linked", or "immobilized", it is referred to the sixth aspect of the invention.

Alternatively, the at least two different polynucleotides (probes) of the polynucleotide set used may be comprised on beads or microspheres. Preferably, the at least two different polynucleotides (probes) of the polynucleotide set used are attached to or immobilized on the beads or microspheres, e.g. via a covalent or non-covalent linkage (see above). Preferably, said beads or microspheres are made of a synthetic material, e.g. polystyrene, polyethylene or polypropylene. It is preferred that said beads or microspheres have a mean diameter of between 2 to 20 microns, preferably 4 to 10 microns, most preferably 5 to 7 microns, e.g. 2, 3, 4, 5, 6, 7, 8, 9, 10, 11, 12, 13, 14, 15, 16, 17, 18, 19, or 20 microns. It is also preferred that said beads or microspheres are internally dyed, preferably with red and infrared fluorophores. For example, the bead or microsphere setting from Luminex may be used.

The polynucleotide (probe) may also be comprised as polynucleotide fragment, polynucleotide variant, or polynucleotide fragment variant on a solid support, substrate, surface, platform, matrix, particularly biochip/microarray, beads or microspheres.

It is preferred that the polynucleotide (probe) according to the sixth aspect of the invention or the polynucleotide set comprising at least two different polynucleotide (probes) according to the seventh aspect of the invention is used in the methods according to the first to fourth aspect of the invention for determining the level, particularly expression level, of at least one miRNA in a test sample isolated from the patient, wherein the nucleotide sequence of the at least one miRNA is selected from the group consisting of SEQ ID NO: 1 to SEQ ID NO: 15, a fragment thereof, and a sequence having at least 80% sequence identity thereto.

In an eighth aspect, the invention relates to a kit for determining whether a patient responds to a therapeutic treatment of multiple sclerosis, for monitoring the course of multiple sclerosis in a patient, for determining the risk of a relapse of multiple sclerosis in a patient, for adjusting the dose of a therapeutic drug applied for therapeutic treatment of multiple sclerosis in a patient, or for identifying a compound suitable for the treatment of multiple sclerosis in a patient comprising means for determining the level, particularly expression level, of at least one miRNA, e.g. 1, 2, 3, 4, 5, 6, 7, 8, 9, 10, 11, 12, 13, 14, or 15 miRNA(s), in a test sample isolated from a patient, wherein the nucleotide sequence of the at least one miRNA is selected from the group consisting of SEQ ID NO: 1 to SEQ ID NO: 15, a fragment thereof, and a sequence having at least 80% sequence identity thereto.

In the context of the present invention, the term "kit of parts (in short: kit)", as used herein, is understood to be any combination of at least some of the components identified herein, and which are combined, coexisting spatially, to a functional unit, and which can contain further components.

The patient may be any mammal, including both a human and another mammal, e.g. an animal such as a rodent, a rabbit, or a monkey. The rodent may be a mouse, rat, hamster, guinea pig, or chinchilla. Preferably, the patient is a human or a rodent.

Preferably, multiples sclerosis (MS) is relapsing-remitting multiple sclerosis (RR-MS), secondary progressive multiple sclerosis (SPMS), progressive relapsing multiple sclerosis (PRMS), or primary progressive multiple sclerosis (PPMS). More preferably, multiples sclerosis (MS) is relapsing-remitting multiple sclerosis (RR-MS).

As to the term "test sample" and to the preferred embodiments of the "test sample", it is referred to the first aspect of the invention (see above).

It is preferred that said means for determining the level, particularly expression level, of at least one miRNA, e.g. 1, 2, 3, 4, 5, 6, 7, 8, 9, 10, 11, 12, 13, 14, or 15 miRNA(s), as mentioned above in a test sample isolated from a patient is a polynucleotide (probe) according to the sixth aspect of the invention or a polynucleotide set comprising, essentially consisting of, or consisting of at least two different polynucleotides (probes) according to the seventh aspect of the invention. It is also preferred that said means for determining the level, particularly expression level, of at least one miRNA, e.g. 1, 2, 3, 4, 5, 6, 7, 8, 9, 10, 11, 12, 13, 14, or 15 miRNA(s), as mentioned above in a test sample isolated from a patient is a solid support, substrate, surface, platform, or matrix comprising a polynucleotide (probe) according to the sixth aspect of the invention or a polynucleotide set comprising, essentially consisting of, or consisting of at least two different polynucleotides (probes) according to the seventh aspect of the invention. It is more preferred that said means for determining the level, particularly expression level, of at least one miRNA, e.g. 1, 2, 3, 4, 5, 6, 7, 8, 9, 10, 11, 12, 13, 14, or 15 miRNA(s), as mentioned above in a test sample isolated from a patient is a microarray/biochip, are beads, or microspheres comprising, essentially consisting of, or consisting of a polynucleotide (probe) according to the sixth aspect of the invention or a polynucleotide set comprising at least two different polynucleotides (probes) according to the seventh aspect of the invention. Most preferably, the polynucleotide(s) (probe(s)) is (are) attached to, linked to, or immobilized on the solid phase of a biochip/microarray, or beads or microspheres.

The polynucleotide (probe) may also be comprised as polynucleotide fragment, polynucleotide variant, or polynucleotide fragment variant on a solid support, substrate, surface, platform, matrix, particularly biochip/microarray, beads or microspheres.

As to the definition of the terms "polynucleotide fragment", "polynucleotide variant", or "polynucleotide fragment variant", it is referred to the sixth aspect of the invention.

In addition, as to the definition of the terms "biochip", "microarray", "beads", "microspheres", "attached", "linked", or "immobilized", it is referred to the sixth aspect of the invention.

Furthermore, said means for determining the level of at least one miRNA, e.g. 1, 2, 3, 4, 5, 6, 7, 8, 9, 10, 11, 12, 13, 14, or 15 miRNA(s), as mentioned above in a test sample isolated from a patient, may be primers suitable to perform reverse transcriptase reaction, primers suitable to perform real time polymerase chain reaction (RT-PCR) such as real time quantitative polymerase chain reaction (RT-qPCR), and/or means for conducting next generation sequencing.

It is preferred that the level, particularly expression level, of the nucleotide sequence of the miRNA having SEQ ID NO: 1, SEQ ID NO: 2, SEQ ID NO: 3, SEQ ID NO: 4, SEQ ID NO: 9, a fragment thereof, or a sequence having at least 80% sequence identity thereto is determined. It is particularly preferred that the level, particularly expression level, of the nucleotide sequence of the miRNA having SEQ ID NO: 1, SEQ ID NO: 2, a fragment thereof, or a sequence having at least 80% sequence identity thereto is determined.

In an alternative embodiment, the level, particularly expression level, of the nucleotide sequence of the miRNA having SEQ ID NO: 3, a fragment thereof, or a sequence having at least 80% sequence identity thereto is not determined, and/or the level, particularly expression level, of the nucleotide sequence of the miRNA having SEQ ID NO: 9, a fragment thereof, or a sequence having at least 80% sequence identity thereto is not determined.

It is further preferred that the level, particularly expression level, of the nucleotide sequences of the miRNAs having SEQ ID NO: 1 to SEQ ID NO: 15, fragments thereof, or sequences having at least 80% sequence identity thereto is determined. It is particularly preferred that the level, particularly expression level, of the nucleotide sequences of the miRNAs having SEQ ID NO: 1 to SEQ ID NO: 8, fragments thereof, or sequences having at least 80% sequence identity thereto is determined, or that the level, particularly expression level, of the nucleotide sequences of the miRNAs having SEQ ID NO: 9 to SEQ ID NO: 15, fragments thereof, or sequences having at least 80% sequence identity thereto is determined. It is more preferred that the level, particularly expression level, of the nucleotide sequences of the miRNAs having SEQ ID NO: 1 to SEQ ID NO: 4 and SEQ ID NO: 9, fragments thereof, or sequences having at least 80% sequence identity thereto is determined. It is particularly more preferred that the level, particularly expression level, of the nucleotide sequences of the miRNAs having SEQ ID NO: 1 to SEQ ID NO: 4, fragments thereof, or sequences having at least 80% sequence identity thereto is determined. It is most preferred that the level, particularly expression level, of the nucleotide sequences of the miRNAs having (i) SEQ ID NO: 1 and SEQ ID NO: 2, fragments thereof, or sequences having at least 80% sequence identity thereto, (ii) SEQ ID NO: 1 and SEQ ID NO: 3, fragments thereof, or sequences having at least 80% sequence identity thereto, (iii) SEQ ID NO: 1 and SEQ ID NO: 4, fragments thereof, or sequences having at least 80% sequence identity thereto, (iv) SEQ ID NO: 2 and SEQ ID NO: 3, fragments thereof, or sequences having at least 80% sequence identity thereto, (v) SEQ ID NO: 2 and SEQ ID NO: 4, fragments thereof, or sequences having at least 80% sequence identity thereto, or (vi) SEQ ID NO: 3 and SEQ ID NO: 4, fragments thereof, or sequences having at least 80% sequence identity thereto is determined.

In case of the miRNA having a nucleotide sequence according to SEQ ID NO: 3, a fragment thereof, or a sequence having at least 80% sequence identity thereto, it is preferred that the level of this miRNA is only determined together with the level of at least one further miRNA having a nucleotide sequence selected from the group consisting of SEQ ID NO: 1, SEQ ID NO: 2, SEQ ID NO: 4 to SEQ ID NO: 15, a fragment thereof, and a sequence having at least 80% sequence identity thereto, particularly selected from the group consisting of SEQ ID NO: 1, SEQ ID NO: 2, SEQ ID NO: 4 to SEQ ID NO: 8, SEQ ID NO: 10 to SEQ ID NO: 15, a fragment thereof, and a sequence having at least 80% sequence identity thereto, or in case of the miRNA having a nucleotide sequence according to SEQ ID NO: 9, a fragment thereof, or a sequence having at least 80% sequence identity thereto, it is preferred that the level of this miRNA is only determined together with the level of at least one further miRNA having a nucleotide sequence selected from the group consisting of SEQ ID NO: 1 to SEQ ID NO: 8, SEQ ID NO: 10 to SEQ ID NO: 15, a fragment thereof, and a sequence having at least 80% sequence identity thereto, particularly selected from the group consisting of SEQ ID NO: 1, SEQ ID NO: 2, SEQ ID NO: 4 to SEQ ID NO: 8, SEQ ID NO: 10 to SEQ ID NO: 15, a fragment thereof, and a sequence having at least 80% sequence identity thereto. In addition, in case of miRNAs having nucleotide sequences according to SEQ ID NO: 3, SEQ ID NO: 9, a fragment thereof, or a sequence having at least 80% sequence identity thereto, it is preferred that the level of these miRNA is only determined together with the level of at least one further miRNA having a nucleotide sequence selected from the group consisting of SEQ ID NO: 1, SEQ ID NO: 2, SEQ ID NO: 4 to SEQ ID NO: 8, SEQ ID NO: 10 to SEQ ID NO: 15, a fragment thereof, and a sequence having at least 80% sequence identity thereto. Other preferred miRNA combinations are listed in FIG. 8.

The above (in the context of the eight aspect of the invention) mentioned nucleotide sequence of the miRNA is selected from the group consisting of
(i) a nucleotide sequence according to SEQ ID NO: 1 to SEQ ID NO: 15,
(ii) a nucleotide sequence that is a fragment of the nucleotide sequence according to (i), preferably, a nucleotide sequence that is a fragment which is between 1 and 12, more preferably between 1 and 8, and most preferably between 1 and 5 or 1 and 3, i.e. 1, 2, 3, 4, 5, 6, 7, 8, 9, 10, 11, or 12, nucleotides shorter than the nucleotide sequence according to (i), and
(iii) a nucleotide sequence that has at least 80%, preferably at least 85%, more preferably at least 90%, and most preferably at least 95% or 99%, i.e. 80, 81, 82, 83, 84, 85, 86, 87, 88, 89, 90, 91, 92, 93, 94, 95, 96, 97, 98, or 99%, sequence identity to the nucleotide sequence according to (i) or nucleotide sequence fragment according to (ii).

It is particularly preferred that the nucleotide sequence as defined in (iii) has at least 80%, preferably at least 85%, more preferably at least 90%, and most preferably at least 95% or 99%, i.e. 80, 81, 82, 83, 84, 85, 86, 87, 88, 89, 90, 91, 92, 93, 94, 95, 96, 97, 98, or 99%, sequence identity over a continuous stretch of at least 10, 11, 12, 13, 14, 15, 16, 17, 18, 19, 20 or more nucleotides, preferably over the whole length, to the nucleotide sequence of the nucleotide according to (i) or nucleotide fragment according to (ii).

In addition, the nucleotide sequence as defined in (ii) (i.e. nucleotide sequence fragment) or (iii) (i.e. nucleotide sequence variant or nucleotide sequence fragment variant) is only regarded as a nucleotide sequence as defined in (ii) (i.e. nucleotide sequence fragment) or (iii) (i.e. nucleotide sequence variant or nucleotide sequence fragment variant) within the context of the present invention, if it can still be bound, hybridized, recognized, or detected by a polynucleotide (probe) of complementary sequence, e.g. a polynucleotide (probe) which is complementary to the respective nucleotide sequence as defined in (i), through one or more types of chemical bonds, usually through complementary base pairing, usually through hydrogen bond formation under stringent hybridization conditions. The skilled person can readily assess whether a nucleotide sequence as defined in (ii) (i.e. nucleotide sequence fragment) or (iii) (i.e. nucleotide sequence variant or nucleotide sequence fragment variant) can still be bound, hybridized, recognized, or detected by a polynucleotide (probe) of complementary sequence, e.g. a polynucleotide (probe) which is complementary to the respective nucleotide sequence as defined in (i). Suitable assays to determine whether hybridization under stringent conditions still occurs are well known in the art. However, as an example, a suitable assay to determine whether hybridization still occurs comprises the steps of: (a) incubating a nucleotide sequence as defined in (ii) or (iii) labelled with biotin with a polynucleotide (probe) of complementary sequence, e.g. a polynucleotide (probe) which is complementary to the respective nucleotide sequence as defined in (i), wherein the polynucleotide (probe) is attached onto a biochip, under stringent hybridization conditions, (b) washing the biochip to remove unspecific bindings, (c) subjecting the biochip to a detection system, and (c) analyzing whether the nucleotide sequence can still be hybridized or detected by a polynucleotide (probe) of complementary sequence, e.g. a polynucleotide (probe) which is complementary to the respective nucleotide sequence as defined in (i). As a positive control, the respective miRNA as defined in (i) may be used. Preferably stringent hybridization conditions include the following: 50% formamide, 5×SSC, and 1% SDS, incubating at 42° C., or, 5×SSC, 1% SDS, incubating at 65° C., with wash in 0.2×SSC, and 0.1% SDS at 65° C.; or 6×SSPE, 10% formamide, 0.01%, Tween 20, 0.1×TE buffer, 0.5 mg/ml BSA, 0.1 mg/ml herring sperm DNA, incubating at 42° C. with wash in 0.5×SSPE and 6×SSPE at 45° C.

Said kit may further comprise means for collecting the test sample and/or means for stabilizing the RNA-fraction, especially the small RNA-fraction. Preferably, the means for collecting the test sample may be a test sample collection container, more preferably a blood collection tube, most preferably a blood collection tube suitable for analysing the RNA-fraction. Preferably, the means for stabilizing the RNA fraction, especially the small RNA-fraction may either added to the test sample during or after blood collection (e.g. by adding RNAlater, or RNAretain) or are already included in the blood collection tube (e.g PAXgene tube, PAXgene blood RNA tube, or Tempus blood RNA tube). Most preferably, the means for collecting the test sample and the means for stabilizing the RNA-fraction, especially the small RNA-fraction, are comprised in a blood collection tube that contains means for stabilizing the said RNA-fraction, especially said small RNA-fraction (e.g. PAXgene blood RNA tube, or Tempus blood RNA tube).

Said kit may further comprise (i) a container, and/or (ii) a data carrier. Said data carrier may be a non-electronical data carrier, e.g. a graphical data carrier such as an information leaflet, an information sheet, a bar code or an access code, or an electronical data carrier such as a floppy disk, a compact disk (CD), a digital versatile disk (DVD), a microchip or another semiconductor-based electronical data carrier. The access code may allow the access to a database, e.g. an internet database, a centralized, or a decentralized database.

Additionally or alternatively, said kit may comprise materials desirable from a commercial and user standpoint including a buffer(s), a reagent(s) and/or a diluent(s) for determining the level of at least one miRNA, e.g. 1, 2, 3, 4, 5, 6, 7, 8, 9, 10, 11, 12, 13, 14, or 15 miRNA(s), as mentioned above in a test sample isolated from a patient. This includes reporter-means such as a labeled reporter polynucleotide.

The above mentioned data carrier may comprise a reference level of the at least one miRNA, e.g. 1, 2, 3, 4, 5, 6, 7, 8, 9, 10, 11, 12, 13, 14, or 15 miRNA(s). In the case of an access code which allows the access to a database, e.g. an internet database, a centralized, or a decentralized database, said reference level is deposited in this database.

The reference level is preferably the reference level of the same miRNA(s) which level has (have) to be determined in the test sample of the patient. The presence of the reference level permits the comparison of the level of the test sample with said reference level. This comparison finally allows to determine whether a patient responds to a therapeutic treatment of multiple sclerosis, to monitor the course of multiple sclerosis in a patient, to determine the risk of a relapse of multiple sclerosis in a patient, to adjust the dose of a therapeutic drug applied for therapeutic treatment of multiple sclerosis in a patient, or to identify a compound suitable for the treatment of multiple sclerosis in a patient.

Preferably, the reference level is the level of the (said) at least one miRNA, e.g. 1, 2, 3, 4, 5, 6, 7, 8, 9, 10, 11, 12, 13, 14, or 15 miRNA(s), determined empirically by measuring a number of reference samples, preferably at least two reference samples, more preferably at least 2 to 40 reference samples, even more preferably at least 10 to 60 reference samples, and most preferably at least 50 to 100 reference samples, e.g. at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 reference samples, from (different) patients. Preferably or alternatively, said reference level is an average level. The average level is particularly determined by measuring a number of reference samples, preferably at least two reference samples, more preferably at least 2 to 40 reference samples, even more preferably at least 10 to 60 reference samples, and most preferably at least 50 to 100 reference samples, e.g. at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 reference samples, from a number of (different) patients and calculating the "middle" value (e.g. median or mean value) of the reference levels determined therein.

It is preferred that the level of the test sample of the patient will be determined in the same type of blood sample and/or will be obtained from a patient of the same gender and/or similar age or stage of life as the reference level of the reference sample.

In a kit for determining whether a patient responds to a therapeutic treatment of multiple sclerosis, the reference level is preferably the level of the at least one miRNA determined empirically by measuring a number of reference samples from patients suffering from multiple sclerosis. Further, in a kit for monitoring the course of multiple sclerosis in a patient or for adjusting the dose of a therapeutic drug applied for therapeutic treatment of multiple sclerosis in a patient, the reference level is preferably the level of the at least one miRNA determined empirically by measuring a number of reference samples from patients suffering from multiple sclerosis or from successfully treated multiple sclerosis patients.

As to the further definition of the term "reference level" and to the preferred embodiments of the "reference level", it is referred to the first aspect of the invention. As to the definition of the terms "miRNA fragments", "miRNA variants", or "miRNA fragment variants", it is also referred to the first aspect of the present invention.

It is preferred that the data carrier comprises information/instructions for use for determining whether a patient responds to a therapeutic treatment of multiple sclerosis. In this respect, it is referred to the method according to first aspect of the invention where this determination is described. It is also preferred that the data carrier comprises information/instructions for use for monitoring the course of multiple sclerosis in a patient. In this respect, it is referred to the method according to second aspect of the invention where this monitoring is described. It is also preferred that the data carrier comprises information/instructions for use for determining the risk of a relapse of multiple sclerosis in a patient. In this respect, it is referred to the method according to third aspect of the invention where this determination is described. It is further preferred that the data carrier comprises information/instructions for use for adjusting the dose of a therapeutic drug applied for therapeutic treatment of multiple sclerosis in a patient. In this respect, it is referred to the method according to fourth aspect of the invention where this adjustment is described. It is further preferred that the data carrier comprises information/instructions for use for identifying a compound suitable for the treatment of multiple sclerosis in a patient. In this respect, it is referred to the method according to fifth aspect of the invention where this identification is described. This information/these instructions for use may be comprised on a non-electronical data carrier, e.g. graphical data carrier such as an information leaflet, an information sheet, a bar code or an access code, or an electronical data carrier such as a floppy disk, a compact disk (CD), a digital versatile disk (DVD), a microchip or another semiconductor-based electronical data carrier. The access code may allow the access to a database, e.g. an internet database, a centralized, or a decentralized database, where this information/these instructions for use are deposited.

In a ninth aspect, the invention relates to natalizumab for use in the treatment of patients suffering from multiple sclerosis, wherein the patients are characterized by a decreased level of at least one miRNA, e.g. 1, 2, 3, or 4 miRNA(s), wherein the nucleotide sequence of the at least one miRNA is selected from the group consisting of SEQ ID NO: 1 to SEQ ID NO: 4, a fragment thereof, and a sequence having at least 80% sequence identity thereto, and/or an increased level of a miRNA, wherein the nucleotide sequence of the miRNA is SEQ ID NO: 9, a fragment thereof, or a sequence having at least 80% sequence identity thereto compared to healthy controls. Preferably, natalizumab is for use in the treatment of patients suffering from multiple sclerosis, wherein the patients are characterized by a decreased level of at least one miRNA, e.g. 1, 2, or 3 miRNA(s), wherein the nucleotide sequence of the at least one miRNA is selected from the group consisting of SEQ ID NO: 1, SEQ ID NO: 2, SEQ ID NO: 4, a fragment thereof, and a sequence having at least 80% sequence identity thereto, and/or an increased level of a miRNA, wherein the nucleotide sequence of the miRNA is SEQ ID NO: 9, a fragment thereof, or a sequence having at least 80% sequence identity thereto compared to healthy controls. Preferred miRNA combinations are comprised in FIG. 8.

The term "decreased level" of at least one miRNA preferably refers to a decrease of the level of the at least one miRNA by at least between 1 and 100%, more preferably by at least between 5 to 100%, even more preferably by at least between 10 to 100%, and most preferably by at least between 20 and 100%, e.g. by at least 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, or 100%, compared to a reference level of the at least one miRNA. The term "increased level" of at least one miRNA preferably refers to an increase of the level of the at least one miRNA by at least between 1 and 100%, more preferably by at least between 5 to 100%, even more preferably by at least between 10 to 100%, and most preferably by at least between 20 and 100%, e.g. by at least 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, or 100%, compared to a reference level of the at least one miRNA. Said reference level may be the level of the at least one miRNA determined empirically by measuring a number of reference samples, e.g. between 2 and 100 reference samples, between 10 and 80 reference samples or between 20 and 50 reference samples, from healthy subjects. Said subjects are subjects which do not suffer from multiple sclerosis.

The inventors of the invention have surprisingly observed that the administration of natalizumab results in an increase of the level of at least one miRNA, e.g. 1, 2, 3, or 4 miRNA(s), wherein the nucleotide sequence of the at least one miRNA is selected from the group consisting of SEQ ID NO: 1 to SEQ ID NO: 4, a fragment thereof, and a sequence having at least 80% sequence identity thereto, and/or in an decrease of the level of a miRNA, wherein the nucleotide sequence of the miRNA is SEQ ID NO: 9, a fragment thereof, or a sequence having at least 80% sequence identity thereto. Thus, said deregulation leads to a normalization of said miRNA levels by natalizumab therapy to miRNA levels in healthy controls.

The patient may be any organism such as vertebrate, particularly any mammal, including both a human and another mammal, e.g. an animal such as a rodent, a rabbit, or a monkey. The rodent may be a mouse, rat, hamster, guinea pig, or chinchilla. Preferably, the patient is a human or a rodent.

Preferably, multiples sclerosis (MS) is relapsing-remitting multiple sclerosis (RR-MS), secondary progressive multiple sclerosis (SPMS), progressive relapsing multiple sclerosis (PRMS), or primary progressive multiple sclerosis (PPMS). More preferably, multiples sclerosis (MS) is relapsing-remitting multiple sclerosis (RR-MS).

It is preferred that the nucleotide sequence of the at least one miRNA is selected from the group consisting of SEQ ID NO: 1, SEQ ID NO: 2, a fragment thereof, and a sequence having at least 80% sequence identity thereto.

It is further preferred that the nucleotide sequences of the miRNAs are (i) SEQ ID NO: 1 and SEQ ID NO: 2, a fragment thereof, or a sequence having at least 80% sequence identity thereto, (ii) SEQ ID NO: 1 and SEQ ID NO: 3, a fragment thereof, or a sequence having at least 80% sequence identity thereto, (iii) SEQ ID NO: 1 and SEQ ID NO: 4, a fragment thereof, or a sequence having at least 80% sequence identity thereto, (iv) SEQ ID NO: 2 and SEQ ID NO: 3, a fragment thereof, or a sequence having at least 80% sequence identity thereto, (v) SEQ ID NO: 2 and SEQ ID NO: 4, a fragment thereof, or a sequence having at least 80% sequence identity thereto, or (vi) SEQ ID NO: 3 and SEQ ID NO: 4, a fragment thereof, or a sequence having at least 80% sequence identity thereto.

The above (with respect to the ninth aspect) mentioned nucleotide sequence of the miRNA is selected from the group consisting of
(i) a nucleotide sequence according to SEQ ID NO: 1 to SEQ ID NO: 4 and SEQ ID NO: 9, (ii) a nucleotide sequence that is a fragment of the nucleotide sequence according to (i), preferably, a nucleotide sequence that is a fragment which is between 1 and 12, more preferably between 1 and 8, and most preferably between 1 and 5 or 1 and 3, i.e. 1, 2, 3, 4, 5, 6, 7, 8, 9, 10, 11, or 12, nucleotides shorter than the nucleotide sequence according to (i), and
(iii) a nucleotide sequence that has at least 80%, preferably at least 85%, more preferably at least 90%, and most preferably at least 95% or 99%, i.e. 80, 81, 82, 83, 84, 85, 86, 87, 88, 89, 90, 91, 92, 93, 94, 95, 96, 97, 98, or 99%, sequence identity to the nucleotide sequence according to (i) or nucleotide sequence fragment according to (ii).

It is particularly preferred that the nucleotide sequence as defined in (iii) has at least 80%, preferably at least 85%, more preferably at least 90%, and most preferably at least 95% or 99%, i.e. 80, 81, 82, 83, 84, 85, 86, 87, 88, 89, 90, 91, 92, 93, 94, 95, 96, 97, 98, or 99%, sequence identity over a continuous stretch of at least 10, 11, 12, 13, 14, 15, 16, 17, 18, 19, 20 or more nucleotides, preferably over the whole length, to the nucleotide sequence of the nucleotide according to (i) or nucleotide fragment according to (ii).

As to the test to determine whether the nucleotide sequence as defined in (ii) (i.e. nucleotide sequence fragment) or (iii) (i.e. nucleotide sequence variant or nucleotide sequence fragment variant) is regarded as a nucleotide sequence as defined in (ii) (i.e. nucleotide sequence fragment) or (iii) (i.e. nucleotide sequence variant or nucleotide sequence fragment variant) within the context of the present invention, it is referred to the first aspect of the invention.

As to the definition of the term "healthy controls" and as to the preferred embodiments of the healthy controls, it is referred to the first aspect of the invention.

In a tenth aspect, the invention relates to a polynucleotide (probe) for use in the detection of a miRNA to determine whether a patient responds to a therapeutic treatment of multiple sclerosis, to monitor the course of multiple sclerosis in a patient, to determine the risk of a relapse of multiple sclerosis in a patient, to adjust the dose of a therapeutic drug applied for treating multiple sclerosis in a patient, or to identify a compound suitable for the treatment of multiple sclerosis in a patient, wherein the nucleotide sequence of the miRNA is selected from the group consisting of SEQ ID NO: 1 to SEQ ID NO: 15.

Preferably, the polynucleotide (probe) is for use in the detection of a miRNA, wherein the nucleotide sequence of the miRNA is selected from the group consisting of SEQ ID NO: 1 to SEQ ID NO: 4 and SEQ ID NO: 5. More preferably, the polynucleotide (probe) is for use in the detection of a miRNA, wherein the nucleotide sequence is selected from the group consisting of SEQ ID NO: 1 and SEQ ID NO: 2.

In an alternative embodiment, the miRNA is not a miRNA having the nucleotide sequence according to SEQ ID NO: 3 or SEQ ID NO: 9.

It is preferred that
(i) the (above mentioned) polynucleotide (probe) is complementary to the miRNA, wherein the nucleotide sequence of the miRNA is selected from the group consisting of SEQ ID NO: 1 to SEQ ID NO: 15, preferably selected from the group consisting of SEQ ID NO: 1 to SEQ ID NO: 4 and SEQ ID NO: 9, and more preferably selected from the group consisting of SEQ ID NO: 1 and SEQ ID NO: 2,
(ii) the (above mentioned) polynucleotide (probe) is a fragment of the polynucleotide according to (i), preferably the polynucleotide is a fragment which is between 1 and 12, more preferably between 1 and 8, and most preferably between 1 and 5 or between 1 and 3, e.g. 1, 2, 3, 4, 5, 6, 7, 8, 9, 10, 11, or 12, nucleotides shorter than the polynucleotide according to (i), or (iii) the (above mentioned) polynucleotide (probe) has at least 80%, preferably at least 85%, more preferably at least 90%, and most preferably at least 95% or 99%, e.g. 80, 81, 82, 83, 84, 85, 86, 87, 88, 89, 90, 91, 92, 93, 94, 95, 96, 97, 98, or 99%, sequence identity to the polynucleotide sequence of the polynucleotide according to (i) or polynucleotide fragment according to (ii).

It is particularly preferred that the polynucleotide as defined in (iii) has at least 80%, preferably at least 85%, more preferably at least 90%, and most preferably at least 95% or 99%, e.g. 80, 81, 82, 83, 84, 85, 86, 87, 88, 89, 90, 91, 92, 93, 94, 95, 96, 97, 98, or 99%, sequence identity over a continuous stretch of at least 10, 11, 12, 13, 14, 15, 16, 17, 18, 19, 20 or more nucleotides, preferably over the whole length, to the polynucleotide sequence of the polynucleotide according to (i) or polynucleotide fragment according to (ii).

In addition, the polynucleotide as defined in (ii) (i.e. polynucleotide fragment) or (iii) (i.e. polynucleotide variant or polynucleotide fragment variant) is only regarded as a polynucleotide as defined in (ii) (i.e. polynucleotide fragment) or (iii) (i.e. polynucleotide variant or polynucleotide fragment variant) within the context of the present invention, if it is still capable of binding to, hybridizing with, or detecting a target miRNA of complementary sequence, e.g. the respective target miRNA according to SEQ ID NO: 1 to SEQ ID NO: 15, through one or more types of chemical bonds, usually through complementary base pairing, usually through hydrogen bond formation under stringent hybridization conditions. The skilled person can readily assess whether a polynucleotide as defined in (ii) (i.e. polynucleotide fragment) or (iii) (i.e. polynucleotide variant or polynucleotide fragment variant) is still capable of binding to, hybridizing with, recognizing or detecting a target miRNA of complementary sequence, e.g. the respective target miRNA according to SEQ ID NO: 1 to SEQ ID NO: 15. Suitable assays are described in the context of the sixth aspect of the present invention.

In an embodiment, the monitoring of the course of multiple sclerosis in a patient encompasses the determination, whether the patient benefits from a therapeutic treatment of multiple sclerosis. Said patient preferably receives or has received a therapeutic treatment of multiple sclerosis. In another embodiment, the monitoring of the course of multiple sclerosis in a patient encompasses the determination, whether multiple sclerosis in the patient improves, exacerbates or is stable, or whether multiple sclerosis in the patient further improves, again exacerbates or is stable, wherein the patient preferably receives or has received a therapeutic treatment of multiple sclerosis.

It is further preferred that the determination, monitoring, adjustment, or identification is carried out on the basis of a test sample isolated from a patient. Thus, the determination, monitoring, adjustment, or identification is carried out in vitro.

As to the term "test sample" and to the preferred embodiments of the "test sample", it is referred to the first aspect of the present invention.

The patient may be any mammal, including both a human and another mammal, e.g. an animal such as a rodent, a rabbit, or a monkey. The rodent may be a mouse, rat, hamster, guinea pig, or chinchilla. Preferably, the patient is a human or a rodent.

Preferably, multiples sclerosis (MS) is relapsing-remitting multiple sclerosis (RR-MS), secondary progressive multiple sclerosis (SPMS), progressive relapsing multiple sclerosis (PRMS), or primary progressive multiple sclerosis (PPMS). More preferably, multiples sclerosis (MS) is relapsing-remitting multiple sclerosis (RR-MS).

The polynucleotide (probe) may be comprised on a solid support, substrate, surface, platform or matrix. Preferably, the polynucleotide (probe) is part of a biochip/microarray. Said polynucleotide (probe) may be attached or linked to the solid support, substrate, surface, platform or matrix. Preferably, the polynucleotide (probe) is attached or linked to the solid phase of a biochip/microarray. Alternatively, the polynucleotide (probe) may be comprised on beads or microspheres. Preferably, the polynucleotide used is attached to or immobilized on the beads or microspheres, e.g. via a covalent or non-covalent linkage (see above). Preferably, said beads or microspheres are made of a synthetic material, e.g. polystyrene, polyethylene or polypropylene. It is preferred that said beads or microspheres have a mean diameter of between 2 to 20 microns, preferably 4 to 10 microns, most preferably 5 to 7 microns, e.g. 2, 3, 4, 5, 6, 7, 8, 9, 10, 11, 12, 13, 14, 15, 16, 17, 18, 19, or 20 microns. It is also preferred that said beads or microspheres are internally dyed, preferably with red and infrared fluorophores. For example, the bead or microsphere setting from Luminex may be used.

The polynucleotide (probe) may also be comprised as polynucleotide fragment, polynucleotide variant, or polynucleotide fragment variant on a solid support, substrate, surface, platform, matrix, particularly biochip/microarray, beads or microspheres.

In an eleventh aspect, the invention relates to a polynucleotide set comprising at least two different polynucleotides (probes), e.g. 2, 3, 4, 5, 6, 7, 8, 9, 10, 11, 12, 13, 14, or 15 polynucleotides (probes), according to the tenth aspect for use in the detection of at least two different miRNAs, e.g. 2, 3, 4, 5, 6, 7, 8, 9, 10, 11, 12, 13, 14, or 15 miRNAs, to determine whether a patient responds to a therapeutic treatment of multiple sclerosis, to monitor the course of multiple sclerosis in a patient, to determine the risk of a relapse of multiple sclerosis in a patient, to adjust the dose of a therapeutic drug applied for treating multiple sclerosis in a patient, or to identify a compound suitable for the treatment of multiple sclerosis in a patient.

It is preferred that the nucleotide sequences of the different miRNAs have SEQ ID NO: 1 to SEQ ID NO: 15. It is particularly preferred that the nucleotide sequences of the different miRNAs have SEQ ID NO: 1 to SEQ ID NO: 8 or SEQ ID NO: 9 to SEQ ID NO: 15. It is more preferred that the nucleotide sequences of the different miRNAs have SEQ ID NO: 1 to SEQ ID NO: 4 and SEQ ID NO: 9. It is particularly more preferred that the nucleotide sequences of the different miRNAs have SEQ ID NO: 1 to SEQ ID NO: 4. It is most preferred that the nucleotide sequences of the different miRNAs have SEQ ID NO: 1 and SEQ ID NO: 2, SEQ ID NO: 1 and SEQ ID NO: 3, SEQ ID NO: 1 and SEQ ID NO: 4, SEQ ID NO: 2 and SEQ ID NO: 3, SEQ ID NO: 2 and SEQ ID NO: 4, or SEQ ID NO: 3 and SEQ ID NO: 4. Other preferred combinations of the different miRNAs are listed in FIG. 8. As to other preferred nucleotide sequence combinations, it is referred to the seventh aspect of the invention.

The at least two different polynucleotides (probes) of the polynucleotide set used may be comprised on a solid support, substrate, surface, platform or matrix. Preferably, the at least two different polynucleotides (probes) of the polynucleotide set used are part of a biochip/microarray. Alternatively, the at least two different polynucleotides (probes) of the polynucleotide set used may be comprised on beads or microspheres. As to further preferred embodiments, it is referred to the tenth aspect of the invention.

BRIEF DESCRIPTION OF THE DRAWINGS

FIG. 1: Overview of miRNA sequences suitable for determining the response of a patient to therapeutic treatment of multiple sclerosis (MS), monitoring the course of MS, determining the risk for relapse of MS, adjusting the dose of a therapeutic drug applied for treating MS and/or identifying a compound suitable for treatment of MS. Experimental details: SEQ ID NO: sequence identification number, miRNA: identifier of the miRNA according to miRBase, Sequence: sequence of the miRNA.

FIG. 6: Comparison of expression of 5 miRNAs (SEQ ID NO: 1-4 and SEQ ID NO: 9) in patients suffering from Relapse Remitting Multiple Sclerosis (RRMS) before and after treatment with Natalizumab (Tysabri) and age-sex-matched healthy controls. To allow for direct comparison the expression levels of the healthy controls were scaled to the RRMS patients prior treatment with natalizumab. (A) Experimental details: SEQ ID NO: sequence identification number, miRNA: identifier of the miRNA according to miRBase, median (healthy control): median intensity obtained from microarray analysis for healthy controls scaled to RRMS-patients before treatment with natalizumab in counts/sec, median (RRMS baseline): median intensity obtained from microarray analysis for RRMS-patients before treatment with natalizumab in counts/sec, median (RRMS natalizumab): median intensity obtained from microarray analysis for RRMS-patients after treatment with natalizumab in counts/sec, log 2 FC (RRMS vs healthy control): log 2-value of Fold Change when comparing treatment-nave RRMS-patients (before natalizumab treatment) with age-sex matched healthy controls, log 2 FC (natalizumab vs RRMS): log 2-value of Fold Change when comparing RRMS-patients after treatment with natalizumab with treatment-naïve RRMS-patients (before treatment with natalizumab). (B) Graphical representation of the miRNA expression levels of SEQ ID NO: 1-4 and SEQ ID NO:9 of age-sex-matched healthy controls, RRMS patients before treatment with natalizumab (RRMS baseline) and RRMS patients after treatment with natalizumab (RRMS natalizumab). (C) Graphical representation of the Fold Change of RRMS patients before natalizumab treatment versus age-sex-matched healthy controls (log 2 FC RRMS vs healthy control) and Fold Change of RRMS patients after treatment with natalizumab versus RRMS patients before treatment (log 2 FC natalizumab vs RRMS) in respect to miRNAs SEQ ID NO: 1-4 and SEQ ID NO: 9.

FIG. 8: Overview of sets of miRNA biomarker (miRNA biomarker signatures MST-1 to MST-109) suitable for determining the response of a patient to therapeutic treatment of multiple sclerosis (MS), monitoring the course of MS, determining the risk for relapse of MS, adjusting the dose of a therapeutic drug applied for treating MS and/or identifying a compound suitable for treatment of MS. Experimental details: Signature: SEQ ID NO: sequence identification number, miRNA: identifier of the miRNA according to miRBase.

EXAMPLES

Figure 2:
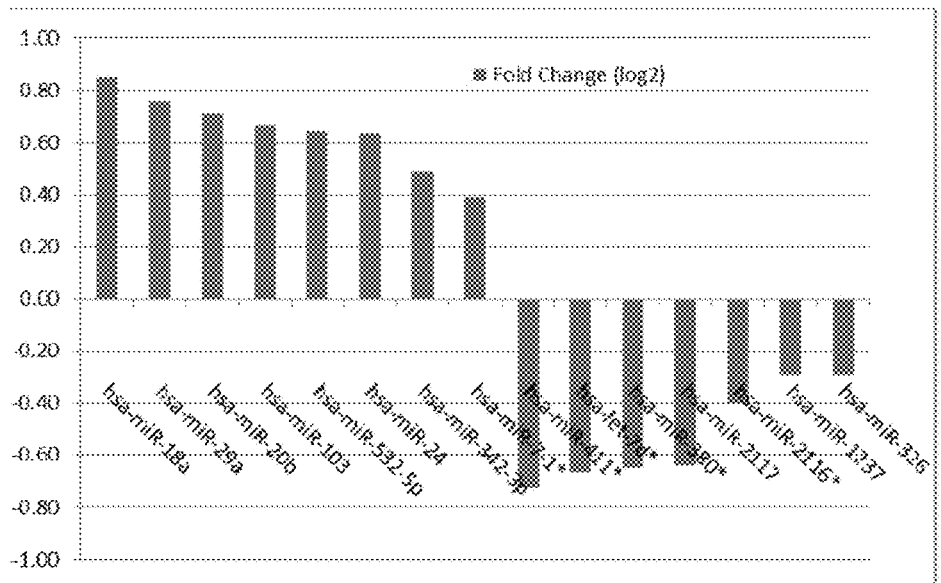
FIG. 2: (A) Overview of miRNAs that are found to be differentially regulated between patients suffering from Relapse Remitting Multiple Sclerosis (RRMS) before and after treatment with natalizumab (Tysabri). Experimental details: SEQ ID NO: sequence identification number, miRNA: identifier of the miRNA according to miRBase, median g1: median intensity obtained from microarray analysis for RRMS-patients before treatment with natalizumab in counts/sec, median g2: median intensity obtained from microarray analysis for RRMS-patients after treatment with natalizumab in counts/sec, log 2 median g1: log 2-value of median g1, log 2 median g2: log 2-value of median g2, qmedian: ratio of median g2/median g1 (=Fold Change), log 2qmedian: log 2-value of qmedian, ttest_rawpval: p-value obtained when applying t-test. (B) Graphical representation of the differential regulated miRNAs of (a). Y-axis: log 2 of Fold Change (log 2 qmedian). Upregulated miRNAs show a positive and downregulated miRNAs a negative log 2 Fold Change value.

The Examples are designed in order to further illustrate the present invention and serve a better understanding. They are not to be construed as limiting the scope of the invention in any way.

Materials and Methods
Study Population

MS patients were recruited at the Department of Neurology, Heinrich-Heine-University Düsseldorf, Germany and written informed consent was given. Patients were diagnosed definitive multiple sclerosis according to the 2005 revised McDonald criteria (McDonald W I, Compston A, Edan G et al. Recommended diagnostic criteria for multiple sclerosis: Guidelines from the International Panel on the Diagnosis of Multiple Sclerosis. Annals of Neurology 2001; 50:121-127 and Polman C H, Reingold S C, Edan G et al. Diagnostic criteria for multiple sclerosis: 2005 Revisions to the "McDonald Criteria". Annals of Neurology 2005; 58:840-846). If disease-modifying drugs had been used prior to natalizumab-therapy, patients adhered to a wash-out phase of at least 3 months. We included 17 patients with relapsing multiple sclerosis. The female/male ratio was 3.25. At the initiation of natalizumab treatment the mean age was 36.1±7.7 and the mean EDSS score was 2.44±1.30. Detailed demographical and clinical data are listed in Supplementary Table 1. Patients donated two blood samples in Paxgene® RNA tubes (BD, Franklin Lakes, N.J., USA): one immediately prior to the first natalizumab administration (before natalizumab) and one at least after 12 months of monthly infusions (after natalizumab), resulting in an intra-individual longitudinal approach. The control group comprised Paxgene® RNA tubes from 18 healthy individuals with a mean age of 37.2±12.5 at a female/male ratio of 3.0.

MicroRNA Microarray

Total RNA including microRNA was isolated from Paxgene® tubes using the miRNeasy® kit (Qiagen, Hilden, Germany). Samples were analyzed with a Geniom Realtime Analyzer (GRTA, CBC Comprehensive Biomarker Center, Heidelberg, Germany) using the Geniom Biochip miRNA *homo sapiens*. Each array contains 7 replicates of 866 miRNAs and miRNA star sequences as annotated in the Sanger miRBase 12.0 (Griffiths-Jones S, Grocock R J, van Dongen S et al. miRBase: microRNA sequences, targets and gene nomenclature. Nucleic Acids Research 2006; 34:D140-D144). Sample labelling with biotin was carried out by microfluidic-based enzymatic on-chip labelling of miRNAs (MPEA) as described before (Vorwerk S, Ganter K, Cheng Y et al. Microfluidic-based enzymatic on-chip labeling of miRNAs. New Biotechnology 2008; 25:142-149). Following hybridization for 16 hours at 42° C. the biochip was washed automatically and a program for signal enhancement was processed with the GRTA. The resulting detection pictures were evaluated using the Geniom Wizard Software. For each array, the median signal intensity was extracted from the raw data file such that for each miRNA seven intensity values were calculated corresponding to each replicate copy of miRBase on the array. Following background correction, the seven replicate intensity values of each miRNA were summarized by their median value. To normalize the data across different arrays, quantile normalization was applied and all further analyses were carried out using the normalized and background subtracted intensity values. Normal distribution of the data was verified with the Shapiro Wilk test. We considered our microarray approach as an exploratory first step. Thus, in order to avoid a loss of sensitivity (as expected with other approaches (Benjamini Y, Hochberg Y. Controlling the False Discovery Rate—A Practical and Powerful Approach to Multiple Testing. Journal of the Royal Statistical Society Series B-Methodological 1995; 57:289-300)) in the given setting, we based our analysis on parametric t-test (paired, two-tailed) for each miRNA separately to detect miRNAs with different expression levels between study groups. We then confirmed the resulting targets with established quantitative PCR analysis (qPCR).

qPCR

In order to quantify the levels of specific microRNAs the same RNA samples were used as for the microarray analysis. Taqman microRNA assays (Applied Biosystems) were used according to the manufacturer's instructions. The assays were the following (assay number): hsa-miR-18a (002422), hsa-miR-20b (001014), hsa-miR-29a (002623), hsa-miR-103 (000439), hsa-miR-326 (000542), mmu-miR-326 (001061). For human samples RNU6B (001093) was used as a housekeeping gene, for mouse samples snoRNA202 (001232) and snoRNA135 (001230). Samples were measured in duplicates and all resulting ΔCT-values were analyzed statistically using the paired t test for human samples and unpaired t test for mouse samples with Graphpad Prism 5.05 software.

Experimental Autoimmune Encephalomyelitis (EAE)

Induction and clinical scoring of EAE were performed as previously described (Aktas O, Smorodchenko A, Brocke S et al. Neuronal damage in autoimmune neuroinflammation mediated by the death ligand TRAIL. Neuron 2005; 46:421-432). Briefly, SJL/J mice were immunized subcutaneously with 200 μg PLP (Pepceuticals, UK) supplemented with 800 μg H37RA (Difco, USA) and emulsified in 100l complete Freund's adjuvant (CFA, Sigma, Germany) and 100 μl PBS. On day 10 post immunization, spleens and lymph nodes were harvested, a single cell suspension was prepared and the cells were restimulated with 10 μg/ml PLP139-151 in RPMI medium supplemented with 10% fetal calf serum, penicillin/streptomycin, glutamate and 2-mercaptoethanol (all Invitrogen). After 4 days the cells were harvested and $3\times10^7$ cells were injected into naïve female SJL/J mice intraperitoneally. Mice were sacrificed at day 13 or day 50 post transfer, spleens were harvested and single cell suspensions were prepared. RNA was isolated and qPCR was performed and statistically analysed as described above. Correlation between disease scores and miRNA levels were done using linear regression (Graphpad Prism 5.05 Software).

Results

Longitudinal Analysis of miRNA Expression by Microarray and qPCR

We analyzed the expression of 866 miRNA and miRNA* sequences in Paxgene® blood samples of 17 patients with relapsing MS intra-individually prior to the first natalizumab administration and after at least one year of continuous treatment. At treatment initiation the mean age was 35.3±7.6 and the mean EDSS score was 2.44±1.30. Following RNA isolation and on-chip labelling, miRNA expression profiles were measured using the Geniom microarray. Exploratory analysis revealed 14 miRNAs regulated in the course of natalizumab therapy (see FIGS. 1 and 2). Eight out of them were up-regulated after natalizumab therapy: miR-18a, miR-29a, miR-20b, miR-103, miR-532-5p, miR-24, miR-342-3p, miR-7-1*. Six miRNAs were down-regulated: miR-411*, let-7d*, miR-380*, miR-2117, miR-2116*, miR-1237. Following this exploratory microarray analysis, we performed validation by quantitative real-time PCR, accepted as the golden standard for miRNA quantification. Thereby, we concentrated on the up-regulated targets. We validated the 4 most strongly up-regulated targets, i.e. miR-18a, miR-20b, miR-29a and miR-103 by qPCR. All of which turned out to be significantly up-regulated after natalizumab therapy compared to prior to the treatment (see FIG. 2). Furthermore, we expanded our set of analysis by miR-326, as this miRNA has recently been implicated in MS. Quantitative polymerase chain reaction (qPCR) analysis revealed significant down-regulation upon natalizumab treatment (see FIG. 2).

Correlation with Disease-Relevant miRNAs

Figures 3, 4:
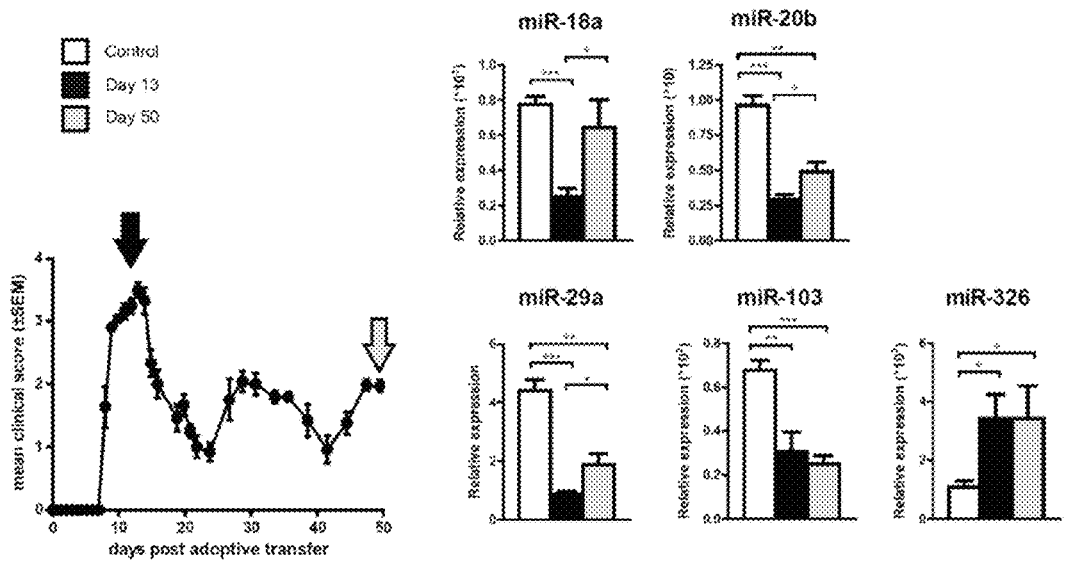
FIG. 3: Overview of miRNAs that are found to be differentially regulated between healthy controls and patients suffering from Relapse Remitting Multiple Sclerosis (RRMS), representing RRMS patients before treatment with natalizumab (Tysabri). In case that patients had used other drugs prior to natalizumab therapy, the RRMS patients adhered to a wash-out phase of at least 3 months. Experimental details: miRNA: identifier of the miRNA according to miRBase, median g1: median intensity obtained from microarray analysis for healthy controls in counts/sec, median g2: median intensity obtained from microarray analysis for RRMS-patients before treatment with natalizumab in counts/sec, log 2 median g1: log 2-value of median g1, log 2 median g2: log 2-value of median g2, qmedian: ratio of median g2/median g1 (=Fold Change), log 2qmedian: log 2-value of qmedian, ttest_rawp: p-value obtained when applying t-test, ttest_adjp: adjusted p-value in order to reduce false discovery rate by Benjamini-Hochberg adjustment, AUC: Area under the curve, limma_rawp: p-value obtained when applying limma-test, limmaadjp: adjusted p-value in order to reduce false discovery rate by Benjamini-Hochberg adjustment.
FIG. 4: Taqman qPCR analysis of miRNAs in adoptive transfer EAE. Spleens were harvested, splenocytes were isolated and washed immediately and RNA was isolated. Control animals were injected with PBS instead of restimulated PLP-specific T cells. Data are shown as mean fold change normalized to housekeeping gene±SEM. * $p<0.05$,  $p<0.01$, * $p<0.001$.

In order to substantiate the possible relevance of the miRNA candidates identified in our longitudinal study, we performed a confirmatory cross-sectional study. We performed a microarray analysis comparing the 17 natalizumab patients at baseline (that is after a 3-month wash-out period and prior to receiving the first dose of natalizumab) with microarray miRNA profiles obtained from Paxgene samples from age- and sex-matched healthy controls. miR-18a, miR-29a, miR-20b, miR-103, miR-532-5p, miR-24, and miR-7-1*were significantly down-regulated in MS vs. healthy controls (see FIG. 3). In addition, miR-411*, let7d*, miR-1237, and miR-326 were up-regulated in MS vs. healthy controls (see FIG. 3). In addition, see FIG. 6.

miRNA Dysregulation and Therapy Response

Figure 7:
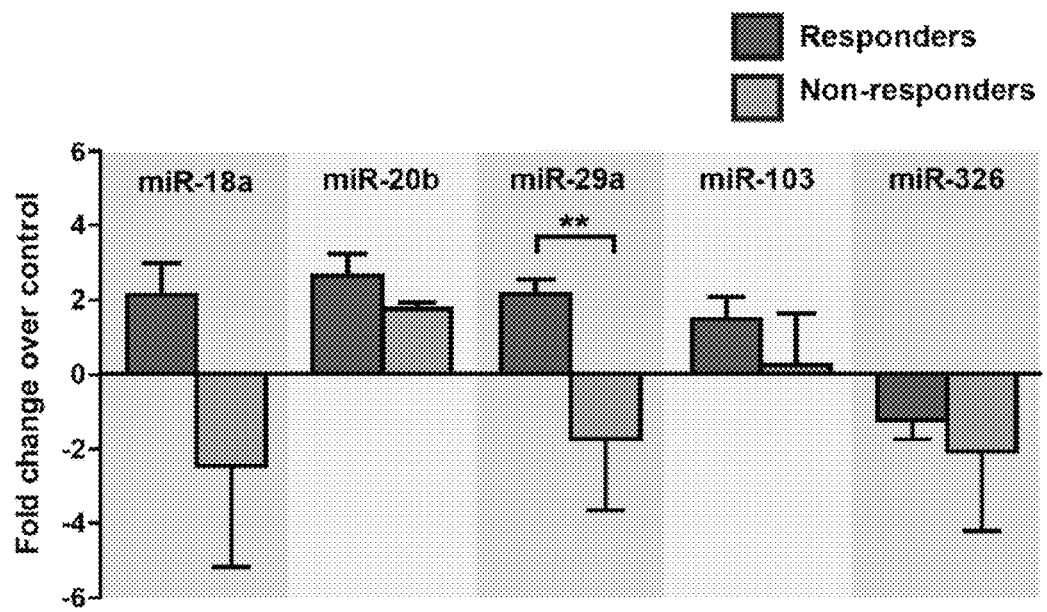
FIG. 7: Response of RRMS patients to treatment with natalizumab. 2 RRMS patients of the study group were considered non-responders, thereof one patient did have a relapse and one patient showed a disability progression during natalizumab therapy. The clinical outcome (response/no-response) of natalizumab therapy paralleled the level of microRNAs SEQ ID NO: 1, 2 3, 4 and 9 obtained from Taqman qPCR analysis as depicted by plotting the Fold Change microRNA expression levels.

Two of the 17 natalizumab-treated patients experienced sustained disease activity, defined by progression of disability or relapses despite of natalizumab treatment. We made a further exploratory analysis of the miRNA qPCR results of these two patients and observed that these non-responders displayed a different miRNA regulation pattern (FIG. 7): Two of the 5 miRNAs otherwise dysregulated by natalizumab in clinically stable patients showed a reverse regulation, i.e. reduction (miR-18a and miR-29a), and one of them showed a diminished increase (miR-20b).

miRNA Regulation in Experimental Autoimmune Encephalomyelitis (EAE)

Figure 5:
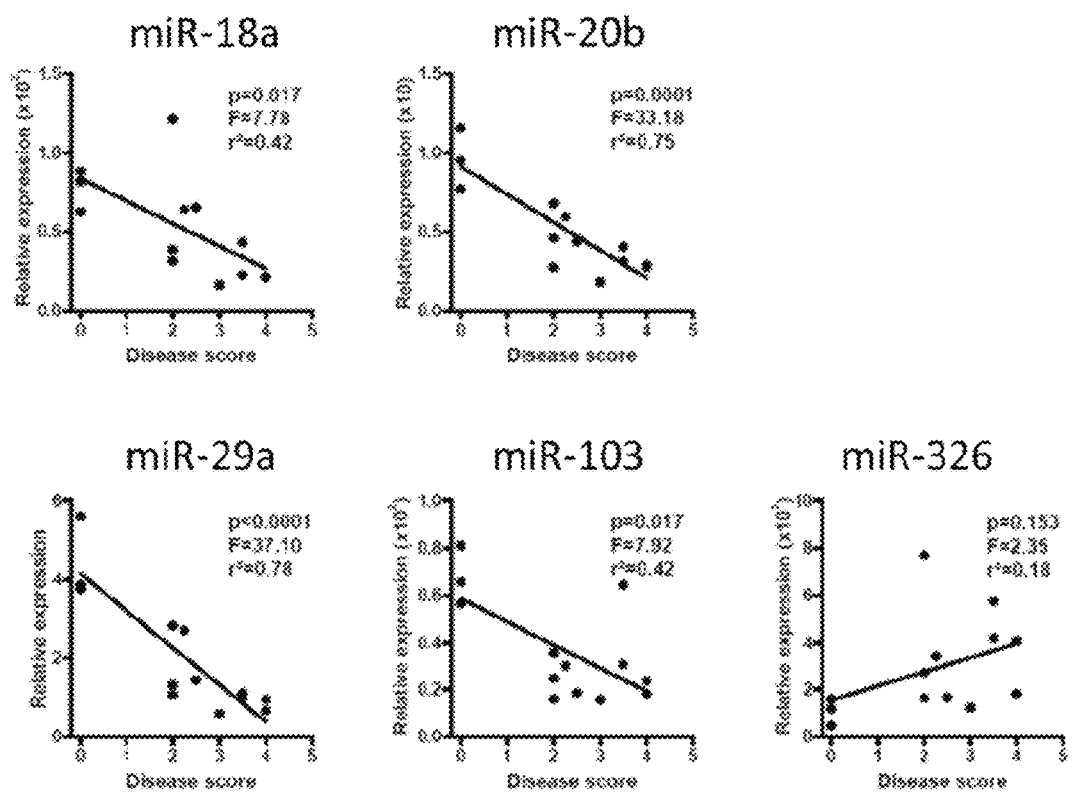
FIG. 5: Correlation of miRNA expression level with EDSS disease score (EDSS: expanded disability status score) by linear regression. Experimental data were obtained from Taqman qPCR analyses. SEQ-ID 1-4 (hsa-miR-18a, -20b, -29a, -103) showed negative correlation, SEQ ID NO 9 (hsa-miR-326) of miRNA expression level to EDSS.

The above observation suggested a possible link between disease activity and miRNA profile in the course of chronic autoimmune neuroinflammation. Therefore we next investigated miRNA expression profiles in EAE, an animal model of MS. Peripheral leukocytes were isolated from spleens of mice that experienced EAE in different stages of the disease, and miRNA patterns were investigated by qPCR. Since the local inflammation at the immunization site in active EAE may confound changes in leukocyte function and phenotype in terms of neuroinflammation-specific alterations, we chose the T cell transfer model of EAE in SJL/J mice. At the peak of disease, miR-18a, miR-20b, miR-29a and miR-103 were all significantly down-regulated, while miR-326 was up-regulated, compared to controls (see FIG. 4). At late-stage disease these changes in miRNA expression were reversed in some targets (miR-18a, miR-20b, miR-29a). A linear regression analysis revealed that the expression level of four of these miRNAs (all but miR-326) correlated negatively to disease severity. MiR-326 showed a trend to a positive correlation (see FIG. 5). The strongest association was found in miR-20b ($r^2=0.75$, p=0.0001, F=33.18) and miR-29a ($r^2=0.77$, p<0.0001, F=37.10).

Thus, summarizing the above, our study indicates that natalizumab, known to block inflammatory CNS infiltration by interference with lymphocyte adherence to the brain endothelium, has an impact on selected miRNAs. These miRNAs may serve as a tool for disease response monitoring and may constitute new targets for novel immunomodulatory therapies in RR-MS.

The invention claimed is:

1. A method of adjusting a therapeutic treatment of Relapsing-Remitting Multiple Sclerosis (RRMS) comprising the step of:
   (i) determining the level of at least one miRNA in erythrocytes, leukocytes, and thrombocytes isolated from a whole blood sample taken from a patient to whom at least once a drug to be used in said therapeutic treatment is administered or has been administered, wherein the nucleotide sequence of the at least one miRNA is selected from the group consisting of SEQ ID NO: 1 to SEQ ID NO: 4; and
   (ii) detecting an increase when the level of the at least one miRNA determined in step (i) is compared to a reference level of the at least one miRNA, which is determined in erythrocytes, leukocytes, and thrombocytes isolated from a whole blood sample taken from the patient prior to the administration of the drug, and subsequently administering to the patient at least once a renewed dose of the drug; or detecting no increase when the level of the at least one miRNA determined in step (i) is compared to the reference level of the at least one miRNA, and subsequently administering to the patient at least once an increased dose of the drug or a different drug.

2. The method of claim 1, wherein the drug is selected from the group consisting of natalizumab, interferon beta 1a, interferon beta 1b, glatiramer acetate, alemtuzumab, fingolimod, dimethylfumarate, and mitoxantrone.

3. The method of claim 2, wherein the whole blood sample is taken from the patient after the first administration of said drug.

4. A method of adjusting treatment of RRMS in a patient comprising the steps of:
   (i) treating the patient with a drug suitable for RRMS,
   (ii) determining the level of at least one miRNA in erythrocytes, leukocytes, and thrombocytes isolated from a whole blood sample taken from the patient, wherein the nucleotide sequence of the at least one miRNA is selected from the group consisting of SEQ ID NO: 1 to SEQ ID NO: 4, and
   (iii) detecting an increase when the level of the at least one miRNA determined in step (ii) is compared to a reference level of the at least one miRNA, which is determined in erythrocytes, leukocytes, and thrombocytes isolated from a whole blood sample taken from the patient prior to the administration of the drug, and subsequently administering to the patient at least once a renewed dose of the drug; or detecting no increase when the level of the at least one miRNA determined in step (ii) is compared to the reference level of the at least one miRNA, and subsequently administering to the patient at least once an increased dose of the drug or a different drug.

5. The method of claim 4, wherein the level of the miRNA is the expression level of the miRNA that is determined by nucleic acid hybridization or nucleic acid amplification and wherein
   (a) the nucleic acid hybridization is performed using a microarray/biochip or beads, or using in situ hybridization, and/or
   (b) the nucleic acid amplification is performed using real-time PCR.

6. A method of treating a patient suffering from RRMS with natalizumab comprising the steps of:
   (i) determining the level of at least one miRNA in erythrocytes, leukocytes, and thrombocytes isolated from a whole blood sample taken from a patient suffering from RRMS, wherein the nucleotide sequence of the at least one miRNA is selected from the group consisting of SEQ ID NO: 1 to SEQ ID NO: 4, and
   (ii) detecting a decrease when the level of the at least one miRNA determined in step (i) is compared to a reference level of the at least one miRNA in healthy controls, and
   (iv) treating said patient with natalizumab.

7. A method of treating RRMS in a patient comprising the steps of:
(i) isolating a whole blood sample from a patient who has been administered a drug for treating RRMS,
(ii) determining the level of at least one miRNA from erythrocytes, leukocytes and thrombocytes isolated from the whole blood sample, wherein the at least one miRNA is selected from the group consisting of SEQ ID NO: 1 to SEQ ID NO: 4, and
(iii) detecting an increase when the level of the at least one miRNA determined in step (ii) is compared to a reference level of the at least one miRNA, which has been determined prior to the administration of the drug to the patient, and subsequently continuing said treatment of the patient; or detecting no increase when the level of the at least one miRNA determined in step (ii) is compared to the reference level of the at least one miRNA, and subsequently discontinuing said treatment of the patient.

8. The method of claim 7, wherein the drug is selected from the group consisting of natalizumab, interferon beta 1a, interferon beta 1b, glatiramer acetate, alemtuzumab, fingolimod, dimethylfumarate, and mitoxantrone.

9. The method of claim 7, wherein the determination of the level of the at least one miRNA from the extracted total RNA comprises:
(a) transcribing the extracted total RNA into cDNA, and
(b) amplifying and determining the cDNA by qRT-PCR.

10. The method of claim 7, where an at least 1.2 fold increase of the level of the at least one miRNA indicates that the patient responds to said treatment.

11. The method of claim 6, wherein the level of the at least one miRNA is determined in the total RNA isolated from the erythrocytes, leukocytes, and thrombocytes.

12. The method of claim 7, wherein the level of the at least one miRNA is determined in the total RNA isolated from the erythrocytes, leukocytes, and thrombocytes of the test whole blood sample.

13. The method of claim 1, wherein an at least 1.4 fold increase of the level of the at least one miRNA in the whole blood sample when compared to the reference level of the at least one miRNA is detected.

14. The method of claim 4, wherein the drug is selected from the group consisting of natalizumab, interferon beta 1a, interferon beta 1b, glatiramer acetate, alemtuzumab, fingolimod, dimethylfumarate, and mitoxantrone.

* * * * *